(12) United States Patent
Davidson et al.

(10) Patent No.: US 9,181,544 B2
(45) Date of Patent: Nov. 10, 2015

(54) THERAPEUTIC COMPOUNDS

(75) Inventors: Beverly L. Davidson, Iowa City, IA (US); Ryan L. Boudreau, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 13/985,023

(22) PCT Filed: Feb. 13, 2012

(86) PCT No.: PCT/US2012/024904
§ 371 (c)(1),
(2), (4) Date: Aug. 12, 2013

(87) PCT Pub. No.: WO2012/109667
PCT Pub. Date: Aug. 16, 2012

(65) Prior Publication Data
US 2014/0142288 A1 May 22, 2014

Related U.S. Application Data

(60) Provisional application No. 61/442,218, filed on Feb. 12, 2011, provisional application No. 61/522,632, filed on Aug. 11, 2011.

(51) Int. Cl.
*C12N 15/11* (2006.01)
*C07H 19/00* (2006.01)
*C12N 15/113* (2010.01)

(52) U.S. Cl.
CPC .............. *C12N 15/11* (2013.01); *C12N 15/111* (2013.01); *C12N 15/113* (2013.01); *C12N 2310/141* (2013.01); *C12N 2310/531* (2013.01); *C12N 2320/53* (2013.01); *C12N 2330/51* (2013.01)

(58) Field of Classification Search
None
See application file for complete search history.

(56) References Cited

U.S. PATENT DOCUMENTS

| | | | |
|---|---|---|---|
| 4,962,091 A | 10/1990 | Eppstein et al. | |
| 5,139,941 A | 8/1992 | Muzyczka et al. | |
| 5,173,414 A | 12/1992 | Lebkowski et al. | |
| 5,350,674 A | 9/1994 | Boenisch et al. | |
| 5,585,362 A | 12/1996 | Wilson et al. | |
| 5,720,720 A | 2/1998 | Laske et al. | |
| 7,232,806 B2 | 6/2007 | Tuschl et al. | |
| 7,320,965 B2 * | 1/2008 | Sah et al. | 514/44 A |
| 7,902,352 B2 | 3/2011 | Kaemmerer et al. | |
| 8,227,592 B2 | 7/2012 | Harper et al. | |
| 8,258,286 B2 | 9/2012 | Davidson | |
| 8,329,890 B2 | 12/2012 | Davidson et al. | |
| 8,481,710 B2 | 7/2013 | Davidson et al. | |
| 8,487,088 B2 | 7/2013 | Davidson et al. | |
| 8,524,879 B2 | 9/2013 | Davidson et al. | |
| 8,524,881 B2 | 9/2013 | Davidson | |
| 8,691,567 B2 | 4/2014 | Harper et al. | |
| 8,779,116 B2 | 7/2014 | Davidson et al. | |
| 2002/0114780 A1 | 8/2002 | Bankiewicz et al. | |
| 2002/0141980 A1 | 10/2002 | Bankiewicz et al. | |
| 2002/0187127 A1 | 12/2002 | Bankiewicz | |
| 2004/0023390 A1 | 2/2004 | Davidson et al. | |
| 2004/0162255 A1 | 8/2004 | Kaemmerer | |
| 2004/0241854 A1 | 12/2004 | Davidson et al. | |
| 2005/0042646 A1 | 2/2005 | Davidson et al. | |
| 2005/0106731 A1 | 5/2005 | Davidson et al. | |
| 2005/0255086 A1 | 11/2005 | Davidson et al. | |
| 2006/0009408 A1 | 1/2006 | Davidson et al. | |
| 2006/0130176 A1 | 6/2006 | Reyes-Taboada et al. | |
| 2006/0257912 A1 | 11/2006 | Kaemmerer et al. | |
| 2008/0039418 A1 | 2/2008 | Freier | |
| 2008/0176812 A1 | 7/2008 | Davidson et al. | |
| 2008/0274989 A1 | 11/2008 | Davidson et al. | |
| 2009/0036395 A1 | 2/2009 | Davidson et al. | |
| 2009/0105169 A1 | 4/2009 | Davidson et al. | |
| 2009/0130751 A1 | 5/2009 | Davidson et al. | |
| 2010/0008981 A1 | 1/2010 | Kaemmerer et al. | |
| 2010/0144026 A1 | 6/2010 | Davidson et al. | |
| 2010/0190243 A1 | 7/2010 | Davidson et al. | |
| 2010/0325746 A9 | 12/2010 | Kaemmerer et al. | |
| 2011/0111491 A1 | 5/2011 | Davidson et al. | |
| 2011/0212520 A1 | 9/2011 | Davidson et al. | |
| 2011/0244561 A1 | 10/2011 | Davidson et al. | |
| 2011/0244562 A1 | 10/2011 | Davidson et al. | |
| 2014/0163214 A1 | 6/2014 | Davidson et al. | |
| 2014/0179003 A1 | 6/2014 | Harper et al. | |
| 2014/0303362 A1 | 10/2014 | Davidson | |

FOREIGN PATENT DOCUMENTS

| | | |
|---|---|---|
| WO | WO 94/07529 | 4/1994 |
| WO | WO 2004/047872 | 6/2004 |
| WO | WO 2005/081714 | 9/2005 |

(Continued)

OTHER PUBLICATIONS

Anderson et al., "Experimental validation of the importance of seed complement frequency to siRNA specificity", *RNA* 14, 853-861 (2008).
Bachevalier et al., "Aged monkeys exhibit behavioral deficits indicative of widespread cerebral dysfunction", *Neurobiol Aging* 12, 99-111 (1991).
Birmingham et al. "3' UTR seed matches, but not overall identity, are associated with RNAi off-targets", *Nature Methods* vol. 3 (1), 199-204 (2006).
Birmingham et al., "A protocol for designing siRNAs with high functionality and specificity", *Nat Protoc* 2 (9), 2068-2078 (2007).
Boden, "Enhanced gene silencing of HIV-1 specific siRNA using microRNA designed hairpins," *Nucleic Acids Res*, 32, 1154-1158, (2004).

(Continued)

*Primary Examiner* — Tracy Vivlemore
*Assistant Examiner* — Kate Poliakova
(74) *Attorney, Agent, or Firm* — Viksnins Harris & Padys PLLP

(57) ABSTRACT

The present invention is directed to RNA interference (RNAi) molecules targeted against a Huntington's disease nucleic acid sequence, and methods of using these RNAi molecules to treat Huntington's disease.

20 Claims, 8 Drawing Sheets

(56) References Cited

FOREIGN PATENT DOCUMENTS

| WO | WO 2005/105995 | | 11/2005 |
|---|---|---|---|
| WO | WO 2006/083800 | | 8/2006 |
| WO | WO 2007/022506 | | 2/2007 |
| WO | WO 2007/051045 | A2 | 5/2007 |
| WO | WO 2007/089584 | | 8/2007 |
| WO | WO 2008/134646 | A2 | 11/2008 |
| WO | WO 2008/134646 | A3 | 11/2008 |
| WO | WO 2008/150897 | A2 | 12/2008 |

OTHER PUBLICATIONS

Boudreau et al., "Minimizing variables among hairpin-based RNAi vectors reveals the potency of shRNAs", RNA 14, 1834-1844 (2008).
Boudreau et al., "Nonallele-specific Silencing of Mutant and Wild-type Huntingtin Demonstrates Therapeutic Efficacy in Huntington's Disease Mice", Molecular Therapy vol. 17 (6), 1053-1063 (2009)
Boudreau et al., "Artificial MicroRNAs as siRNA Shuttles: Improved Safety as Compared to shRNAs in vitro and in vivo", Molecular Therapy vol. 17 (1), 169-175 (2009).
Boudreau et al., "Rational design of therapeutic siRNAs: Minimizing off-targeting potential to improve the safety of RNAi therapy for Huntington's disease", Molecular Therapy vol. 19 (12), 2169-2177 (2011).
Bradford et al., "Mutant huntingtin in glial cells exacerbates neurological symptoms of Huntington disease mice", J Biol Chem 285, 10653-10661 (2010).
Bramsen et al., "A screen of chemical modifications identifies position-specific modification by UNA to most potently reduce siRNA off-target effects", Nucleic Acids Res 38 (17), 5761-5773 (2010).
Brandenberger, GenBank direct submission Accession CN300012 (Feb. 4, 2011) [online]; downloaded from http://ncbi.nlm.nih.gov/nucest/CN300012 on May 31, 2012.
Burchard et al., "MicroRNA-like off-target transcript regulation by siRNAs is species specific", RNA 15 (2), 308-315 (2009).
Denovan-Wright, "RNAi: a potential therapy for the dominantly inherited nucleotide repeat diseases", Gene Therapy, 13, 525-531, (2006).
De Paula, "Hydrophobization and bioconjugation for enhanced siRNA delivery and targeting", RNA, 13, 431-456, (2007).
Dodiya et al., "Differential transduction following basal ganglia administration of distinct pseudotyped AAV capsid serotypes in non-human primates", Mol Ther 18, 579-587 (2010).
Fedorov et al., "Off-target effects by siRNA can induce toxic phenotype", RNA 12, 1188-1196 (2006).
Franich et al., "AAV vector-mediated RNAi of mutant huntingtin expression is neuroprotective in a novel genetic rat model of Huntington's disease", Mol Ther 16, 947-956 (2008).
Grimm, "Fatality in mice due to oversaturation of cellular microRNA/short hairpin RNA pathways," Nature, 441, 537-541, (2006).
Hadaczek et al., "Transduction of nonhuman primate brain with adeno-associated virus serotype 1: vector trafficking and immune response", Hum Gene Ther 20, 225-237 (2009).
Halperin et al., "Allegro: analyzing expression and sequence in concert to discover regulatory programs", Nucleic Acids Res 37 (5), 1566-1579 (2009).
Han et al., "Molecular basis for the recognition of primary microRNAs by the Drosha-DGCR8 Complex" Cell, vol. 125, 887-901 (2006).
Harper et al., "RNA interference improves motor and neuropathological abnormalities in a Huntington's disease mouse model", PNAS, vol. 102, 5820-5825 (2005).
Huang et al., "The DAVID Gene Functional Classification Tool: a novel biological module-centric algorithm to functionally analyze large gene lists", Genome Biol 8 (9), R183 (2007).
Huang et al., "High-capacity adenoviral vector-mediated reduction of huntingtin aggregate load in vitro and in vivo", Hum Gene Ther 18, 303-311 (2008).
Jackson et al., "Position-specific chemical modification of siRNAs reduces "off-target" transcript silencing", RNA 12 (7), 1197-1205, (2006).
Johnson et al., "Huntington's disease: progress toward effective disease-modifying treatments and a cure", Human Molecular Genetics, vol. 19 (1), R98-R102 (2010).
Khvorova, "Functional siRNAs and miRNAs Exhibit strand Bias", Cell, 115, 209-216 (1 supplementary page), (2003).
Landgraf, "A Mammalian microRNA Expression Atlas Based on Small RNA Library Sequencing", Cell, 129, 1401-1414, (2007).
Li, "Defining the optimal parameters for hairpin-based knockdown constructs," RNA, 13, 1765-1774, (2007).
Liu et al., "Specific inhibition of Huntington's disease gene expression by siRNAs in cultured cells", Proc. Japan Acad., 79, Ser. B, No. 10, pp. 293-298, 2003.
McBride et al., "Artificial miRNAs mitigate shRNA-mediated toxicity in the brain: Implications for the therapeutic development of RNAi",PNAS, vol. 105, No. 15, pp. 5868-5873, 2008.
McBride et al., "Preclinical Safety of RNAi-Mediated HTT Suppression in the Rhesus Macaque as a Potential Therapy for Huntington's Disease", Molecular Therapy vol. 19 (12), 2152-2162 (2011).
McMahon, "Optimisation of electrotransfer of plasmid into skeletal muscle by pretreatment with hyaluronidase—increased expression with reduced muscle damage", Gene Therapy 8, 1264-1270 (2001).
Miyagishi, "Optimization of an siRNA-expression system with an improved hairpin and its significant suppressive effects in mammalian cells", J. Gene Med., 6, 714-723, (2004).
Patent Cooperation Treaty, International Searching Authority, Search Report and Written Opinion, 11 pages, Jun. 22, 2012.
Pfister et al., "Five siRNAs targeting three SNPs may provide therapy for three-quarters of Huntington's disease patients", Curr Biol 19, 774-778 (2009).
Rodriguez-Lebron, et al., "Intrastriatal rAAV-Mediated Delivery of Anti-huntingtin shRNAs Induces Partial Reversal of Disease Progression in R6/1 Huntington's Disease Transgenic Mice", Molecular Therapy vol. 12, No. 4, pp. 618-633, 2005.
Schwarz, "Asymmetry in the Assembly of the RNAi Enzyme Complex", Cell, 115, 199-208 (2003).
Silva, "Second-generation shRNA libraries covering the mouse and human genomes", Nature Genetics, 37, 1281-1288 (13 supplementary pages), (2005).
Smith et al., "A simplified baculovirus-AV expression vector system coupled with one-step affinity purification yields high-titer rAAV stocks from insect cells", Mol Ther 17, 1888-1896 (2009).
Stegmeier, "A lentiviral microRNA-based system for single-compy polymerase II-regulated RNA interference in mammalian cells", PNAS, 102, 13212-13219 (3 supplementary pages), (2005).
Urabe et al., "Insect cells as a factory to produce adeno-associated cirus type 2 vectors", Hum Gene Ther 13 (16), 1935-1943 (2002).
Vaish et al., "Improved specificity of gene silencing by siRNAs containing unlocked nucleobase analogs", Nucleic Acids Res 39 (5), 1823-1832 (2011).
Vermeulen, "The contributions of dsRNA structure to Dicer specificity and efficiency," RNA, 11, 674-682, (2005).
Wang et al., "Clinico-pathological rescue of a model mouse of Huntington's disease by siRNA", Neuroscience Research 53, pp. 241-249, 2005.
Xia, "RNAi suppresses polyglutamine-induced neurodegeneration in a model of spinocerebellar ataxia", Nature Medicine, 10, 816-820 (4 supplementary pages), (2004).
Penn et al., "Probe #16038 for gene expression analysis in human heart cell sample", XP002733676, Database accession No. ABA37572, 2 pages (Jan. 23, 2002).

\* cited by examiner

THERAPEUTIC COMPOUNDS

CLAIM OF PRIORITY

This application claims priority to U.S. Provisional Application No. 61/442,218, filed on Feb. 12, 2011 and U.S. Provisional Application No. 61/522,632, filed on Aug. 11, 2011. These applications are incorporated by reference herein.

GOVERNMENT SUPPORT

This invention was made with Government support under NS-50210, NS-068099, and DK-54759 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, is named 17023.113US1_SL.txt and is 51,200 bytes in size.

BACKGROUND OF THE INVENTION

RNAi directs sequence-specific gene silencing by double-stranded RNA (dsRNA) which is processed into functional small inhibitory RNAs (~21 nt). In nature, RNAi for regulation of gene expression occurs primarily via small RNAs known as microRNAs (miRNAs). Mature microRNAs (~19-25 nts) are processed from larger primary miRNA transcripts (pri-miRNAs) which contain stem-loop regions. Via a series of processing events catalyzed by the ribonucleases, Drosha and Dicer, the miRNA duplex region is liberated and a single strand (the antisense "guide" strand) is then incorporated into the RNA Induced Silencing Complex (RISC), thus generating a functional complex capable of base-pairing with and silencing target transcripts. The mode of target repression primarily depends upon the degree of complementarity; transcript cleavage typically requires a high-degree of base-pairing, whereas translational repression and mRNA destabilization occurs when small RNAs bind imperfectly to target transcripts (most often in the 3' UTR). Indeed for the latter, short stretches of complementarity—as little as 6 bp—may be sufficient to cause gene silencing.

SUMMARY OF THE INVENTION

The present invention provides an isolated miRNA shuttle vector that expresses a therapeutic siRNA with limited off target toxicity. In certain embodiments, embedding an siRNA that exhibits off target toxicity in the context of an miRNA shuttle vector of the present invention limits the off target toxicity of the siRNA. In certain embodiments, the miRNA shuttle vector expresses a therapeutic siRNA in the brain with limited off target toxicity. In certain embodiments, the miRNA shuttle vector expresses a therapeutic siRNA in the striatum with limited off target toxicity. In certain embodiments, the miRNA shuttle vector expresses a therapeutic siRNA in the cerebrum with limited off target toxicity.

The present invention provides an isolated nucleic acid encoding a primary transcript (pri-miRNA) including, in order of position, a 5'-flanking region, a non-guide (passenger) region, a loop region, a guide region, and a 3'-flanking region, wherein the guide region is at least 90% identical to CGACCAUGCGAGCCAGCA (miHDS.1 guide, SEQ ID NO:7), AGUCGCUGAUGACCGGGA (miHDS.2 guide, SEQ ID NO:8) or ACGUCGUAAACAAGAGGA (miHDS.5 guide, SEQ ID NO:9) and the non-guide region is at least 80% complementary to the guide region. In certain embodiments, the 5'-flanking region is contiguously linked to the non-guide region, the loop region is positioned between the non-guide region and the guide region, and the guide region is contiguously linked to the 3'-flanking region. As used herein, the term "siRNA guide region" is a single-stranded sequence of RNA that is complementary to a target sequence. As used herein, the term "siRNA non-guide region" is a single-stranded sequence of RNA that is complementary to the "siRNA guide region." Thus, under the proper conditions, the siRNA guide region and the siRNA non-guide region associate to form an RNA duplex. As used herein, all nucleic acid sequences are listed, as is customary, in a 5' to 3' direction.

In certain embodiments, the non-guide region is about 15-30 nucleotides in length, and is about 70-100% complementary to the guide region, which is about 15-30 nucleotides in length. In certain embodiments, the guide region is at least 90% identical to CGACCAUGCGAGCCAGCA (miHDS.1 guide, SEQ ID NO:7), AGUCGCUGAUGACCGGGA (miHDS.2 guide, SEQ ID NO:8) or ACGUCGUAAACAAGAGGA (miHDS.5 guide, SEQ ID NO:9) and the non-guide region is at least 80% complementary to the guide region.

In certain embodiments, the 5'-flanking region contains a 5'-joining sequence contiguously linked to the non-guide region. As used herein, the term "joining site" or a "joining sequence" is a short nucleic acid sequence of less than 60 nucleotides that connects two other nucleic acid sequences. In certain embodiments, the joining site is of a length of any integer between 4 and 50, inclusive. In certain embodiments, the 5'-joining sequence consists of 5-8 nucleotides (e.g., consists of 6 nucleotides). In certain embodiments, the 5'-joining sequence encodes GUGAGCGA (SEQ ID NO:12) or GUGAGCGC (SEQ ID NO:13).

In certain embodiments, the 5'-flanking region further comprises a 5'-bulge sequence positioned upstream from the 5'-joining sequence. As used herein, the term "bulge sequence" is a region of nucleic acid that is non-complementary to the nucleic acid opposite it in a duplex. For example, a duplex will contain a region of complementary nucleic acids, then a region of non-complementary nucleic acids, followed by a second region of complementary nucleic acids. The regions of complementary nucleic acids will bind to each other, whereas the central non-complementary region will not bind, thereby forming a "bulge." In certain embodiments the two strands of nucleic acid positioned between the two complementary regions will be of different lengths, thereby forming a "bulge." In certain embodiments, the 5'-bulge sequence will contain from 2 to 15 nucleotides. In certain embodiments, the 5'-bulge sequence consists of about 1-10 nucleotides. In certain embodiments, the 5'-bulge sequence encodes UAAACUCGA (SEQ ID NO:14). In certain embodiments, the 5'-bulge sequence has from 0-50% complementarity to the 3'-bulge sequence. The XhoI restriction site is CTCGAG (SEQ ID NO:15) (with "T" being "U" in RNA form in this and all other sequences listed herein).

In certain embodiments, the 5'-flanking region further contains a 5'-spacer sequence positioned upstream from the 5'-bulge sequence. In certain embodiments, the 5'-spacer sequence consists of 9-12 nucleotides, such as 10-12 nucleotides. In certain embodiments, the 5'-spacer sequence has from 60-100% complementarity to a 3'-spacer sequence. In certain embodiments, the 5'-bulge sequence comprises a cloning site, such as an XhoI site. In certain embodiments, the 5'-spacer sequence is UGGUACCGUU (SEQ ID NO:16).

In certain embodiments, the 5'-flanking region further contains a 5'-upstream sequence positioned upstream from the 5'-spacer sequence. In certain embodiments, the 5'-upstream sequence is about 5-5000 nucleotides in length, such as 30-2000 nucleotides in length.

In certain embodiments, the 3'-flanking region contains a 3'-joining sequence contiguously linked to the guide region. In certain embodiments, the joining site is of a length of any integer between 4 and 50, inclusive. In certain embodiments, the 3' joining sequence consists of 5-8 nucleotides, (e.g., consists of 6 nucleotides). In certain embodiments, the 3'-joining sequence is at least about 85% complementary to a 5'-joining sequence. In certain embodiments, the 3'-joining sequence encodes CGCYUAC (SEQ ID NO:17), wherein Y is C or U. In certain embodiments, the 3'-joining sequence encodes CGCCUAC (SEQ ID NO:18).

In certain embodiments, the 3'-flanking region further comprises a 3'-bulge sequence positioned downstream from the 3'-joining sequence. In certain embodiments, the 3'-bulge sequence comprises a cloning site, such as a SpeI/XbaI site or a SpeI site. The SpeI/XbaI site is encoded by CTCAGA (SEQ ID NO:19), and the SpeI site is encoded by CTCAGT (SEQ ID NO:20). In certain embodiments, the 3'-bulge sequence consists of about 1-15 nucleotides (such as 2-15 nucleotides or 1-10 nucleotides). In certain embodiments, the 3'-bulge sequence encodes UAG (SEQ ID NO: 32). In certain embodiments, the 5'-bulge sequence is complementary to the 3'-bulge sequence at only one nucleotide at each end of the sequence.

In certain embodiments, the 3'-flanking region further contains a 3'-spacer sequence positioned downstream from the 3'-bulge sequence. In certain embodiments, the 3'-spacer sequence consists of 9-12 nucleotides, such as 10-12 nucleotides. In certain embodiments, the 3'-spacer sequence is AGCGGCCGCCA (SEQ ID NO:21). In certain embodiments, the 3'-spacer sequence is at least about 70% complementary to a 5'-spacer sequence.

In certain embodiments, the 3'-flanking region further contains a 3'-downstream sequence positioned downstream from the 3'-spacer sequence. In certain embodiments, a 5'-upstream sequence does not significantly pair with the 3'-downstream sequence. As used herein, the term "does not significantly pair with" means that the two strands are less than 20% homologous. In certain embodiments, the 3'-downstream sequence is about 5-5000 nucleotides in length, such as 30-2000 nucleotides in length.

In certain embodiments, the loop region is from 4-20 nucleotides in length, such as 15-19 nucleotides in length. From 0-50% of the loop region can be complementary to another portion of the loop region. As used herein, the term "loop region" is a sequence that joins two complementary strands of nucleic acid. In certain embodiments, 1-3 nucleotides of the loop region are immediately contiguous to the complementary strands of nucleic acid may be complementary to the last 1-3 nucleotides of the loop region. For example, the first two nucleic acids in the loop region may be complementary to the last two nucleotides of the loop region. In certain embodiments, the loop region is 17 nucleotides in length. In certain embodiments, the loop region encodes CUNNNNNNNNNNNNNNNGG (SEQ ID NO:22) or CCNNNNNNNNNNNNNNNGG (SEQ ID NO:23). In certain embodiments, the loop region encodes CUGUGAAGC-CACAGAUGGG (SEQ ID NO:24) or CCGUGAAGCCA-CAGAUGGG (SEQ ID NO:25).

The present invention further provides an RNA encoded by nucleic acid described herein.

The present invention further provides an expression cassette containing a promoter contiguously linked to a nucleic acid described herein. In certain embodiments, the promoter is a polII or a polIII promoter, such as a U6 promoter (e.g., a mouse U6 promoter). In certain embodiments, the expression cassette further contains a marker gene. In certain embodiments, the promoter is a polII promoter. In certain embodiments, the promoter is a tissue-specific promoter. In certain embodiments, the promoter is an inducible promoter. In certain embodiments, the promoter is a polIII promoter.

The present invention provides a vector containing an expression cassette described herein. In certain embodiments, the vector is an adeno-associated virus (AAV) vector.

The present invention provides a non-human animal comprising the nucleic acid, the expression cassette, or the vector described herein.

The present invention provides an isolated nucleic acid between 80-4000 nucleotides in length comprising (or consisting of) an miHDS.1 guide GUCGACCAUGCGAGC-CAGCAC (SEQ ID NO:4); an miHDS.2 guide AUAGUCGCUGAUGACCGGGAU (SEQ ID NO:5); an miHDS.5 guide UUACGUCGUAAACAAGAGGAA (SEQ ID NO:6); an miHDS.1 CUCGAGUGAGCGAUGCUG-GCUCGCAUGGUCGAUACUGUAAAGCCACAG AUGGGUGUCGACCAUGCGAGCCAGCAC-CGCCUACUAGA (SEQ ID NO:1), GCGUUUAGUGAAC-CGUCAGAUGGUACCGUUUAAACUCGAGUGAGCGA UGCUGGCUCGCAUGGUCGAUACU-GUAAAGCCACAGAUGGGUGUCGACC AUGCGAGC-CAGCACCGCCUACUAGAGCGGCCGCCA-CAGCGGGGAGAUC CAGACAUGAUAAGAUACAUU (SEQ ID NO:10), or CUCGAGUGAGCGAUGCUG-GCUCGCAUGGUCGAUACUGUAAAGCCACAG AUGGGUGUCGACCAUGCGAGCCAGCAC-CGCCUACUAGA (SEQ ID NO:33); an miHDS.2 CUC-GAGUGAGCGCUCCCGGUCAUCAGCGAC-UAUUCCGUAAAGCCACAG AUGGGGAUAGUCGCUGAUGACCGG-GAUCGCCUACUAG (SEQ ID NO:2) or GCGU-UUAGUGAACCGUCAGAUGGUACCGU-UUAAACUCGAGUGAGCGC UCCCGGUCAUCAGCGACUAUUC-CGUAAAGCCACAGAUGGGGAUAGUCG CUGAUGACCGGGAUCGCCUACUAGAGCG-GCCGCCACAGCGGGGAGAUC CAGACAUGAUAA-GAUACAUU (SEQ ID NO:11); or an miHDS.5 CUC-GAGUGAGCGCUCCUCUUGUUUACGACGUGAUCU-GUAAAGCCACAG AUGGGAUUACGUCGUAAACAA-GAGGAACGCCUACUAGU (SEQ ID NO:3).

The present invention provides an isolated RNA duplex comprising a guide region of nucleic acid and a non-guide region of nucleic acid, wherein the guide region is at least 90% identical to CGACCAUGCGAGCCAGCA (miHDS.1 guide, SEQ ID NO:7), AGUCGCUGAUGACCGGGA (mi-HDS.2 guide, SEQ ID NO:8) or ACGUCGUAAACAA-GAGGA (miHDS.5 guide, SEQ ID NO:9) and the non-guide region is at least 80% complementary to the guide region. In certain embodiments, the isolated RNA duplex is between 19-30 base pairs in length. Certain embodiments include an expression cassette encoding the isolated nucleic acid described above. In certain embodiments the expression cassette further comprises a marker gene.

The present invention provides method of inducing RNA interference by administering to a subject a nucleic acid, an expression cassette, a vector, or a composition described herein.

The present invention provides a vector containing a U6 promoter operably linked to a nucleic acid encoding an miRNA. The predicted transcription start sites of constructs of the present invention are different from those used by researchers in the past. In certain embodiments of the present invention, the U6miRNA has an extended 5' end. If the 5' end is truncated to resemble the previous CMV-based strategy, silencing efficacy is severely reduced. The present invention also provides improved flanking sequences that show improved efficacy over natural miR-30 flanking sequences. The use of the present miRNA strategy appears to alleviate toxicity associated with traditional shRNA approaches. The miRNA strategy does not generally generate excessive amounts of RNAi as do U6shRNA approaches.

As used herein the term "stem sequence" is a sequence that is complementary to another sequence in the same molecule, where the two complementary strands anneal to form a duplex (e.g., the non-guide and guide regions). The duplex that is formed maybe fully complementary, or may be less than fully complementary, such as 99%, 98%, 97%, 96%, 95,%, 94%, 93%, 92%, 91%, 90%, 89%, 88%, 87%, 86%, 85%, 84%, 83%, 82%, 81%, 80%, 75%, or 70% complementary to each other. Further, in certain embodiments, one strand may contain more nucleotides than the other strand, allowing the formation of a side loop.

The present invention also provides vectors containing the expression cassettes described herein. Examples of appropriate vectors include adenoviral, lentiviral, adeno-associated viral (AAV), poliovirus, herpes simplex virus (HSV), or murine Maloney-based viral vectors. In one embodiment, the vector is an adeno-associated virus vector. These cassettes and vectors may be contained in a cell, such as a mammalian cell. A non-human mammal may contain the cassette or vector.

The present invention provides cells (such as a mammalian cell) containing the nucleic acid molecules, expression cassettes or vectors described herein. The present invention also provides a non-human mammal containing the nucleic acid molecules, expression cassettes or vectors described herein.

The present invention provides a nucleic acid, an expression cassette, a vector, or a composition as described herein for use in therapy, such as for treating a neurodegenerative disease.

The present invention provides an isolated RNAi molecule having a microRNA having an overhang at the 3' end. In certain embodiments, the overhang is a 2 to 5-nucleotide repeat. In certain embodiments, the overhang is a UU (SEQ ID NO:26), UUU (SEQ ID NO:27), UUUU (SEQ ID NO:28), CUU (SEQ ID NO:29), CUUU (SEQ ID NO:30) or CUUUU (SEQ ID NO:31) sequence. In certain embodiments, the microRNA is a naturally-occurring microRNA. In certain embodiments, microRNA is an artificial microRNA. In certain embodiments, the RNAi molecule produces a decreased level of off-target toxicity.

The present invention provides a method of inducing low-toxicity RNA interference by administering to a subject a nucleic acid, an expression cassette, a vector, or a composition as described herein. In certain embodiments, the expression cassette contains a polII promoter.

The present invention provides a method of inducing low-toxicity RNA interference by administering to a subject an expression cassette encoding a polII promoter operably linked to a nucleic acid encoding a miRNA. In certain embodiments, the miRNA comprises a 2- or 3-nucleotide 5' or 3'-overhang. In certain embodiments, the miRNA comprises a 2-nucleotide 3'-overhang. In certain embodiments, the miRNA is an artificial miRNA.

The present invention provides a method of treating a subject with a Huntington's Disease by administering to the subject a nucleic acid, an expression cassette, a vector, or a composition as described herein so as to treat the Huntington's Disease.

The present invention provides a method of suppressing the accumulation of huntingtin in a cell by introducing nucleic acid molecules (e.g., a ribonucleic acid (RNA)) described herein into the cell in an amount sufficient to suppress accumulation of huntingtin in the cell. In certain embodiments, the accumulation of huntingtin is suppressed by at least 10%. In certain embodiments, the accumulation of huntingtin is suppressed by at least 10%, 20%, 30%, 40%, 50%, 60%, 70%, 80%, 90% 95%, or 99%. In certain embodiments, the suppression of the accumulation of the protein is in an amount sufficient to cause a therapeutic effect, e.g., to reduce the formation of tangles.

The present invention provides a method of preventing cytotoxic effects of mutant huntingtin in a cell by introducing nucleic acid molecules (e.g., a ribonucleic acid (RNA)) described herein into the cell in an amount sufficient to suppress accumulation of huntingtin. In certain embodiments, the nucleic acid molecules prevents cytotoxic effects of huntingtin, e.g., in a neuronal cell.

The present invention provides a method to inhibit expression of a huntingtin gene in a cell by introducing a nucleic acid molecule (e.g., a ribonucleic acid (RNA)) described herein into the cell in an amount sufficient to inhibit expression of the huntingtin, and wherein the RNA inhibits expression of the huntingtin gene. In certain embodiments, the huntingtin is inhibited by at least 10%, 20%, 30%, 40%, 50%, 60%, 70%, 80%, 90% 95%, or 99%.

The present invention provides a method to inhibit expression of a huntingtin gene in a mammal (e.g., a human or a non-human mammal) by (a) providing a mammal containing a neuronal cell, wherein the neuronal cell contains the huntingtin gene and the neuronal cell is susceptible to RNA interference, and the huntingtin gene is expressed in the neuronal cell; and (b) contacting the mammal with a ribonucleic acid (RNA) or a vector described herein, thereby inhibiting expression of the huntingtin gene. In certain embodiments, the accumulation of huntingtin is suppressed by at least 10%. In certain embodiments, the huntingtin is inhibited by at least 10%, 20%, 30%, 40%, 50%, 60%, 70%, 80%, 90% 95%, or 99%. In certain embodiments, the cell is located in vivo in a mammal.

The present invention provides a viral vector comprising a promoter and a micro RNA (miRNA) shuttle containing an embedded siRNA specific for a target sequence. In certain embodiments, the promoter is an inducible promoter. In certain embodiments, the vector is an adenoviral, lentiviral, adeno-associated viral (AAV), poliovirus, HSV, or murine Maloney-based viral vector. In certain embodiments, the targeted sequence is a sequence associated with Huntington's Disease. The target sequence, in certain embodiments, is a sequence encoding huntingtin.

The present invention provides a method of preventing cytotoxic effects of neurodegenerative disease in a mammal in need thereof, by introducing the vector encoding a miRNA described herein into a cell in an amount sufficient to suppress accumulation of a protein associated with Huntington's Disease, and wherein the RNA prevents cytotoxic effects of Huntington's Disease (also referred to as HD, and the protein involved is huntingtin, also called htt).

The present invention also provides a method to inhibit expression of a protein associated with Huntington's Disease in a mammal in need thereof, by introducing the vector encoding a miRNA described herein into a cell in an amount sufficient to inhibit expression of the huntingtin protein, wherein the RNA inhibits expression of the huntingtin protein. The huntingtin protein is inhibited by at least 10%, 20%, 30%, 40%, 50%, 60%, 70%, 80%, 90% 95%, or 99%.

This invention relates to compounds, compositions, and methods useful for modulating Huntington's Disease gene expression using short interfering nucleic acid (siRNA) molecules. This invention also relates to compounds, compositions, and methods useful for modulating the expression and activity of other genes involved in pathways of HD gene expression and/or activity by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression HD genes. A siRNA molecule of the instant invention can be, e.g., chemically synthesized, expressed from a vector or enzymatically synthesized.

As used herein when a claim indicates an RNA "corresponding to" it is meant the RNA that has the same sequence as the DNA, except that uracil is substituted for thymine.

The present invention further provides a method of substantially silencing a target gene of interest or targeted allele for the gene of interest in order to provide a therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effects can be measured quantitatively by a physician or qualitatively by a patient afflicted with the disease state targeted by the siRNA. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect.

In one embodiment, the invention features a method for treating or preventing Huntington's Disease in a subject or organism comprising contacting the subject or organism with a siRNA of the invention under conditions suitable to modulate the expression of the HD gene in the subject or organism whereby the treatment or prevention of Huntington's Disease can be achieved. In one embodiment, the HD gene target comprises both HD allele (e.g., an allele comprising a trinucleotide (CAG) repeat expansion and a wild type allele). The siRNA molecule of the invention can be expressed from vectors as described herein or otherwise known in the art to target appropriate tissues or cells in the subject or organism.

In one embodiment, the invention features a method for treating or preventing Huntington's Disease in a subject or organism comprising, contacting the subject or organism with a siRNA molecule of the invention via local administration to relevant tissues or cells, such as brain cells and tissues (e.g., basal ganglia, striatum, or cortex), for example, by administration of vectors or expression cassettes of the invention that provide siRNA molecules of the invention to relevant cells (e.g., basal ganglia, striatum, or cortex). In one embodiment, the siRNA, vector, or expression cassette is administered to the subject or organism by stereotactic or convection enhanced delivery to the brain. For example, U.S. Pat. No. 5,720,720 provides methods and devices useful for stereotactic and convection enhanced delivery of reagents to the brain. Such methods and devices can be readily used for the delivery of siRNAs, vectors, or expression cassettes of the invention to a subject or organism, and is U.S. Pat. No. 5,720,720 is incorporated by reference herein in its entirety. US Patent Application Nos. 2002/0141980; 2002/0114780; and 2002/0187127 all provide methods and devices useful for stereotactic and convection enhanced delivery of reagents that can be readily adapted for delivery of siRNAs, vectors, or expression cassettes of the invention to a subject or organism, and are incorporated by reference herein in their entirety. Particular devices that may be useful in delivering siRNAs, vectors, or expression cassettes of the invention to a subject or organism are for example described in US Patent Application No. 2004/0162255, which is incorporated by reference herein in its entirety. The siRNA molecule of the invention can be expressed from vectors as described herein or otherwise known in the art to target appropriate tissues or cells in the subject or organism.

Methods of delivery of viral vectors include, but are not limited to, intra-arterial, intra-muscular, intravenous, intranasal and oral routes. Generally, AAV virions may be introduced into cells of the CNS using either in vivo or in vitro transduction techniques. If transduced in vitro, the desired recipient cell will be removed from the subject, transduced with AAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, for in vivo delivery, AAV virions are formulated into pharmaceutical compositions and will generally be administered parenterally, e.g., by intramuscular injection directly into skeletal or cardiac muscle or by injection into the CNS.

In one embodiment, viral vectors of the invention are delivered to the CNS via convection-enhanced delivery (CED) systems that can efficiently deliver viral vectors, e.g., AAV, over large regions of a subject's brain (e.g., striatum and/or cortex). As described in detail and exemplified below, these methods are suitable for a variety of viral vectors, for instance AAV vectors carrying therapeutic genes (e.g., siRNAs).

Any convection-enhanced delivery device may be appropriate for delivery of viral vectors. In one embodiment, the device is an osmotic pump or an infusion pump. Both osmotic and infusion pumps are commercially available from a variety of suppliers, for example Alzet Corporation, Hamilton Corporation, Aiza, Inc., Palo Alto, Calif.). Typically, a viral vector is delivered via CED devices as follows. A catheter, cannula or other injection device is inserted into CNS tissue in the chosen subject. In view of the teachings herein, one of skill in the art could readily determine which general area of the CNS is an appropriate target. For example, when delivering AAV vector encoding a therapeutic gene to treat HD, the striatum is a suitable area of the brain to target. Stereotactic maps and positioning devices are available, for example from ASI Instruments, Warren, Mich. Positioning may also be conducted by using anatomical maps obtained by CT and/or MRI imaging of the subject's brain to help guide the injection device to the chosen target. Moreover, because the methods described herein can be practiced such that relatively large areas of the brain take up the viral vectors, fewer infusion cannula are needed. Since surgical complications are related to the number of penetrations, the methods described herein also serve to reduce the side effects seen with conventional delivery techniques.

In one embodiment, pharmaceutical compositions will comprise sufficient genetic material to produce a therapeutically effective amount of the siRNA of interest, i.e., an amount sufficient to reduce or ameliorate symptoms of the disease state in question or an amount sufficient to confer the desired benefit. The pharmaceutical compositions may also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

It should be understood that more than one transgene could be expressed by the delivered viral vector. Alternatively, separate vectors, each expressing one or more different transgenes, can also be delivered to the CNS as described herein. Furthermore, it is also intended that the viral vectors delivered by the methods of the present invention be combined with other suitable compositions and therapies.

The present invention further provides an miRNA or shRNA, an expression cassette and/or a vector as described herein for use in medical treatment or diagnosis.

The present invention provides the use of an miRNA or shRNA, an expression cassette and/or a vector as described herein to prepare a medicament useful for treating a condition amenable to RNAi in an animal, e.g., useful for treating Huntington's Disease.

The present invention also provides a nucleic acid, expression cassette, vector, or composition of the invention for use in therapy.

The present invention also provides a nucleic acid, expression cassette, vector, or composition of the invention for treating, e.g., for use in the prophylactic or therapeutic treatment of, Huntington's Disease.

BRIEF DESCRIPTION OF THE FIGURES

FIG. 3a discloses SEQ ID NOs: 208-210, respectively, in order of appearance. (b) Plasmids expressing artificial miRNAs, harboring the indicated siRNA sequences, were transfected into HEK293 cells, and QPCR analysis was performed 24 h later to measure endogenous htt mRNA levels. U6 (promoter-only) and HD2.4 (a previously published htt RNAi sequence) serve as the negative and positive controls respectively. Results are shown as mean±SEM (N=6, * indicates P<0.001, relative to U6).

FIG. 7 discloses SEQ ID NOS: 10, 218, 219 and 210, respectively, in order of appearance.

FIG. 8 discloses SEQ ID NOS: 11, 220, 221 and 213, respectively, in order of appearance.

DETAILED DESCRIPTION OF THE INVENTION

Figure 1:
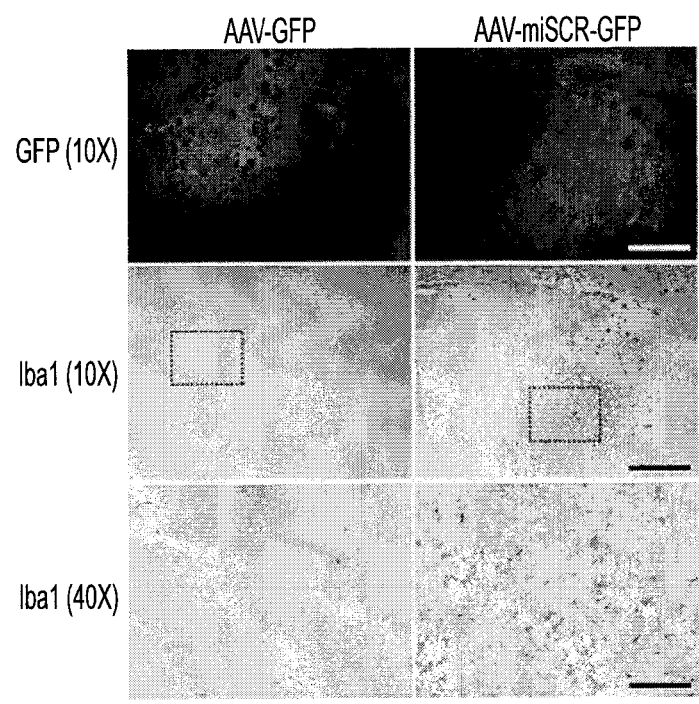
FIG. 1. The artificial miRNA, miSCR, causes neurotoxicity in mouse brain. Wild-type mice were injected into the striatum with AAV-GFP (expresses GFP only) or AAV-miSCR-GFP (expresses both the artificial miRNA and GFP), and histological analyses were performed on brains harvested at 6 months post-treatment. Photomicrographs representing GFP autofluorescence and immunohistochemical staining of Iba1-positive microglia are shown. Scale bars=200 and 50 μm for 10× and 40× images respectively.

RNA Interference (RNAi) is a process of gene regulation mediated by small dsRNAs. RNAi is used as a common biological tool to study gene function, and is under investigation as a therapeutic to treat various diseases. RNAi delivery or expression can be through the administration of exogenous siRNAs (transient gene silencing) or through the administration of vectors expressing stem-loop RNAs (persistent gene silencing). The absolute specificity of RNAi is questionable. Issues that must be addressed include cellular responses to dsRNA (IFN-b, PKR, OAS1) and off-target effects due to saturation of RNAi machinery or via partial complementarity with unintended mRNAs. There is an ongoing need for optimizing RNAi vectors and potentially developing tissue-specific and regulated expression strategies The use of RNAi as a therapeutic is dependant upon the elucidation of several factors including i) the delivery and persistence of the RNAi construct for effective silencing of the target gene sequence; ii) the design of the siRNA in order to achieve effective knock down or gene suppression of the target sequence, and iii) the optimal siRNA expression system (snRNA or miRNA) for delivery of the therapeutic siRNA. While many studies have evaluated the use of RNAi delivered as chemically synthesized oligonucleotide structures, for many clinical conditions and disease states such as Huntington's Disease, it is believed that to achieve therapeutic benefit there is a need for long term and or persistent high level expression of the therapeutic siRNA as achieved by endogenous production of expressed siRNA. To date, shRNA- and artificial miRNA-based strategies have been compared with conflicting results. The therapeutic utility of expressed RNAi is unresolved due to safety concerns as a result of off target toxicity arising from cellular responses to dsRNA (IFN-b, PKR, OAS1), saturation of RNAi machinery or silencing of off targets via partial complementarity with unintended mRNAs. Thus, there is an on-going need for optimizing expressed RNAi vectors that are safe and effective.

shRNAs are comprised of stem-loop structures which are designed to contain a 5' flanking region, siRNA region segments, a loop region, a 3' siRNA region and a 3' flanking region. Most RNAi expression strategies have utilized short-hairpin RNAs (shRNAs) driven by strong polIII-based promoters. Many shRNAs have demonstrated effective knock down of the target sequences in vitro as well as in vivo, however, some shRNAs which demonstrated effective knock down of the target gene were also found to have toxicity in vivo. A recently discovered alternative approach is the use of artificial miRNAs (pri-miRNA scaffolds shuttling siRNA sequences) as RNAi vectors. Artificial miRNAs more naturally resemble endogenous RNAi substrates and are more amenable to Pol-II transcription (e.g., allowing tissue-specific expression of RNAi) and polycistronic strategies (e.g., allowing delivery of multiple siRNA sequences). To date the efficacy of miRNA based vector systems compared to shRNA has been confounded by conflicting results. Importantly, the question of off-target toxicity produced by the two systems has not been evaluated.

An important consideration for development of expressed siRNA is the concept of "dosing" the host cell with the expressed siRNA construct. "Dosing" for an expressed siRNA in the context of the present invention refers to and can be dependant on the delivery vehicle (e.g., viral or nonviral), the relative amounts or concentration of the delivery vehicle, and the strength and specificity of the promoter utilized to drive the expression of the siRNA sequence.

The inventors have developed artificial miRNA shuttle vectors that incorporate the stem loop sequences contained in shRNAs within modifications of a naturally occurring human microRNA 30 sequence or mi30 sequence that serve to shuttle these small interfering RNA (siRNA) sequences. See, e.g., PCT Publication WO 2008/150897, which is incorporated by reference herein.

MicroRNA Shuttles for RNAi miRNAs are small cellular RNAs (~22 nt) that are processed from precursor stem loop transcripts. Known miRNA stem loops can be modified to contain RNAi sequences specific for genes of interest. miRNA molecules can be preferable over shRNA molecules because miRNAs are endogenously expressed. Therefore, miRNA molecules are unlikely to induce dsRNA-responsive interferon pathways, they are processed more efficiently than shRNAs, and they have been shown to silence 80% more effectively.

Also, the promoter roles are different for miRNA molecules as compared to shRNA molecules. Tissue-specific, inducible expression of shRNAs involves truncation of polII promoters to the transcription start site. In contrast, miRNAs can be expressed from any polII promoter because the transcription start and stop sites can be relatively arbitrary.

Treatment of Huntington's Disease

The dominant polyglutamine expansion diseases, which include Spinocerebellar ataxia type 1 (SCA1) and Huntington's disease (HD), are progressive, untreatable neurodegenerative disorders. In inducible mouse models HD, repression of mutant allele expression improves disease phenotypes. Thus, therapies designed to inhibit disease gene expression would be beneficial. The present invention provides methods of using RNAi in vivo to treat Huntington's Disease. "Treating" as used herein refers to ameliorating at least one symptom of, curing and/or preventing the development of a disease or a condition.

In certain embodiment of the invention, RNAi molecules are employed to inhibit expression of a target gene. By "inhibit expression" is meant to reduce, diminish or suppress expression of a target gene. Expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when an RNAi molecule initiates the inhibition or degradation of the mRNA transcribed from a gene of interest in a sequence-specific manner via RNA interference, thereby preventing translation of the gene's product.

The reference to siRNAs herein is meant to include shRNAs and other small RNAs that can or are capable of modulating the expression of a targeted gene, e.g., the HD gene, for example via RNA interference. Such small RNAs include without limitation, shRNAs and miroRNAs (miRNAs).

Disclosed herein is a strategy that results in substantial silencing of targeted genes via RNAi. Use of this strategy results in markedly diminished in vitro and in vivo expression of targeted genes. This strategy is useful in reducing expression of targeted genes in order to model biological processes or to provide therapy for human diseases. For example, this strategy can be applied to Huntington's Disease. As used herein the term "substantial silencing" means that the mRNA of the targeted gene is inhibited and/or degraded by the presence of the introduced siRNA, such that expression of the targeted gene is reduced by about 10% to 100% as compared to the level of expression seen when the siRNA is not present. Generally, when an gene is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the siRNA is not present. As used herein the term "substantially normal activity" means the level of expression of a gene when an siRNA has not been introduced to a cell.

Huntington disease (HD) is a strong candidate for siRNA-based therapy. HD is caused by CAG repeat expansions that encode polyQ in the disease protein. PolyQ expansion confers a dominant toxic property on the mutant protein that is associated with aberrant accumulation of the disease protein in neurons. HD is progressive, ultimately fatal disorders that typically begin in adulthood. Expansion of the CAG repeat/polyQ domain confers upon the encoded protein a dominant toxic property. Thus, as a therapeutic strategy, efforts to lower expression of the mutant gene product prior to cell death could be highly beneficial to patients.

RNA Interference (RNAi) Molecules

An "RNA interference," "RNAi," "small interfering RNA" or "short interfering RNA" or "siRNA" or "short hairpin RNA" or "shRNA" molecule, or "miRNA" is a RNA duplex of nucleotides that is targeted to a nucleic acid sequence of interest, for example, huntingtin (htt). As used herein, the term "siRNA" is a generic term that encompasses the subset of shRNAs and miRNAs. An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding ataxin-1 or huntingtin. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24 or 25 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional siRNAs. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional siRNAs. "Artificial miRNA" or an "artificial miRNA shuttle vector," as used herein interchangably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (~35 nucleotides upstream and ~40 nucleotides downstream) arise from restriction enzyme sites within the multiple cloning site of the siRNA. As used herein the term "miRNA" encompasses both the naturally occurring miRNA sequences as well as artificially generated miRNA shuttle vectors.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

"Off-target toxicity" refers to deleterious, undesirable, or unintended phenotypic changes of a host cell that expresses or contains an siRNA. Off-target toxicity may result in loss of desirable function, gain of non-desirable function, or even death at the cellular or organismal level. Off-target toxicity may occur immediately upon expression of the siRNA or may occur gradually over time. Off-target toxicity may occur as a direct result of the expression siRNA or may occur as a result of induction of host immune response to the cell expressing the siRNA. Without wishing to be bound by theory, off-target toxicity is postulated to arise from high levels or overabundance of RNAi substrates within the cell. These overabundant or overexpressed RNAi substrates, including without limitation pre- or pri RNAi substrates as well as overabundant mature antisense-RNAs, may compete for endogenous RNAi machinery, thus disrupting natural miRNA biogenesis and function. Off-target toxicity may also arise from an increased likelihood of silencing of unintended mRNAs (i.e., off-target) due to partial complementarity of the sequence. Off target toxicity may also occur from improper strand biasing of a non-guide region such that there is preferential loading of the non-guide region over the targeted or guide region of the RNAi. Off-target toxicity may also arise from stimulation of cellular responses to dsRNAs which include dsRNA (IFN-b, PKR, OAS1). "Decreased off target toxicity" refers to a decrease, reduction, abrogation or attenuation in off target toxicity such that the therapeutic effect is more beneficial to the host than the toxicity is limiting or detrimental as measured by an improved duration or quality of life or an improved sign or symptom of a disease or condition being targeted by the siRNA. "Limited off target toxicity" or "low off target toxicity" is used to refer to an unintended undesirable phenotypic changes to a cell or organism, whether detectable or not, that does not preclude or outweigh or limit the therapeutic benefit to the host treated with the siRNA and may be considered a "side effect" of the therapy. Decreased or limited off target toxicity may be determined or inferred by comparing the in vitro analysis such as Northern blot or QPCR for the levels of siRNA substrates or the in vivo effects comparing an equivalent shRNA vector to the miRNA shuttle vector of the present invention.

"Knock-down," "knock-down technology" refers to a technique of gene silencing in which the expression of a target gene is reduced as compared to the gene expression prior to the introduction of the siRNA, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where siRNA molecules have not been administered). Knock-down of gene expression can be directed by the use of dsRNAs or siRNAs.

"RNA interference (RNAi)" is the process of sequence-specific, post-transcriptional gene silencing initiated by siRNA. During RNAi, siRNA induces degradation of target mRNA with consequent sequence-specific inhibition of gene expression.

According to a method of the present invention, the expression of huntingtin can be modified via RNAi. For example, the accumulation of huntingtin can be suppressed in a cell. The term "suppressing" refers to the diminution, reduction or elimination in the number or amount of transcripts present in a particular cell. For example, the accumulation of mRNA encoding huntingtin can be suppressed in a cell by RNA interference (RNAi), e.g., the gene is silenced by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

A mutant protein refers to the protein encoded by a gene having a mutation, e.g., a missense or nonsense mutation in huntingtin. A mutant huntingtin may be disease-causing, i.e., may lead to a disease associated with the presence of huntingtin in an animal having either one or two mutant allele(s).

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single-stranded or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid nucleic acid molecules and compositions containing those molecules. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized.

In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

A "transgene" refers to a gene that has been introduced into the genome by transformation. Transgenes include, for example, DNA that is either heterologous or homologous to the DNA of a particular cell to be transformed. Additionally, transgenes may include native genes inserted into a non-native organism, or chimeric genes.

The term "endogenous gene" refers to a native gene in its natural location in the genome of an organism.

The terms "protein," "peptide" and "polypeptide" are used interchangeably herein.

"Wild-type" refers to the normal gene or organism found in nature.

"Genome" refers to the complete genetic material of an organism.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an siRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence," i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The term "open reading frame" (ORF) refers to the sequence between translation initiation and termination codons of a coding sequence. The terms "initiation codon" and "termination codon" refer to a unit of three adjacent nucleotides (a 'codon') in a coding sequence that specifies initiation and chain termination, respectively, of protein synthesis (mRNA translation).

"Functional RNA" refers to sense RNA, antisense RNA, ribozyme RNA, siRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell.

"cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted herein, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

"Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Chromosomally-integrated" refers to the integration of a foreign gene or nucleic acid construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g. BLASTN for nucleotide sequences) can be used. The BLASTN program (for nucleotide sequences) uses as defaults a wordlength (W) of 11, an expectation (E) of 10, a cutoff of 100, M=5, N=−4, and a comparison of both strands. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide matches and an identical percent sequence identity when compared to the corresponding alignment generated by the preferred program.

(c) As used herein, "sequence identity" or "identity" in the context of two nucleic acid sequences makes reference to a specified percentage of nucleotides in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted herein, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The Tm is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the Tm can be approximated from the equation: Tm 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point (Tm) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell 2001, for a description of SSC buffer). Often, a high stringency wash is preceded by a low stringency wash to remove background probe signal. For short nucleic acid sequences (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Very stringent conditions are selected to be equal to the Tm for a particular nucleic acid molecule.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., E. coli) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

The siRNAs of the present invention can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. The RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding a siRNA, the nucleic acid molecules of the invention include double-stranded interfering RNA molecules, which are also useful to inhibit expression of a target gene.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from a source by chemical means, e.g., by the use of restriction endonucleases, so that it can be further manipulated, e.g., amplified, for use in the invention, by the methodology of genetic engineering. "Recombinant DNA" includes completely synthetic DNA sequences, semi-synthetic DNA sequences, DNA sequences isolated from biological sources, and DNA sequences derived from RNA, as well as mixtures thereof.

Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585, 362.

As discussed herein, a "transfected" "or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell," comprises a cell and an expression vector for expressing the exogenous nucleic acid material. The genetically modified cells are suitable for administration to a mammalian recipient, where they replace the endogenous cells of the recipient. Thus, the preferred genetically modified cells are non-immortalized and are non-tumorigenic.

According to one embodiment, the cells are transfected or otherwise genetically modified ex vivo. The cells are isolated from a mammal (preferably a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into an anti-sense RNA, a siRNA, as well as a "heterologous gene" (i.e., a gene encoding a protein that is not expressed or is expressed at biologically insignificant levels in a naturally-occurring cell of the same type). To illustrate, a synthetic or natural gene encoding human erythropoietin (EPO) would be considered "exogenous nucleic acid material" with respect to human peritoneal mesothelial cells since the latter cells do not naturally express EPO. Still another example of "exogenous nucleic acid material" is the introduction of only part of a gene to create a recombinant gene, such as combining an regulatable promoter with an endogenous coding sequence via homologous recombination.

The condition amenable to gene inhibition therapy may be a prophylactic process, i.e., a process for preventing disease or an undesired medical condition. Thus, the instant invention embraces a system for delivering siRNA that has a prophylactic function (i.e., a prophylactic agent) to the mammalian recipient.

Methods for Introducing the Expression Cassettes of the Invention into Cells

The inhibitory nucleic acid material (e.g., an expression cassette encoding siRNA directed to a gene of interest) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the siRNA together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of siRNA generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a siRNA sequence that are in the cell.

In addition to at least one promoter and at least one heterologous nucleic acid sequence encoding the siRNA, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the siRNA(s), the other vector containing a selection gene. The selection of a suitable promoter, enhancer, selection gene, and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest.

The instant invention also provides methods for genetically modifying cells of a mammalian recipient in vivo. According to one embodiment, the method comprises introducing an expression vector for expressing a siRNA sequence in cells of the mammalian recipient in situ by, for example, injecting the vector into the recipient.

Delivery Vehicles for the Expression Cassettes of the Invention

Delivery of compounds into tissues and across the blood-brain barrier can be limited by the size and biochemical properties of the compounds. Currently, efficient delivery of compounds into cells in vivo can be achieved only when the molecules are small (usually less than 600 Daltons). Gene transfer for the correction of inborn errors of metabolism and neurodegenerative diseases of the central nervous system (CNS), and for the treatment of cancer has been accomplished with recombinant adenoviral vectors.

The selection and optimization of a particular expression vector for expressing a specific siRNA in a cell can be accomplished by obtaining the nucleic acid sequence of the siRNA, possibly with one or more appropriate control regions (e.g., promoter, insertion sequence); preparing a vector construct comprising the vector into which is inserted the nucleic acid sequence encoding the siRNA; transfecting or transducing cultured cells in vitro with the vector construct; and determining whether the siRNA is present in the cultured cells.

Vectors for cell gene therapy include viruses, such as replication-deficient viruses (described in detail below). Exemplary viral vectors are derived from Harvey Sarcoma virus, ROUS Sarcoma virus, (MPSV), Moloney murine leukemia virus and DNA viruses (e.g., adenovirus).

Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are well known in the art.

An advantage of using retroviruses for gene therapy is that the viruses insert the nucleic acid sequence encoding the siRNA into the host cell genome, thereby permitting the nucleic acid sequence encoding the siRNA to be passed on to the progeny of the cell when it divides. Promoter sequences in the LTR region have can enhance expression of an inserted coding sequence in a variety of cell types. Some disadvantages of using a retrovirus expression vector are (1) insertional mutagenesis, i.e., the insertion of the nucleic acid sequence encoding the siRNA into an undesirable position in the target cell genome which, for example, leads to unregulated cell growth and (2) the need for target cell proliferation in order for the nucleic acid sequence encoding the siRNA carried by the vector to be integrated into the target genome.

Another viral candidate useful as an expression vector for transformation of cells is the adenovirus, a double-stranded DNA virus. The adenovirus is infective in a wide range of cell types, including, for example, muscle and endothelial cells.

Adenoviruses (Ad) are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ. In addition, the ability of the adenovirus vector to accomplish in situ tumor transduction has allowed the development of a variety of anticancer gene therapy methods for non-disseminated disease. In these methods, vector containment favors tumor cell-specific transduction.

Like the retrovirus, the adenovirus genome is adaptable for use as an expression vector for gene therapy, i.e., by removing the genetic information that controls production of the virus itself. Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Most adenovirus vectors are based on the adenovirus type 5 (Ad5) backbone in which an expression cassette containing the nucleic acid sequence of interest has been introduced in place of the early region 1 (E1) or early region 3 (E3). Viruses in which E1 has been deleted are defective for replication and are propagated in human complementation cells (e.g., 293 or 911 cells), which supply the missing gene E1 and pIX in trans.

In one embodiment of the present invention, one will desire to generate siRNA in a brain cell or brain tissue. A suitable vector for this application is an FIV vector or an AAV vector. For example, one may use AAV5. Also, one may apply poliovirus or HSV vectors.

Application of siRNA is generally accomplished by transfection of synthetic siRNAs, in vitro synthesized RNAs, or plasmids expressing shRNAs or miRNAs. More recently, viruses have been employed for in vitro studies and to generate transgenic mouse knock-downs of targeted genes. Recombinant adenovirus, adeno-associated virus (AAV) and feline immunodeficiency virus (FIV) can be used to deliver genes in vitro and in vivo. Each has its own advantages and disadvantages. Adenoviruses are double stranded DNA viruses with large genomes (36 kb) and have been engineered by my laboratory and others to accommodate expression cassettes in distinct regions.

Adeno-associated viruses have encapsidated genomes, similar to Ad, but are smaller in size and packaging capacity (~30 nm vs. ~100 nm; packaging limit of ~4.5 kb). AAV contain single stranded DNA genomes of the + or the − strand. Eight serotypes of AAV (1-8) have been studied extensively, three of which have been evaluated in the brain. An important consideration for the present application is that AAV5 transduces striatal and cortical neurons, and is not associated with any known pathologies.

Adeno associated virus (AAV) is a small nonpathogenic virus of the parvoviridae family. AAV is distinct from the other members of this family by its dependence upon a helper virus for replication. In the absence of a helper virus, AAV may integrate in a locus specific manner into the q-arm of chromosome 19. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

Further provided by this invention are chimeric viruses where AAV can be combined with herpes virus, herpes virus amplicons, baculovirus or other viruses to achieve a desired tropism associated with another virus. For example, the AAV4 ITRs could be inserted in the herpes virus and cells could be infected. Post-infection, the ITRs of AAV4 could be acted on by AAV4 rep provided in the system or in a separate vehicle to rescue AAV4 from the genome. Therefore, the cellular tropism of the herpes simplex virus can be combined with AAV4 rep mediated targeted integration. Other viruses that could be utilized to construct chimeric viruses include lentivirus, retrovirus, pseudotyped retroviral vectors, and adenoviral vectors.

Also provided by this invention are variant AAV vectors. For example, the sequence of a native AAV, such as AAV5, can be modified at individual nucleotides. The present invention includes native and mutant AAV vectors. The present invention further includes all AAV serotypes.

FIV is an enveloped virus with a strong safety profile in humans; individuals bitten or scratched by FIV-infected cats do not seroconvert and have not been reported to show any signs of disease. Like AAV, FIV provides lasting transgene expression in mouse and nonhuman primate neurons, and transduction can be directed to different cell types by pseudotyping, the process of exchanging the virus's native envelope for an envelope from another virus.

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene silencing therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (Promega®, Madison, Wis.). However, the efficiency of transfection by these methods is highly dependent on the nature of the target cell and accordingly, the conditions for optimal transfection of nucleic acids into cells using the herein-mentioned procedures must be optimized. Such optimization is within the scope of one of ordinary skill in the art without the need for undue experimentation.

Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art. As used herein, the term "therapeutic siRNA" refers to any siRNA that has a beneficial effect on the recipient. Thus, "therapeutic siRNA" embraces both therapeutic and prophylactic siRNA.

Administration of siRNA may be accomplished through the administration of the nucleic acid molecule encoding the siRNA. Pharmaceutical formulations, dosages and routes of administration for nucleic acids are generally known.

The present invention envisions treating Huntington's disease in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the brain. Alternatively the therapeutic agent may be introduced intrathecally for brain and spinal cord conditions. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0. saline solutions and water.

The invention will now be illustrated by the following non-limiting Example.

Example 1

Rational Design of Therapeutic siRNAs: Minimizing Off-Targeting Potential to Improve the Safety of RNAi Therapy for Huntington's Disease RNA interference (RNAi) provides an approach for the treatment of many human diseases. However, the safety of RNAi-based therapies can be hampered by the ability of small inhibitory RNAs (siRNAs) to bind to unintended mRNAs and reduce their expression, an effect known as off-target gene silencing. Off-targeting primarily occurs when the seed region (nucleotides 2-8 of the small RNA) pairs with sequences in 3'-UTRs of unintended mRNAs and directs translational repression and destabilization of those transcripts. To date, most therapeutic RNAi sequences are selected primarily for gene silencing efficacy, and later evaluated for safety. Here, in designing siRNAs to treat Huntington's disease (HD), a dominant neurodegenerative disorder, we prioritized selection of sequences with minimal off-targeting potentials (i.e. those with a scarcity of seed complements within all known human 3'-UTRs). We identified new promising therapeutic candidate sequences which show potent silencing in cell culture and mouse brain. Furthermore, we present microarray data demonstrating that off-targeting is significantly minimized by using siRNAs that contain "safe" seeds, an important strategy to consider during pre-clinical development of RNAi-based therapeutics.

RNAi directs sequence-specific gene silencing by double-stranded RNA (dsRNA) which is processed into functional small inhibitory RNAs (~21 nt). In nature, RNAi for gene regulation occurs primarily via small RNAs known as microRNAs (miRNAs). Mature microRNAs (~19-25 nts) are processed from larger primary miRNA transcripts (pri-miRNAs) which contain stem-loop regions. Via a series of processing events catalyzed by the ribonucleases, Drosha and Dicer, the miRNA duplex region is liberated, and a single strand (the antisense "guide" strand) is then incorporated into the RNA Induced Silencing Complex (RISC), thus generating a functional complex capable of base-pairing with and silencing transcripts by various means depending on the degree of complementarity. A high-degree of base-pairing causes target transcript cleavage, whereas imperfect binding (typically to transcript 3'-UTRs) induces the canonical miRNA-based repression mechanism resulting in translational repression and mRNA destabilization. Indeed for the latter, pairing via the seed region with as few as 6-7 bp may be sufficient to trigger silencing.

Elucidating the mechanisms involved in endogenous miRNA biogenesis and gene silencing has enabled scientists to devise strategies to co-opt the cellular RNAi machinery and direct silencing of virtually any gene of interest using siRNAs, short-hairpin RNAs (shRNAs), and artificial miRNAs; the latter two represent expressed stem-loop transcripts which release siRNAs upon processing. siRNAs are generally designed with the guide strand exhibiting perfect complementarity to the intended mRNA target to promote cleavage. This potent gene silencing approach has become a powerful molecular tool to study gene function and is being developed as a therapeutic strategy to suppress disease-causing genes. The utility of siRNA-based technologies as biological or clinical interventions is largely limited by our abilities to design effective and specific inhibitory RNAs and to introduce them into target cells or tissues. A major consideration for gene silencing applications is specificity, and there is mounting evidence supporting that siRNAs bind to and repress unintended mRNAs, an effect known as off-target silencing. Off-targeting primarily occurs when the seed region pairs with 3'-UTR sequences in mRNAs and directs translational repression and destabilization of those transcripts. Recent data supports that seed-based off-targeting may induce toxic phenotypes. It has been observed that the magnitude of siRNA off-targeting is directly related to the frequency of seed complements (hexamers) present in the 3'-UTRome. By evaluating subsets of siRNAs with differing off-targeting potentials (low, medium and high; predicted based on hexamer distributions in human 3'-UTRs), they discovered that siRNAs in the low subset had significantly diminished off-target signatures (based on microarray data) and less adverse effects on cell viability as compared to siRNAs in the medium and high subsets. These observations established the importance of considering seed complement hexamer distributions as a key criterion for designing highly specific siRNAs, and some siRNA design tools have since incorporated seed-specificity guidelines into their algorithms. However, most publically available algorithms remain strongly biased for gene silencing efficacy over specificity, and thus, very few candidate siRNAs actually contain seeds with low off-targeting potentials. This is revealed in a literature survey of siRNAs under therapeutic development; only 7 of 80 recently published siRNAs with therapeutic relevance (Table 6) could be classified into the low off-targeting subgroup. This is problematic as siRNAs move into early-stage clinical trials. While potency-based design is rational, current publicly available tools identify only a fraction of the functional siRNAs for a given target transcript, and often times, highly functional siRNAs do not satisfy several design rules. For these reasons, and in the interest of improving the safety profile of therapeutic RNAi, the inventors hypothesized that a siRNA design scheme prioritizing specificity yet promoting efficacy would yield candidate siRNA sequences with minimal off-targeting potential and a robust capacity for potent gene silencing.

Results

Some Artificial miRNAs Induce Sequence-Specific Toxicity

Previous studies from our laboratory and others' have demonstrated the potential of RNAi therapeutics for treating Huntington's disease (HD), a dominant neurodegenerative disease caused by a CAG repeat expansion which confers a toxic gain-of-function to the resulting huntingtin (htt) protein. In several rodent models for HD, viral-based expression of RNAi hairpins targeting mutant htt mRNA in brain reduced transcript and protein levels by ~50-70%, improving behavioral and neuropathological phenotypes. Following these proof-of-concept successes, the inventors initiated studies to evaluate and optimize the safety of RNAi-based therapeutics. The inventors compared the silencing efficacy and safety of shRNA and artificial miRNA expression vectors in vitro and in vivo. The inventors found that shRNAs are more potent but induce toxicity in cell cultures and in mouse brain, whereas artificial miRNAs are expressed at tolerably lower levels and display better safety profiles while maintaining potent gene silencing. Since this discovery, the inventors have tested several artificial miRNA sequences in mouse brain using recombinant adeno-associated viruses (AAV serotype 2/1) for delivery, and in some instances, have observed sequence-dependent toxicity. For example, one artificial miRNA targeting htt (miHD-Ex1) caused a high incidence of seizures and morbidity in treated mice (data not shown); of note, this toxic phenotype was not a consequence of htt knockdown, as it has been previously reported that silencing endogenous htt in mouse brain is tolerated. In another instance, a non-targeted artificial miRNA (miSCR, a scrambled control) induced evident neurotoxicity as indicated by increased staining for Iba1, a marker for resting and reactive microgila, in treated regions of the striatum (FIG. 1). Together, these data suggest that although artificial miRNAs show improved safety over shRNAs, sequence-dependent toxicity remains a concern. The inventors therefore explored supplemental means to improve safety by employing a rational siRNA design scheme intended to minimize the probability for off-target silencing.

Figure 2:
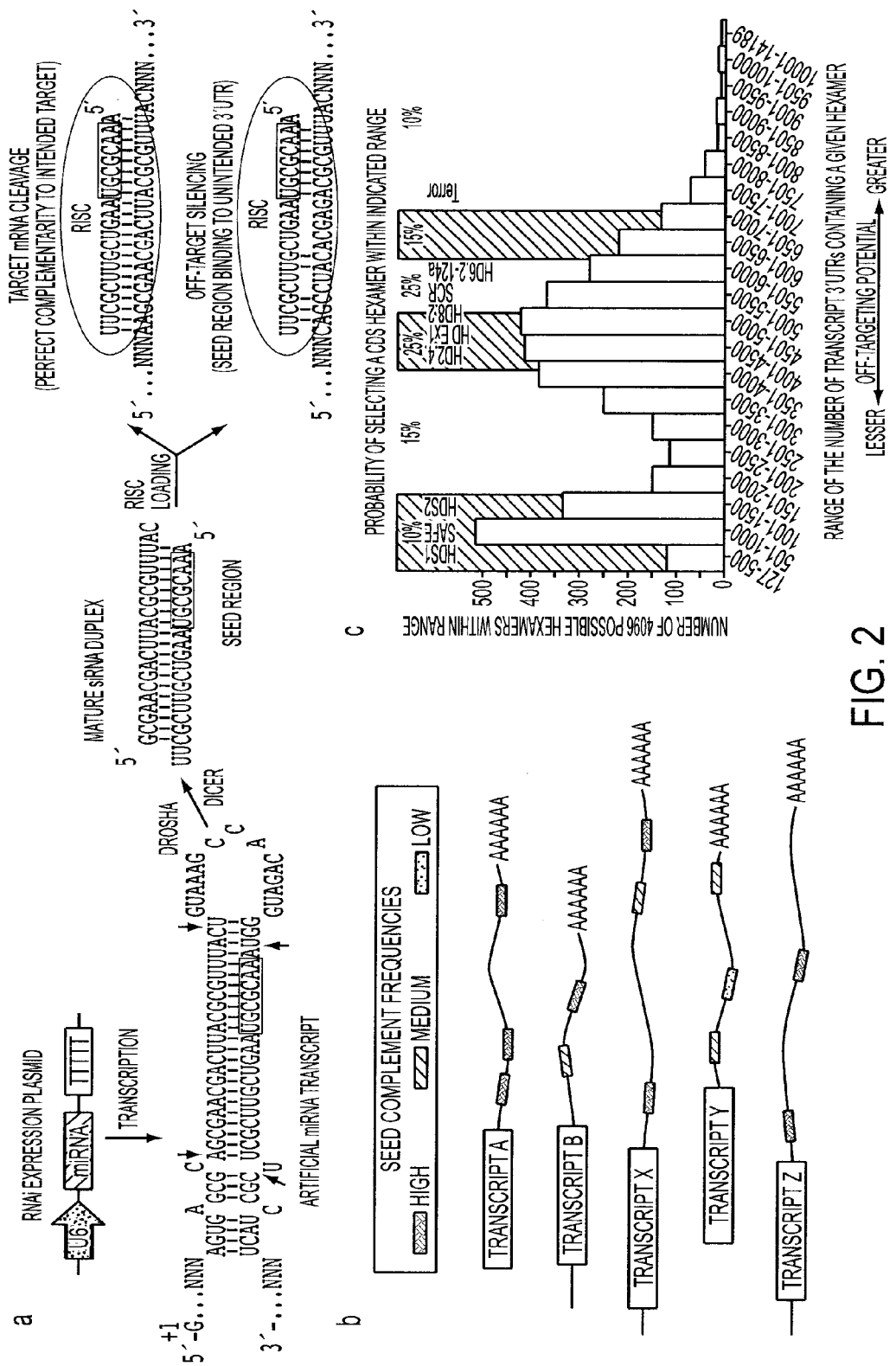
FIG. 2. Overview of seed-related off-targeting: mechanism and probabilities. (a) Diagram depicting the expression and processing of an artificial miRNA (SEQ ID NO: 203) to produce the mature siRNA duplex (SEQ ID NOs: 204 and 205, respectively, in order of appearance). The antisense guide strand is loaded into RISC and may direct on-target silencing (intended) (SEQ ID NOs: 205 and 206, respectively, in order of appearance) and off-target silencing (unintended) (SEQ ID NOs: 205 and 207, respectively, in order of appearance). (b) Cartoon highlighting the relationship between the frequencies of seed complement binding sites in the 3'-UTRome and the off-targeting potential for siRNAs. (c) The number of human mRNA 3'-UTRs containing a given hexamer was determined for all of the 4096 possible hexamers and a binned distribution is shown. The probabilities that randomly selected siRNAs targeting human coding sequence (CDS) will contain seed complements in a given range (white and grey shading) are also presented. For example, there is only a 10% chance that a randomly selected siRNA contains a seed complement for a hexamer present in ~1500 human 3'-UTRs or less. Note: the sequences tested in this manuscript are placed above their respective ranges.
Figure 3:
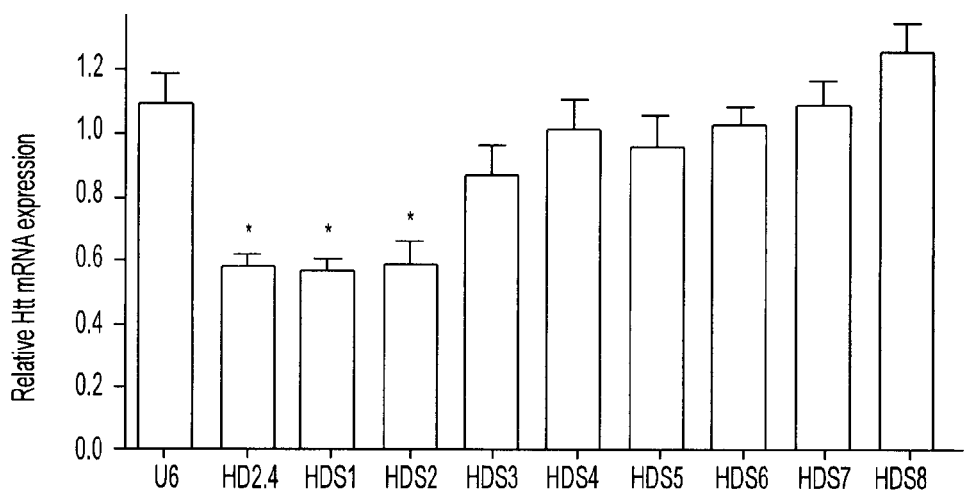
FIG. 3. Selection and screening of htt-targeting siRNAs with low off-targeting potentials. (a) Schematic outlining the selection of "safe" seed siRNAs with proper strand-biasing.

Selection and Screening of Htt-Targeting siRNAs with Low Off-Targeting Potentials The siRNA toxicity potentials have been correlated with seed complement frequencies in the human 3'-UTRome (Anderson, E. M., A. Birmingham, S. Baskerville, A. Reynolds, E. Maksimova, D. Leake, et al. (2008). *Experimental validation of the importance of seed complement frequency to siRNA specificity*. RNA 14(5):853-61). Here, the inventors estimated the number of potential off-target transcripts (POTs) for each hexamer by determining the number of human RefSeq 3'-UTRs containing a specified hexamer (out of the 4096 possible). Similar to the previous findings, the majority of hexamers are present in ~4000 3'-UTRs or more, and interestingly, there is an unexplainable peak (containing 1135 hexamers) in the distribution. These latter hexamers are present in less than 2000 3'-UTRs (FIG. 2c). Since siRNAs are typically designed to target coding regions, we determined the probability of finding these relatively rare hexamers in human RefSeq coding exons. This was ~14%, suggesting that 1 in 7-8 randomly designed siRNAs would contain these rare hexamers in the seed region. To improve upon this nominal probability, low frequency hexamers may first be located within target transcript sequence and subsequently used as a foundation for designing siRNAs with minimal off-targeting potentials. For example, the inventors scanned the human htt coding sequence for low frequency hexamers, and with each instance, examined the nearby context to determine whether the siRNA containing the hexamer seed complement would satisfy two criteria: (1) faithful loading of the intended antisense guide strand and (2) GC-content between 20-70% (FIG. 3a). Not only do these attributes represent the most prominent determinants of siRNA potency, but proper loading of the antisense guide strand is mandated to mitigate potential off-targeting mediated by the sense "passenger" strand. Strand-loading is dictated by the thermodynamic properties present at the siRNA duplex ends, with guide strand loading encouraged by weak pairing (A/G-U) at the 5' end and strong G-C binding at the opposing terminus (FIG. 3a). Of note, the inventors apply this principle to the terminal two base-pairs at each end and take advantage of weak G-U wobble pairing to impart instability at the 5' end of the antisense strand when applicable. Finally, the inventors select siRNAs based on a fairly liberal range of GC-content (20-70%) which supports a suitable potential for efficient silencing (>80%), as determined by our evaluation of large-scale knock-down data for 2431 randomly designed siRNAs targeting 31 unique mRNAs (data not shown). As with most siRNA design algorithms, candidate siRNA sequences satisfying the above criteria are subjected to BLAST to evaluate the potential for off-target cleavage events mediated by near-perfect complementarity to unintended mRNAs (for BLAST parameters, see Birmingham, A., E. Anderson, K. Sullivan, A. Reynolds, Q. Boese, D. Leake, et al. (2007). *A protocol for designing siRNAs with high functionality and specificity*. Nat Protoc 2(9):2068-78)).

Figure 7:
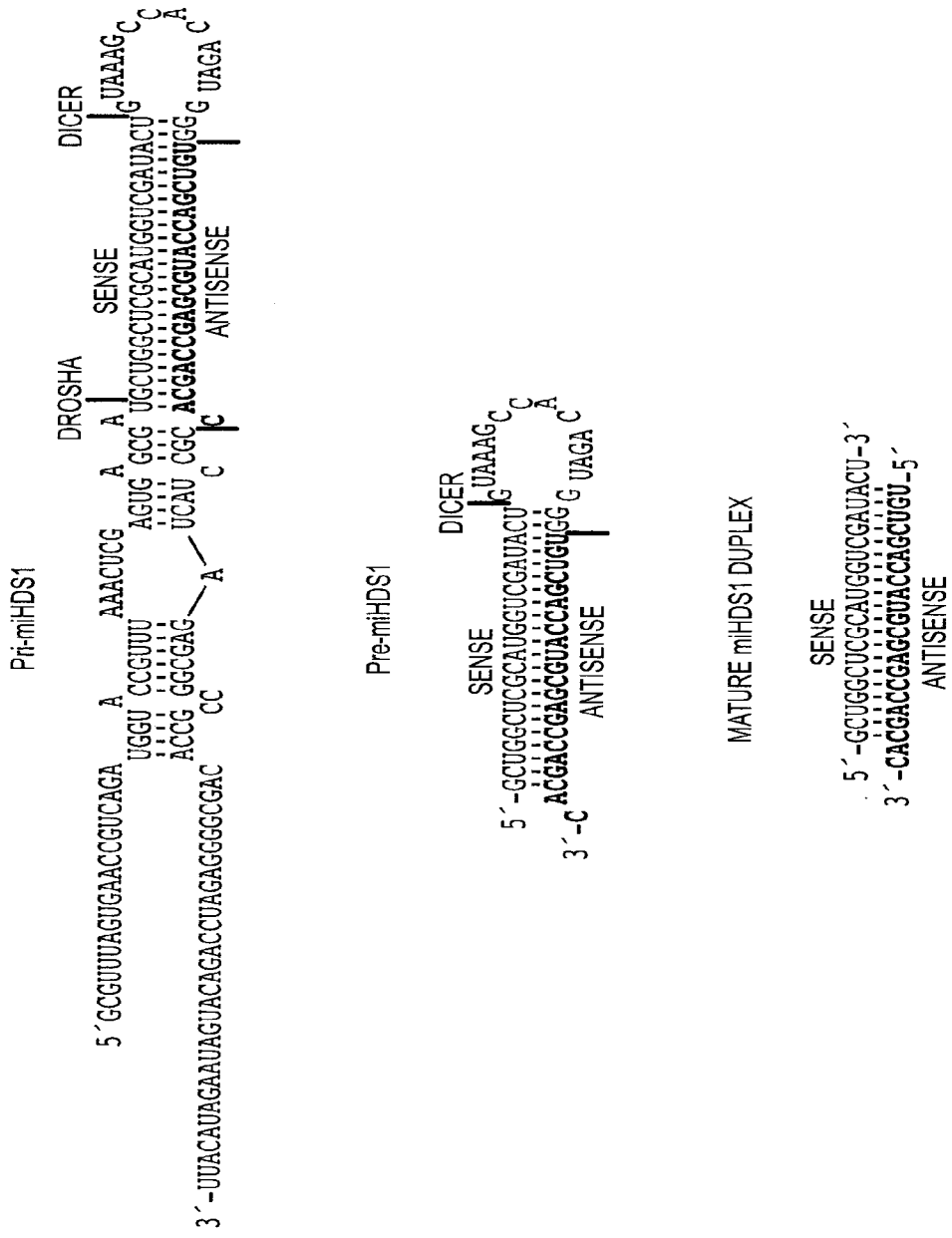
FIG. 7. Full-length sequences and structures for pri-mi-HDS.1.
Figure 8:
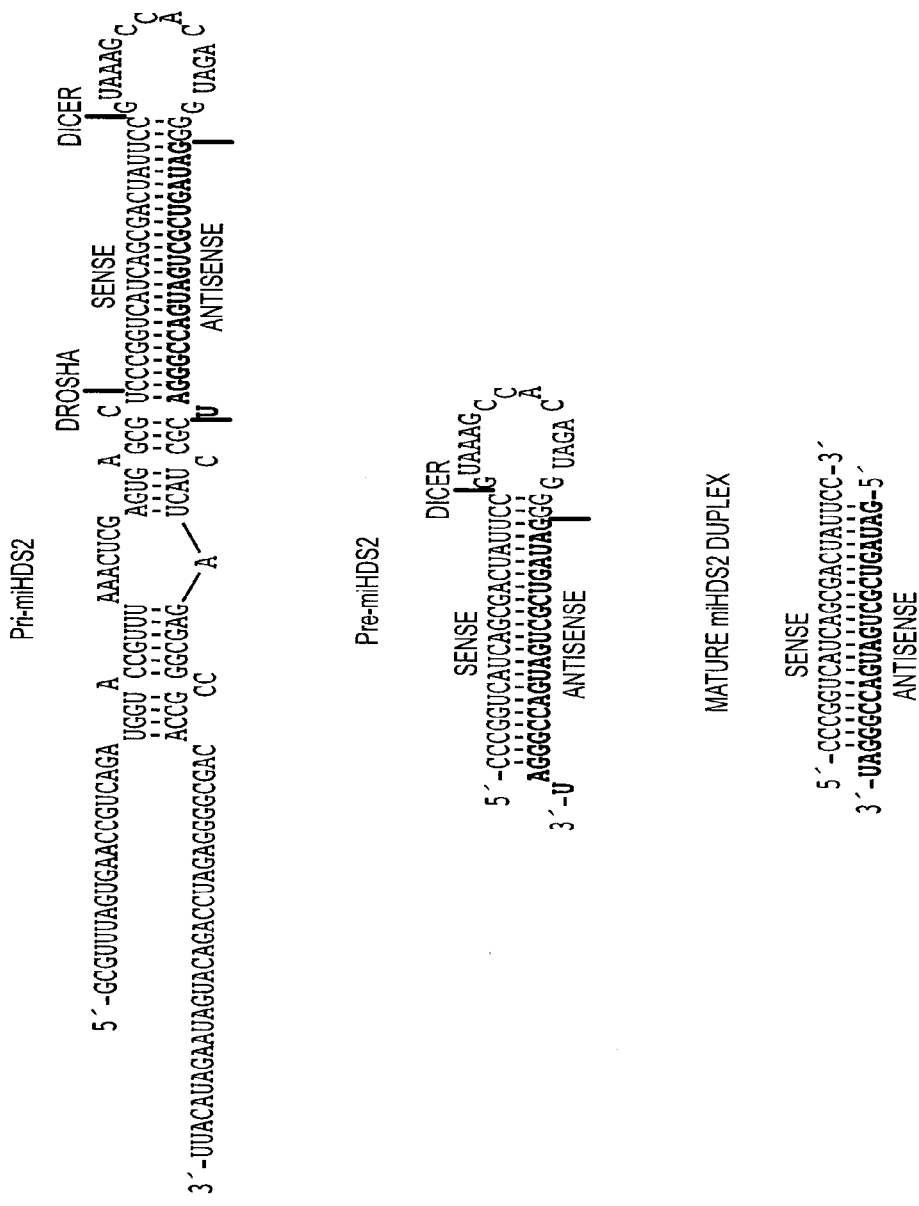
FIG. 8. Full-length sequences and structures for pri-mi-HDS.2.

Using the inventors' siRNA design criteria (low POTs seed, strand-biasing, and GC-content), the inventors initially identified eight htt-targeting candidate sequences for further testing. We embedded the siRNA sequences into the context of the inventors' U6-driven artificial miRNA-based expression vectors (FIG. 2a) and screened them for gene silencing against endogenous htt in HEK293 cells (FIG. 3b). The inventors observed two candidates (HDS1 and HDS2, Tables 3 and 4, and FIGS. 7 and 8) that effectively silence htt mRNA (~50%, relative to control). Notably, this magnitude of in vitro silencing against endogenous htt is comparable to the levels achieved by other htt RNAi sequences (including HD2.4) that previously showed therapeutic efficacy in HD mouse models (Harper, S. Q., P. D. Staber, X. He, S. L. Eliason, I. Martins, Q. Mao, et al. (2005). *RNA interference improves motor and neuropathological abnormalities in a Huntington's disease mouse model*. Proceedings of the National Academy of Sciences, USA 102(16):5820-5825; Rodriguez-Lebron, E., E. M. Denovan-Wright, K. Nash, A. S. Lewin, and R. J. Mandel (2005). *Intrastriatal rAAV-mediated delivery of anti-huntingtin shRNAs induces partial reversal of disease progression in R6/1 Huntington's disease transgenic mice*. Mol Ther 12(4):618-633; Boudreau, R. L., J. L. McBride, I. Martins, S. Shen, Y. Xing, B. J. Carter, et al. (2009). *Nonallele-specific silencing of mutant and wild-type huntingtin demonstrates therapeutic efficacy in Huntington's disease mice*. Mol Ther 17(6):1053-63).

Microarray Analyses of Seed-Related Off-Targeting

To validate the low off-targeting potential of these effective sequences (HDS1 and HDS2) and the inventors' siRNA design scheme, the inventors performed microarray analysis to assess seed-related off-target gene silencing. The inventors included several RNAi constructs which target human htt and various control sequences to help discern off-target gene silencing from gene expression changes that result from suppressing htt (Table 1). Of note, all sequences used were designed to promote proper loading of the antisense strand to avoid the confounding potential of off-targeting mediated by the passenger strand. The htt-silencing group consisted of HDS1, HDS2, HD2.4 and HD8.2; the latter two were previously designed without regard for the seed sequence and have >4500 POTs each (FIG. 2c). The control group (i.e. non-htt-targeting) consisted of several sequences (8.2 mis, 8.2-124a, Terror, and Safe), each designed to serve a unique purpose (Table 1). 8.2 mis contains the same seed as HD8.2 but has central mismatches to prevent htt silencing, while 8.2-124a and Terror are HD8.2 scrambled sequences which respectively contain a seed mimic of miR-124a (a naturally occurring and highly conserved miRNA) and a seed with high off-targeting potential (i.e. complements a highly abundant hexamer in the human 3'-UTRome). Of note, 8.2-124a was included as a control for detecting seed-related off-targeting within the microarray data and to underscore the prospective concern of designing siRNAs (scrambled controls or on-target sequences) such that they unintentionally contain naturally occurring miRNA seeds. Finally, the Safe construct contains an arbitrary sequence designed to have low off-targeting potential based on 3'-UTR hexamer frequencies. Together, these constructs provide a wide-range of off-targeting potentials and address problems that can inadvertently arise when including scrambled sequences as controls in RNAi experiments, a commonly used practice.

Figure 4:
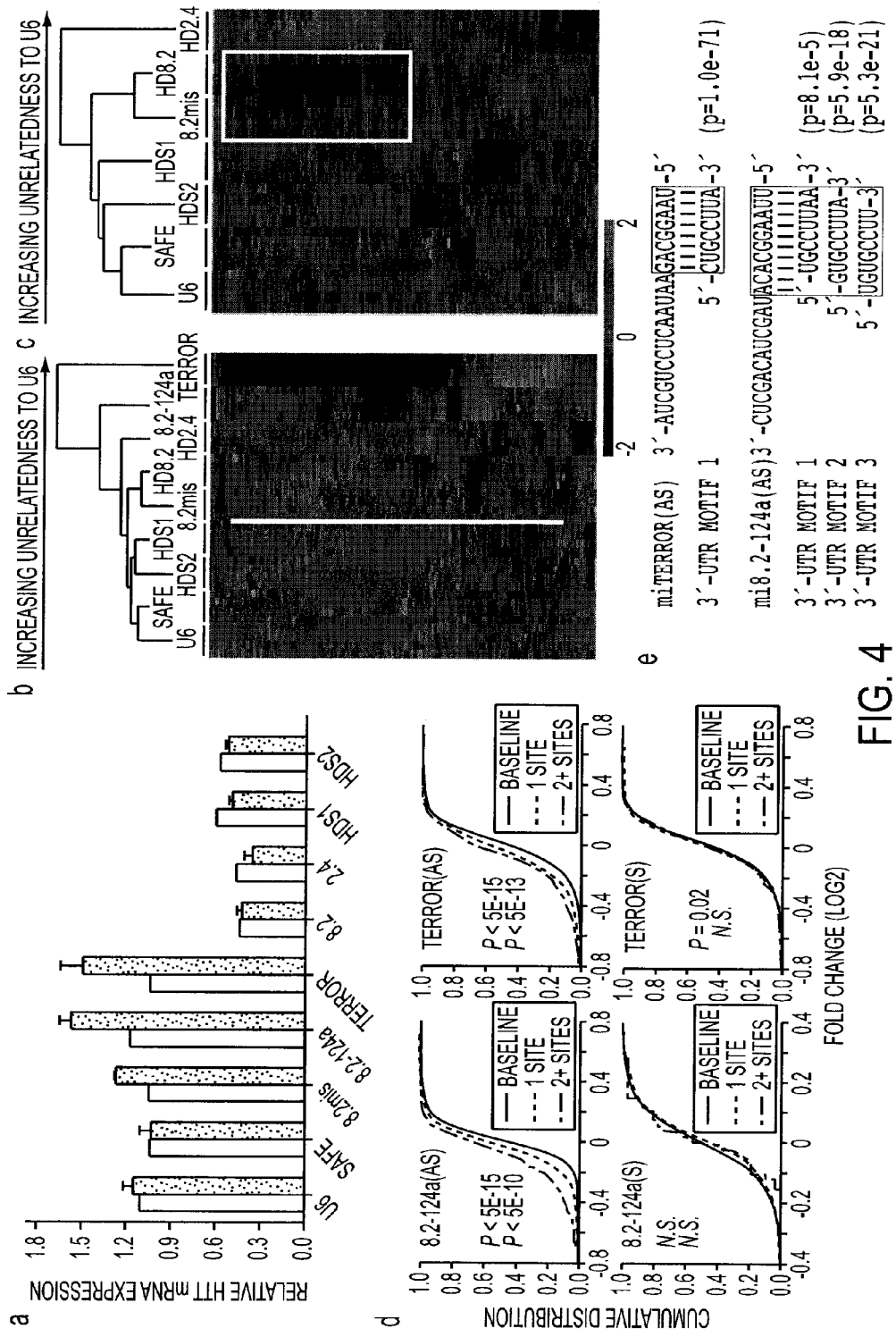
FIG. 4. Evaluation of microarray data for htt silencing and off-targeting. HEK293 cells were transfected with U6 promoter-only or U6-driven artificial miRNA expression plasmids (n=4 for each treatment), and RNA was harvested 72 h later for microarray analysis. Two-way ANOVA was performed to detect differentially expressed genes among the treatment groups. (a) Htt mRNA levels determined by microarray (grey bars) were consistent with those measured by QPCR (black bars) using the same RNA samples. (b) Hierarchical clustering and heat-maps were generated using differentially expressed genes (P<0.0001, 825 genes) to visualize the relationships among the treatment groups. Interestingly, all of the "safe" seed sequences are more related to U6 than the remaining sequences predicted to have higher off-targeting potentials (boundary marked by white line). (c) Hierarchical clustering and heat-maps were generated using differentially expressed genes (P<0.01, 992 genes) to visualize the relationships among the treatment groups. The impact of seed sequence on gene expression can be appreciated by the clustering of 8.2 and 8.2 m is which share the same seed. Notably, the predicted low off-targeting sequences (Safe, HDS1 and HDS2) are more similar to U6, and have smaller off-targeting signatures compared to both 2.4 and 8.2. Seed-related off-targeting was evaluated by cumulative distribution (d) and motif discovery (e) analyses. (d) Cumulative distribution plots for gene expression values are shown for transcripts containing (1 site or 2+ sites) or lacking (baseline) 3'-UTR seed complement binding sites for the indicated sequence and strand. A shift to the left indicates an increased likelihood of being down-regulated. AS=antisense, S=sense. KS-test P-values are shown; N.S.=no statistical significance (P>0.1). (e) Motif discovery analyses identified an enrichment of seed complement binding sites in the 3'-UTRs of down-regulated genes (>1.1-fold) unique to each treatment. Shown here are the examples of 8.2-124a (SEQ ID NO: 212) and Terror (SEQ ID NO: 211); similar data for the remaining sequences supports that each mediates detectable seed-related off-targeting to some degree (see FIG. 6 below).

The inventors carried out transcriptional profiling in cultured HEK293 cells 72 h after transfection with RNAi expression plasmids (N=4 per construct). Initially, gene expression changes were detected by performing ANOVA statistical analysis using all treatments included in the study. As anticipated, htt was consistently among the most significantly down-regulated transcripts in samples treated with htt-targeting RNAi sequences (P<5e-11, relative to U6), and these microarray data were corroborated by QPCR evaluation of htt mRNA levels in the same RNA samples (FIG. 4a). Next, the inventors performed hierarchical clustering using differentially expressed genes within the dataset (P<0.0001, 827 genes) to measure the relatedness among the various treatments. These include gene expression changes which occur as a result of knocking down endogenous htt in addition to sequence-specific off-targeting events. Notably, we observed a closer relationship between the low off-targeting potential sequences (Safe, HDS1 and HDS2) and the U6 promoter-only control as compared to the remaining sequences, which were designed either blindly (HD2.4 and HD8.2) or intentionally with mid-to-high off-targeting potentials (8.2-124a and Terror). These clustering results support a clear association between off-targeting potential and impact on the transcriptional profile (FIG. 4b), corroborating the Anderson et al. observations (Anderson, E. M., A. Birmingham, S. Baskerville, A. Reynolds, E. Maksimova, D. Leake, et al. (2008). *Experimental validation of the importance of seed complement frequency to siRNA specificity*. RNA 14(5):853-61). In addition, these data substantiate that changes related to off-targeting are more robust than those resulting from htt silencing. Visualization of the complementing heatmap made obvious the overwhelming amount of off-targeting caused by Terror and, to a slightly lesser degree, 8.2-124a (FIG. 4b). The overlap between these sequences is likely due to their seed similarity (Table 1), and subsequent analyses confirmed that much of this off-targeting was seed-related. For the sequences with low-to-mid off-targeting potentials, the relationship between off-targeting potentials and gene expression profiles was better visualized by removing the Terror and 8.2-124a samples from the ANOVA analysis and repeating hierarchical clustering of differentially expressed genes (P<0.01, 985 genes) (FIG. 4c). With this approach, the heat maps showed gene suppression signatures that were unique to each of these sequences, with the exception of HD8.2 and 8.2 mis. As previously noted, these constructs share the same seed sequence, and this evident overlap affirms that much of the observed gene expression changes are seed-related, rather than caused by htt knockdown. In addition, this example highlights the benefit of designing on-target and control siRNA sequences that share the same seed. This preserves off-targeting between the two sequences and is therefore beneficial when applying RNAi-based tools to study gene function or validate drug targets.

Figure 6:
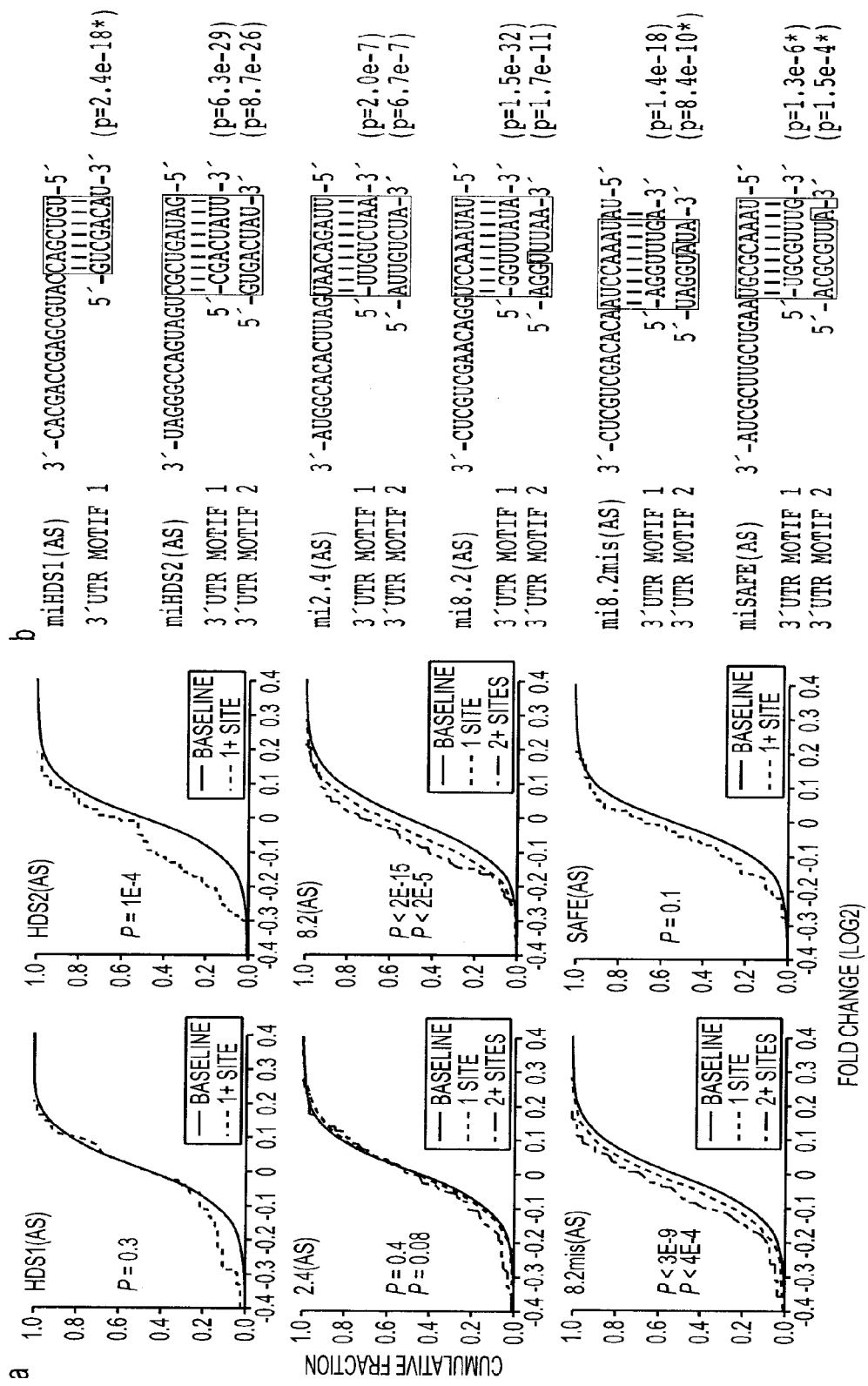
FIG. 6. Evaluation of microarray data for off-targeting. Seed-related off-targeting was evaluated by cumulative distribution (a) and motif discovery (b) analyses. (a) Cumulative distribution plots for gene expression values are shown for transcripts containing (1 site or 2+ sites) or lacking (baseline) 3'-UTR seed complement binding sites for the indicated sequence and strand. A shift to the left indicates an increased likelihood of being down-regulated. AS=antisense. KS-test P-values are shown; N.S.=no statistical significance (P>0.1). (b) Motif discovery analyses identified an enrichment of seed complement binding sites in the 3'-UTRs of down-regulated genes (>1.1-fold) unique to each treatment (SEQ ID NOs: 210 and 213-217, respectively, in order of appearance).

The inventors next assessed whether the observed gene expression changes could be explained by seed-mediated gene silencing. Cumulative distribution analyses of gene expression levels indicated that transcripts containing seed binding sites for the antisense strand in their 3'-UTR had a much higher probability of being down-regulated (i.e. curve shifting left) (FIG. 4d, top and FIG. 6), and the degree of down-regulation was dependent upon the number of binding sites present, consistent with previous reports characterizing miRNA seed-mediated silencing of target transcripts. The inventors also performed cumulative fraction analyses to detect seed-related gene silencing caused by the passenger strand; in this case, the presence of 3'-UTR binding sites had little to no detectable influence on gene expression, supporting that the current vector design (i.e. two strong G-C base-pairs at the sense 5' and two weak A/G-U base-pairs at the sense 3') promotes proper strand-biasing (FIG. 4d, bottom). As a complementary approach to detect seed-related gene silencing events, the inventors performed motif discovery analyses using 3'-UTR sequences of down-regulated transcripts unique to each treatment group. In all instances, the inventors found significant enrichment of motifs complementary to the respective seed sequences in the uniquely down-regulated transcript 3'-UTRs relative to a background 3'-UTR dataset consisting of all known human 3'-UTRs (FIG. 4e and FIG. 6b). These data confirm that seed-related off-target gene silencing is present in the datasets for all RNAi sequences tested. Upon further evaluation, the inventors estimated the number of seed-related off-targets for each RNAi sequence by identifying transcripts that were down-regulated (1.1-fold, P<0.05, relative to U6) and contain the relevant seed complements in their 3'-UTR (Table 2). This analysis revealed that using the present "safe" seed design method, HDS1 and HDS2 show nearly a log improvement in minimizing seed-related off-targeting, as compared to previous lead candidates, HD2.4 and HD8.2.

In Vivo Silencing and Safety of HDS Sequences

Figure 5:
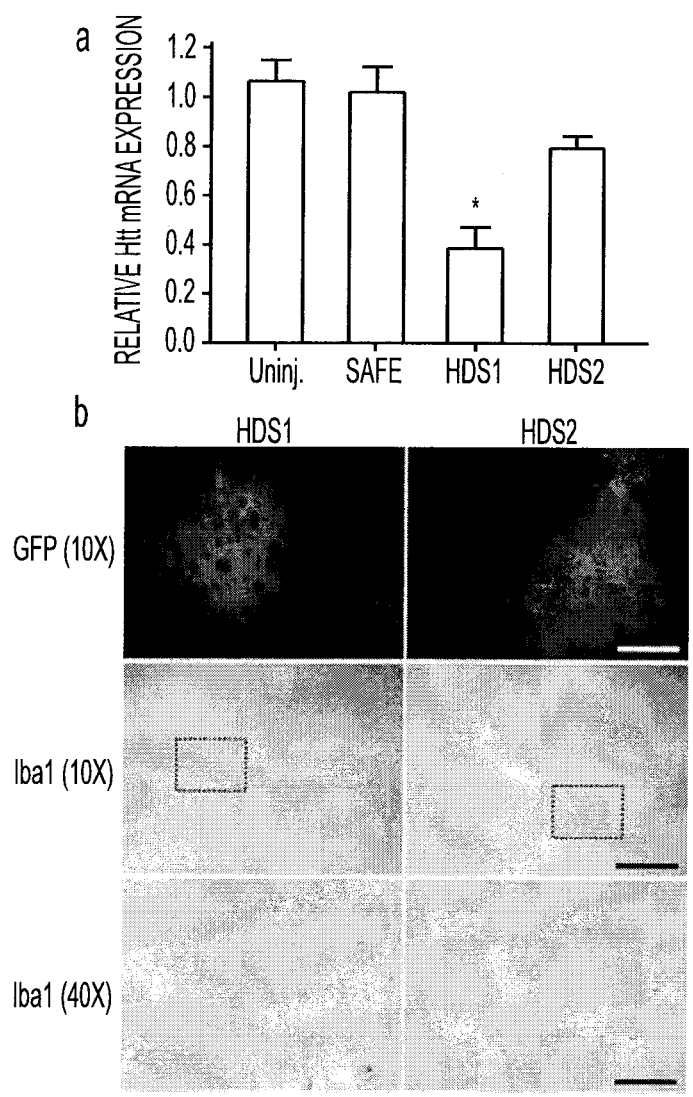
FIG. 5. Silencing efficacy and safety of HDS sequences in mouse brain. Wild-type mice were injected into the striatum with AAV viruses co-expressing artificial miRNAs and GFP. (a) At 3 weeks post-injection, GFP-positive striata were harvested and QPCR analysis was performed to measure endogenous mouse Htt mRNA levels. Results are shown as mean±SEM (n≥3, * indicates P=0.001, relative to uninjected striata). (b) Brains from additional cohorts of injected mice were harvested at 6 months post-injection and histological analyses were performed to assess neurotoxicity. Photomicrographs representing GFP autofluorescence and immunohistochemical staining of Iba1-positive microglia are shown. Scale bars=200 and 50 μm for 10× and 40× images respectively.

Having identified that HDS1 and HDS2 have substantially fewer seed-related off-targets, the inventors next tested these sequences for silencing and safety in vivo in mouse brain. The inventors intrastriatally injected AAV1-miHDS1, AAV1-miHDS2 or AAV1-miSafe (control) into two cohorts of wild-type mice. Of note, HDS1 exhibits full complementarity to mouse, rhesus and human htt sequences, making it an attractive candidate for preclinical testing. HDS2 only targets human htt, with mismatches to the corresponding mouse and rhesus target sequences. At three weeks post-injection, the inventors performed QPCR analyses to evaluate gene silencing efficacy in striatal tissue harvested from the first cohort of animals and observed significant htt mRNA knockdown (~60%) in mice treated with AAV1-miHDS1, relative to uninjected and AAV1-miSafe-treated mice (FIG. 5a). Notably, previous reports from the inventors' laboratory and others' demonstrate that ~60% silencing of striatal htt transcripts in HD mouse models markedly reduces protein levels, resulting in appreciable therapeutic efficacy. The second cohort of mice was sacrificed at six months post-injection to evaluate long-term vector tolerability. Staining for Iba1, a marker for resting and reactive microgila, showed no evidence for neurotoxicity in transduced regions of the striata, relative to nearby untransduced tissue (FIG. 5b; refer to FIG. 1 for comparison to miSCR, a toxic sequence with high off-targeting potential). These results are encouraging considering that HD2.4, previously shown to be therapeutically efficacious in short term studies, caused modest but still detectable increases in Iba1 staining in both wild-type and HD mice. Furthermore, the data corroborate previous reports demonstrating that reducing wild-type htt mRNA levels by ~60% in mouse striatum does not induce overt neurotoxicity.

Discussion

Although the absolute specificity and safety of RNAi approaches remains questionable, recent advances in understanding RNAi-induced toxicities (e.g. pathway saturation and off-targeting) are facilitating researchers in devising strategies to limit these adverse events. For example, the discovery that high-level shRNA expression causes lethality in mice (Grimm, D., K. L. Streetz, C. L. Jopling, T. A. Storm, K. Pandey, C. R. Davis, et al. (2006). *Fatality in mice due to oversaturation of cellular microRNA/short hairpin RNA pathways*. Nature 441(7092):537-41) prompted us to test alternative hairpin-based vectors (e.g. artificial miRNAs) for their capacity to limit the production of RNAi substrates following viral-based delivery in vivo, thus resulting in improved tolerability. Furthermore, Anderson et al recently evaluated the impact of 3'-UTR seed complement frequencies on siRNA off-targeting potentials, using a set of randomly designed siRNA sequences targeting a variety of genes (Anderson, E. M., A. Birmingham, S. Baskerville, A. Reynolds, E. Maksimova, D. Leake, et al. (2008). *Experimental validation of the importance of seed complement frequency to siRNA specificity*. RNA 14(5):853-61). Low off-targeting potential siRNAs were found to exhibit higher specificity as per mRNA profiling, lower toxicity and fewer false positives in phenotypic screens. The authors proposed that siRNAs with low seed complement frequencies improve the accuracy of RNAi screens to study gene function or validate drug targets. Here, the inventors took advantage of these findings to deliberately design therapeutic siRNAs with low off-targeting potentials, as a means to promote safety in pre-clinical development of RNAi therapy for HD. The inventors identified two candidates (HDS1 and HDS2) which effectively silence human htt mRNA, induce minimal seed-related off-targeting and are well-tolerated in mouse brain long-term.

Although the inventors' work was initially undertaken to develop siRNAs with low off-targeting potentials, a similar strategy may be employed to intentionally design siRNAs with high off-targeting capacities (e.g. Terror sequence) for use as anti-tumor agents. This approach may deter tumor escape by more broadly disrupting essential cellular pathways, as compared to delivering siRNAs targeting specific oncogenes.

Researchers using RNAi triggers in basic and translational research often employ scrambled sequences as controls. The present work highlights the importance of carefully designing control siRNAs, with attention to putative seed sequences that can inadvertently induce considerable off-target silencing via miRNA-based mechanisms. Here, the inventors intentionally introduced either a known miRNA seed (8.2-124a) or a seed with high off-targeting potential (Terror) into scrambled siRNA sequences. As expected, both induced significant seed-related alterations in transcriptional profiles, when compared to our control vector (Safe) designed to exhibit low off-targeting potential. Furthermore, we describe and test the redesign of a "same seed" control vector (8.2 mis). This approach resulted in significant preservation of off-targeting relative to the corresponding on-target sequence (HD8.2). These data encourage the use of "same seed" controls in future RNAi experiments.

There are several key considerations which apply to "safe" seed siRNA design. First, low off-targeting potential does not necessarily mean non-toxic, as off-target identity remains a crucial influence on tolerability. The inventors' improved ability to accurately identify high probability off-targets allows us to better select lead candidate siRNAs, particularly when several low off-targeting sequences are available for a given target sequence. Second, observed safety in pre-clinical toxicity studies in either rodents or non-human primates may not ensure success in humans, as differences in 3'-UTR sequences creates off-targeting profiles unique to each species (Burchard, J., A. L. Jackson, V. Malkov, R. H. Needham, Y. Tan, S. R. Bartz, et al. (2009). *MicroRNA-like off-target transcript regulation by siRNAs is species specific*. Rna 15(2): 308-15). It is important to note, that although off-target identities may be species-specific, the off-targeting potentials for each hexamer remain highly consistent, as hexamer frequencies among several species (e.g. mouse, rhesus and human) show minimal variability (data not shown). Third, locating these rare hexamers may be difficult in small target transcripts, and thus other means to limit off-targeting may be necessary. For instance, several reports have demonstrated that certain chemical modifications to the seed nucleotides significantly reduce off-targeting from chemically synthesized siRNAs (Jackson, A. L., J. Burchard, D. Leake, A. Reynolds, J. Schelter, J. Guo, et al. (2006). *Position-specific chemical modification of siRNAs reduces "off-target" transcript silencing*. RNA 12(7):1197-205; Bramsen, J. B., M. M. Pakula, T. B. Hansen, C. Bus, N. Langkjaer, D. Odadzic, et al. (2010). *A screen of chemical modifications identifies position-specific modification by UNA to most potently reduce siRNA off-target effects*. Nucleic Acids Res 38(17):5761-73; Vaish, N., F. Chen, S. Seth, K. Fosnaugh, Y. Liu, R. Adami, et al. (2011). *Improved specificity of gene silencing by siRNAs containing unlocked nucleobase analogs*. Nucleic Acids Res 39(5):1823-32). The prospect of combining "safe" seed design with chemical modifications serves as a provocative strategy to develop synthetic siRNAs with very high specificity. However, for expressed RNAi, chemical modifications are not applicable, thus "safe" seed design provides the primary means to limit off-targeting for these hairpin-based vectors.

In summary, "safe" seed siRNA design has significant implications for therapeutic development which may result in substantial time- and cost-saving opportunities. Traditional small molecules are initially screened for efficacy and later tested for safety, since predicting potential side effects remains a challenge due to the complex nature of small molecule interactions. By contrast, the inventors' ability to predict off-targeting (derived from base-pairing) for oligonucleotide-based drugs provides a unique opportunity to prioritize safety during drug development and subsequently screen for efficacy.

Materials & Methods

Plasmids and Viral Vectors

The plasmids expressing mouse U6-driven artificial miRNAs were cloned as previously described using the DNA oligonucleotides listed in Table 5 (Boudreau, R. L., A. Mas Monteys, and B. L. Davidson (2008). *Minimizing variables among hairpin-based RNAi vectors reveals the potency of shRNAs*. RNA 14:1834-1844). For AAV production, artificial miRNA expression cassettes were cloned into pFBGR-derived plasmids which co-express CMV-driven GFP (Boudreau, R. L., I. Martins, and B. L. Davidson (2009). *Artificial MicroRNAs as siRNA Shuttles: Improved Safety as Compared to shRNAs In vitro and In vivo*. Mol Ther 17(1):169-17).

Recombinant AAV serotype 2/1 vectors (AAV1-GFP, AAV1-miSCR, AAV1-miHDS1, and AAV1-miHDS2 were generated by the University of Iowa Vector Core facility as previously described (Urabe, M., C. Ding, and R. M. Kotin (2002). *Insect cells as a factory to produce adeno-associated virus type 2 vectors*. Hum Gene Ther 13(16):1935-1943). Viruses were initially purified using an iodixanol gradient (15-60% w/v) and subjected to additional purification via ion exchange using MustangQ Acrodisc membranes (Pall Corporation, East Hills, N.Y.). AAV1 vectors were resuspended in Formulation Buffer 18 (HyClone, Logan, Utah), and titers (viral genomes per ml) were determined by QPCR.

AAV Injections and Brain Tissue Isolation

All animal protocols were approved by the University of Iowa Animal Care and Use Committee. Wildtype FVB mice were injected with AAV1 vectors as previously reported (Harper, S. Q., P. D. Staber, X. He, S. L. Eliason, I. Martins, Q. Mao, et al. (2005). *RNA interference improves motor and neuropathological abnormalities in a Huntington's disease mouse model*. Proceedings of the National Academy of Sciences, USA 102(16):5820-5825; McBride, J. L., R. L. Boudreau, S. Q. Harper, P. D. Staber, A. M. Monteys, I. Martins, et al. (2008). *Artificial miRNAs mitigate shRNA-mediated toxicity in the brain: Implications for the therapeutic development of RNAi*. Proc Natl Acad Sci USA 105(15):5868-73). For all studies, unless indicated otherwise, mice were injected bilaterally into the striatum (coordinates: 0.86 mm rostral to bregma, ±1.8 mm lateral to midline, 3.5 mm ventral to the skull surface) with 4 ul of AAV1 virus (at ~1×10$^{12}$ viral genomes/ml). Mice used in histological analyses were anesthetized with a ketamine/xylazine mix and transcardially perfused with 20 ml of 0.9% cold saline, followed by 20 ml of 4% paraformaldehyde in 0.1 M PO$_4$ buffer. Mice were decapitated, and the brains were removed and post-fixed overnight in 4% paraformaldehyde. Brains were stored in a 30% sucrose solution at 4° C. until cut on a sliding knife microtome at 40 μm thickness and stored at −20° C. in a cryoprotectant solution. Mice used for QPCR analyses were perfused with 20 ml of 0.9% cold saline. Brains were removed and sectioned into 1 mm thick coronal slices using a brain matrix (Roboz, Gaithersburg, Md.). Tissue punches were taken from the striatum using a tissue core (1.4 mm in diameter) and triterated in 50 ul of TRIzol (Invitrogen, Carlsbad, Calif.). RNA was isolated from striatal punches using 1 ml of TRIzol.

Immunohistochemical Analyses

Free-floating, coronal brain sections (40 μm thick) were processed for immunohistochemical visualization of microglia (anti-Iba1, 1:1000, WAKO, Richmond, Va.). All staining procedures were carried out as previously described (McBride, J. L., R. L. Boudreau, S. Q. Harper, P. D. Staber, A. M. Monteys, I. Martins, et al. (2008). *Artificial miRNAs mitigate shRNA-mediated toxicity in the brain: Implications for the therapeutic development of RNAi*. Proc Natl Acad Sci USA 105(15):5868-73), using goat anti-rabbit IgG secondary antibody (1:200) and Vectastain ABC-peroxidase reagent (both from Vector Laboratories, Burlingame, Calif.). Stained or unstained (the latter for visualization of GFP autofluorescence) sections were mounted onto Superfrost Plus slides (Fisher Scientific, Pittsburgh, Pa.) and coverslipped with Gelmount (Biomeda, Foster City, Calif.) or Vectashield (Vector Laboratories). Images were captured using an Olympus BX60 light microscope and DP70 digital camera, along with Olympus DP Controller software (Olympus, Melville, N.Y.).

Hexamer Distribution Analyses

All human RefSeq IDs, official gene symbols, and coding and 3'-UTR sequences (Hg19, GRCH37) were obtained and only sequences with NM_*pre-fixes were used for analysis. For 3'-UTR sequences, the non-overlapping frequency of each individual hexamer (4096 possible) was counted to determine the number of 3'-UTRs containing a given hexamer. Non-overlapping sites were considered to account for actual binding site availability. For coding sequence, the total hexamer frequencies were determined, allowing overlapping hexamers, to estimate the probability of selecting siRNA sequences containing the specified hexamer. For genes with variants (i.e. same official gene symbol but different accession number), the maximum count for each hexamer was used.

Cell Culture and Transfection

For the HDS screen, HEK293 cells were grown in 24-well plates in growth media containing 10% fetal bovine serum (FBS) and transfected in quadruplicate with 400 ng of plasmid using Lipofectamine 2000 (Invitrogen) by adding the lipid:DNA complexes directly to the growth media. Total RNA was isolated at 24 h post-transfection using 1 ml of Trizol. For microarray studies, HEK293 cells were grown in 12-well plates in growth media (10% FBS) and transfected with 1 ug of plasmid under serum-free conditions. Lipid:DNA complexes were removed 3 h later and replaced with growth media (5% FBS). At 72 h (microarray) post-transfection, total RNA was isolated using 1 ml of TRIzol.

Quantitative Real-Time PCR (QPCR)

Random-primed first-strand cDNA synthesis was performed using 500 ng total RNA (High Capacity cDNA Reverse Transcription Kit; Applied Biosystems, Foster City, Calif.) per manufacturer's protocol. Assays were performed on a sequence detection system using primers/probe sets specific for human htt and GAPDH or mouse htt and beta-actin (Prism 7900HT and TaqMan 2× Universal Master Mix; Applied Biosystems). Relative gene expression was determined using the $\Delta\Delta C_T$ method, normalizing to either GAPDH or beta-actin mRNA levels.

Microarray Analyses

Microarray analysis was done with assistance from the University of Iowa DNA Facility (Iowa City, Iowa). Fifty nanograms of total RNA template were used to produce amplified cDNA using the Ovation Biotin RNA Amplification System, v2 (NuGEN Technologies) following the manufacturer's protocol. Amplified cDNA product was purified with DNA Clean and Concentrator-25 (Zymo Research). 3.75 μg of amplified cDNA were processed using the FL-Ovation cDNA Biotin Module v2 (NuGEN Technologies, San Carlos, Calif.) to produce biotin labeled antisense cDNA in 50- to 100 bp fragments. Following denaturation at 99° C. for 2 min, fragmented, labeled cDNA were combined with hybridization control oligomer (b2) and control cRNAs (BioB, BioC, BioD, and CreX) in hybridization buffer and hybridized to the HuGene 1.0ST GeneChip (Affymetrix, Santa Clara, Calif.) capable of detecting more than 28,000 genes. Following an 18 hour incubation at 45° C., the arrays were washed, stained with streptavidinphycoerythrin (Molecular Probes), and then amplified with an anti-streptavidin antibody (Vector Laboratories) using the Fluidics Station 450 (Affymetrix). Arrays were scanned with the Affymetrix Model 3000 scanner and data collected using GeneChip operating software (GCOS) v1.4. Each sample and hybridization underwent a quality control evaluation, including percentage of probe sets reliably detecting between 40 and 60% present call and 3'-5' ratio of the GAPDH gene less than 3.

Partek Genomics Suite (Partek GS, Saint Louis, Mo.) was used to preprocess, normalize and analyze microarray data. Affymetrix array raw fluorescence intensity measures of gene expression were normalized and quantified using robust multi-array analysis (RMA). To identify differentially expressed genes among the nine treatment groups (N=4 each, Table 1), the inventors employed two-way ANOVA (variables: scan date and treatment) since arrays were processed in groups of four (one replicate per treatment in each group). Pair-wise contrasts between groups of interest were performed when indicated. Principal component and hierarchical clustering analyses were used to visualize differential gene expression.

Cumulative Distribution Analyses

3'-UTR sequences for all RefSeq mRNAs on the HuGene 1.0 ST chip were obtained, and the number of non-overlapping seed complement binding sites (octamers) per 3'-UTR for each of the indicated inhibitory RNAs was determined. Three possible octamers for each artificial miRNA were considered to account for flexibility in Drosha and Dicer cleavage (Table 5). Transcripts were parsed into groups depending on the number of seed complements in their 3'-UTR (no sites, 1 site, 2+ sites), and cumulative distributions of gene expression values (Log 2 fold-change, relative to U6) were plotted. Two-sample Kolmogorov-Smirnov (KS) tests were performed to evaluate the statistical significance of distributional deviations relative to baseline (no sites).

Motif Discovery

The Venn diagram feature on Partek GS was used to create lists of uniquely down-regulated genes (1.1-fold, P<0.05 or 1.2-fold, P<0.01, relative to U6) for each treatment, taking into account htt silencing (e.g. HDS1, HDS2, HD2.4 and HD8.2 were included in one Venn diagram, and Safe, Terror, 8.2 mis and 8.2-124a were included in another). Ensembl Gene IDs were obtained using the Gene ID Conversion Tool at the David Bioinformatics Resources web-server (Huang da, W., B. T. Sherman, Q. Tan, J. R. Collins, W. G. Alvord, J. Roayaei, et al. (2007). *The DAVID Gene Functional Classification Tool: a novel biological module-centric algorithm to functionally analyze large gene lists*. Genome Biol 8(9):R183). Ensemble Gene IDs were subjected to target set analysis using the Amadeus Motif Discovery Platform (Allegro Software Package) to identify 8 mers enriched in the target set 3'-UTRs, relative the provided human 3'-UTR background dataset (Halperin, Y., C. Linhart, I. Ulitsky, and R. Shamir (2009). *Allegro: analyzing expression and sequence in concert to discover regulatory programs. Nucleic Acids Res* 37(5):1566-79). Amadeus blindly identified an enrichment of seed complement motifs for each RNAi sequence tested, and the lowest p-values for the relevant motifs were reported.

TABLE 1

Microarray constructs.

| Construct | Targets HTT7 | 8 mer Seed | Off-Targeting Potential (# of OTs*) | Purpose/Design Rationale |
|---|---|---|---|---|
| U6 promoter | No | N/A | N/A | Normalizing control |
| mHDS1 | Yes | GUCGACCA | Low (495) | New lead candidate containing safe seed |
| miHDS2 | Yes | AUAGUCGC | Low (1227) | New lead caidante containing safe seed |
| miHD2.4 | Yes | UAGACAAU | Mid (4688) | Previous candidate selected at random |
| miHD82 | Yes | AUAAACCU | Mid (5041) | Previous candidate selected at random |
| mi8.2mis | No | AUAAACCU | Mid (5041) | "Same seed" control for 82 sequence |
| mi8.2-124a | No | UAAGGCAC | Mid-High (5519) | Scrambled 82 sequence containing miR-124a seed |
| miTerror | No | AAGGCAGA | High (7218) | Scrambled 8.2 sequence containing toxic seeds |
| miSafe | No | AAACGCGU | Low (662) | Random sequence with minimal off-targeting |

*Average number of transcripts containing seed hexamer complements. Three possible hexamers were considered for each 8 mer seed to account for flexibility in Drosha/Dicer processing.

TABLE 2

Off-target summary.

| Sequence | # of Off-targets* | Avg. Fold Δ |
|---|---|---|
| HD8.2 | 79 | −1.17 |
| HD2.4 | 73 | −1.17 |
| HDS1 | 7 | −1.27 |
| HDS2 | 12 | −1.17 |
| Safe | 9 | −1.18 |
| Terror | 450 | −1.26 |

(*Down-regulated genes with 8mer seed complement in 3'-UTR)

TABLE 3 miHDS sequences that effectively silence endogenous htt mRNA in HEK293 cells (human-derived)

| Artificial miRNA | Pri-miRNA Sequence | Predicted antisense RNA sequence #1 | Predicted Silencing Specificity Human (exon) | Rhesus (exon) | Mouse (exon) |
|---|---|---|---|---|---|
| miHDS.1 | 5' . . . cucgagugagcgaugcuggcucgcauggu cgauacuguaaagccacagaugggugucgaccau gcgagccagcaccgccuacuaga . . . 3' SEQ ID NO: 1 | 5'- gucgaccaugcg agccagcac-3' SEQ ID NO: 4 | Yes (44) | Yes (51) | Yes (44) |
| miHDS.2 | 5' . . . cucgagugagcgcucccggucaucagcga cuauuccguaaagccacagauggggauagucgcu gaugaccgggaucgccuacuaga . . . 3' SEQ ID NO: 2 | 5'- auagucgcugau gaccgggau-3' SEQ ID NO: 5 | Yes (61) | No | No |
| miHDS.5 | 5' . . . cucgagugagcgcuccucuuguuuacgac gugaucuguaaagccacagaugggauuacgucgu aaacaagaggaacgccuacuagu . . . 3' SEQ ID NO: 3 | 5'- uuacgucguaaa caagaggaa-3' SEQ ID NO: 6 | Yes (3'UTR-long) | No | No |

TABLE 4 miHDS sequences that effectively silence endogenous htt mRNA in HEK293 cells (human-derived)

| Artificial miRNA | Full-length Pri-miRNA Sequence |
|---|---|
| miHDS.1 | 5'-GCGUUUAGUGAACCGUCAGAUGGUACCGUUUAAACUCGAGUGAGCGAUGCUGGCUCGCAUGGUCGAUACUGUAAAGCCACAG<br>AUGGGUGUCGACCAUGCGAGCCAGCACCGCCUACUAGAGCGGCCGCCACAGCGGGGAGAUCCAGACAUGAUAAGAUACAUU-3'<br>SEQ ID NO: 10 |
| miHDS.2 | 5'-GCGUUUAGUGAACCGUCAGAUGGUACCGUUUAAACUCGAGUGAGCGCUCCCGGUCAUCAGCGACUAUUCCGUAAAGCCACAG<br>AUGGGGAUAGUCGCUGAUGACCGGGAUCGCCUACUAGAGCGGCCGCCACAGCGGGGAGAUCCAGACAUGAUAAGAUACAUU-3'<br>SEQ ID NO: 11 |
| Pri-miHDS.1 | 5'-CUCGAGUGAGCGAUGCUGGCUCGCAUGGUCGAUACUGUAAAGCCACAGAUGGGUGUCGACCAUGCGAGCCAGCACCGCCUAC<br>UAG-3'<br>SEQ ID NO: 33 |

TABLE 5

Artificial miRNA Sequences (SEQ ID NOs: 75-119, respectively, in order of appearance)

miHDS1
```
            A    A                       GUAAAG
5'. . . AGUG GCG UGCUGGCUCGCAUGGUCGAUACU       C
3'. . . UCAU CGC ACGACCGAGCGUACCAGCUGUGG       C
            C    C                       GUAGACA
Oligo 1: aaaactcgagtgagcgatgctggctcgcatggtcgatactgtaaagccacagatggg
Oligo 2: aaaaactagtaggcgtgctggctcgcatggtcgacacccatctgtggctttacag
Cumulative Distribution Antisense Seed Complements: ATGGTCGA, TGGTCGAC, GGTCGACA
``` miHDS2
```
            A    C                       GUAAAG
5'. . . AGUG GCG UCCCGGUCAUCAGCGACUAUUCC       C
3'. . . UCAU CGC AGGGCCAGUAGUCGCUGAUAGGG       C
            C    U                       GUAGACA
Oligo 1: aaaactcgagtgagcgctcccggtcatcagcgactattccgtaaagccacagatggg
Oligo 2: aaaaactagtaggcgatcccggtcatcagcgactatccccatctgtggctttacag
Cumulative Distribution Antisense Seed Complements: AGCGACTA, GCGACTAT, CGACTATC
``` miHDS3
```
            A    G                       GUAAAG
5'. . . AGUG GCG UGCUUCUUUGUCAGCGCGUUUCC       C
3'. . . UCAU CGC ACGAAGAAACAGTCGCGCAGGGG       C
            C    G                       GUAGACA
Oligo 1: aaaactcgagtgagcggtgcttctttgtcagcgcgtttccgtaaagccacagatggg
Oligo 2: aaaaactagtaggcgctgcttctttgtcagcgcgtcccccatctgtggctttacag
``` miHDS4
```
            A    A                       GUAAAG
5'. . . AGUG GCG CGGGGCAGCAGGAGCGGUAGACU       C
3'. . . UCAU CGC GCCCCGUCGUCCUCGCCAUUUGG       C
            C    C                       GUAGACA
Oligo 1: aaaactcgagtgagcgacggggcagcaggagcggtagactgtaaagccacagatggg
Oligo 2: aaaaactagtaggcggcggggcagcaggagcggtaaacccatctgtggctttacag
``` miHDS5
```
            A    C                       GUAAAG
5'. . . AGUG GCG UCCUCUUGUUUACGACGUGAUCU       C
3'. . . UCAU CGC AGGAGAACAAAUGCUGCAUUAGG       C
            C    A                       GUAGACA
Oligo 1: aaaactcgagtgagcgctcctcttgtttacgacgtgatctgtaaagccacagatggg
Oligo 2: aaaaactagtaggcgttcctcttgtttacgacgtaatcccatctgtggctttacag
``` miHDS6
```
            A    C                       GUAAAG
5'. . . AGUG GCG GGGAUGUAGAGAGGCGUUAGUCU       C
3'. . . UCAU CGC CCCUACAUCUCUCCGCAAUUAGG       C
            C    A                       GUAGACA
Oligo 1: aaaactcgagtgagcgcgggatgtagagaggcgttagtctgtaaagccacagatggg
Oligo 2: aaaaactagtaggcgtgggatgtagagaggcgttaatcccatctgtggctttacag
```

TABLE 5-continued

Artificial miRNA Sequences (SEQ ID NOs: 75-119, respectively, in order of appearance)

```
                A   C                      GUAAAG
5' . . . AGUG GCG CCCUUGGAAUGCAUAUCGUUGCU       C
3' . . . UCAU CGC GGGAACCUUACGUAUAGCGAUGG       C
                C   A                      GUAGACA
Oligo 1: aaaactcgagtgagcgccccttggaatgcatatcgttgctgtaaagccacagatggg
Oligo 2: aaaaactagtaggcgtcccttggaatgcatatcgctacccatctgtggctttacag miHDS8
                A   C                      GUAAAG
5' . . . AGUG GCG ACGUGGACCUGCCUACGGAGGCC       C
3' . . . UCAU CGC UGCACCUGGACGGAUGCCUUUGG       C
                C   U                      GUAGACA
Oligo 1: aaaactcgagtgagcgcacgtggacctgcctacggaggccgtaaagccacagatggg
Oligo 2: aaaaactagtaggcgaacgtggacctgcctacggaaacccatctgtggctttacag miHD2.4
                A   C                      GUAAAG
5' . . . AGUG GCG ACCGUGUGAAUCAUUGUCUAACU       C
3' . . . UCAU CGC UGGCACACUUAGUAACAGAUUGG       C
                C   A                      GUAGACA
Oligo 1: aaaactcgagtgagcgcaccgtgtgaatcattgtctaactgtgaagccacagatggg
Oligo 2: aaaaactagtaggcgtaccgtgtgaatcattgtctaacccatctgtggctttacag
Cumulative Distribution Antisense Seed Complements: CATTGTCT, ATTGTCTA, TTGTCTAA miHD8.2
                A   C                      GUAAAG
5' . . . AGUG GCG AGCAGCUUGUCCAGGUUUAUGCU       C
3' . . . UCAU CGC UCGUCGAACAGGUCCAAAUAUGG       C
                C   C                      GUAGACA
Oligo 1: aaaactcgagtgagcgaagcagcttgtccaggtttatgctgtgaagccacagatggg
Oligo 2: aaaaactagtaggcggagcagcttgtccaggtttatacccatctgtggctttacag
Cumulative Distribution Antisense Seed Complements: CAGGTTTA, AGGTTTAT, GGTTTATA mi8.2mis
                A   A                      GUAAAG
5' . . . AGUG GCG AGCAGCUGUGUUAGGUUUAUGCU       C
3' . . . UCAU CGC UCGUCGACACAAUCCAAAUAUGG       C
                C   C                      GUAGACA
Oligo 1: aaaactcgagtgagcgaagcagctgtgttaggtttatgctgtgaagccacagatggg
Oligo 2: aaaaactagtaggcggagcagctgtgttaggtttatacccatctgtggctttacag
Cumulative Distribution Antisense Seed Complements: TAGGTTTA, AGGTTTAT, GGTTTATA mi8.2-124a
                A   A                      GUAAAG
5' . . . AGUG GCG AGCUGUAGCUAUGUGCCUUAGCU       C
3' . . . UCAU CGC UCGACAUCGAUACACGGAAUUGG       C
                C   C                      GUAGACA
Oligo 1: aaaactcgagtgagcgaagctgtagctatgtgccttagctgtgaagccacagatggg
Oligo 2: aaaaactagtaggcggagctgtagctatgtgccttaacccatctgtggctttacag
Cumulative Distribution Antisense Seed Complements: TGTGCCTT, GTGCCTTA, TGCCTTAA miTerror
                A   C                      GUAAAG
5' . . . AGUG GCG AGCAGGAGUUAUUCUGCCUUACU       C
3' . . . UCAU CGC UCGUCCUCAAUAAGACGGAAUGG       C
                C   A                      GUAGACA
Oligo 1: aaaactcgagtgagcgcagcaggagttattctgccttactgtaaagccacagatggg
Oligo 2: aaaaactagtaggcgtagcaggagttattctgccttacccatctgtggctttacag
Cumulative Distribution Antisense Seed Complements: TTCTGCCT, TCTGCCTT, CTGCCTTA miSafe
                A   C                      GUAAAG
5' . . . AGUG GCG AGCGAACGACUUACGCGUUUACU       C
3' . . . UCAU CGC UCGCUUGCUGAAUGCGCAAAUGG       C
                C   A                      GUAGACA
Oligo 1: aaaactcgagtgagcgcagcgaacgacttacgcgtttactgtaaagccacagatggg
Oligo 2: aaaaactagtaggcgtagcgaacgacttacgcgtttacccatctgtggctttacag
Cumulative Distribution Antisense Seed Complements: TACGCGTT, ACGCGTTT, CGCGTTTA
miSCR
```

TABLE 5-continued

Artificial miRNA Sequences (SEQ ID NOs: 75-119, respectively, in order of appearance)

```
            A   C                        GUAAAG
5' . . . AGUG GCG ACCAUCGAACCGUCAGAGUUACU      C
3' . . . UCAU CGC UGGUAGCUUGGCAGUCUCAAUGG      C
            C   A                        GUAGACA
Oligo 1: aaaactcgagtgagcgcaccatcgaaccgtcagagttactgtgaagccacagatggg
Oligo 2: aaaaactagtaggcgtaccatcgaaccgtcagagttacccatctgtggctttacag
```

TABLE 6 siRNA Literature Survey

| Antisense Sequence (SEQ ID NOs: 120-199, respectively, in order of appearance) | 2-7 Seed Complement | 3-8 Seed Complement | 2-7 SC # of OTs | 3-8 SC # of OTs | Target | Reference |
|---|---|---|---|---|---|---|
| TTCGATCTGTAGCAGCAGCTT | GATCGA | AGATCG | 629 | 1104 | HTT | [1] |
| GATCCGACTCACCAATACC | TCGGAT | GTCGGA | 651 | 617 | bcl-xl | [2] |
| TTCCGAATAAACTCCAGGCTT | TTCGGA | ATTCGG | 937 | 704 | PCSK9 | [3] |
| ACGTAAACAAAGGACGTCC | TTTACG | GTTTAC | 995 | 4054 | HBV | [4] |
| AACGTTAGCTTCACCAACATT | TAACGT | CTAACG | 1112 | 668 | c-myc | 151 |
| TAACGTAACAGTCGTAAGA | TACGTT | TTACGT | 1193 | 1220 | bim | [6] |
| ACAGCGAGTTAGATAAAGC | TCGCTG | CTCGCT | 1505 | 1671 | c-myc | [7] |
| CACACGGGCACAGACTTCCAA | CCGTGT | CCCGTG | 2017 | 2023 | HTT | [1] |
| AGGTGTATCTCCTAGACACTT | TACACC | ATACAC | 2330 | 3366 | PCSK9 | [3] |
| TGTGCTACGTTCTACGAG | TAGCAC | GTAGCA | 2828 | 3383 | HCV | [8] |
| TGTGGACAAAGTCTCTTCC | GTCCAC | TGTCCA | 2930 | 4899 | Livin | [9] |
| TGATGTCATAGATTGGACT | GACATC | TGACAT | 3143 | 5012 | CCR5 | [10] |
| TCTGATCTGTAGCAGCAGCTT | GATCAG | AGATCA | 3261 | 4214 | HTT | [1] |
| GGTAAGTGGCCATCCAAGC | ACTTAC | CACTTA | 3268 | 4049 | bcl-xl | [2] |
| CGAGTTAGATAAAGCCCCG | TAACTC | CTAACT | 3319 | 3265 | c-myc | [7] |
| TTAACCTAATCTCCTCCCC | AGGTTA | TAGGTT | 3323 | 3480 | HBV | [4] |
| TGATGATGGTGCGCAGACC | ATCATC | CATCAT | 3496 | 4415 | HBV | [4] |
| TATAGAGAGAGAGAAGA | CTCTAT | TCTCTA | 3586 | 5271 | K6a | [11] |
| TTGATCCGGAGGTAGGTCTTT | GGATCA | CGGATC | 3593 | 859 | PLK1 | [12] |
| TTGGTATTCAGTGTGATGA | ATACCA | AATACC | 3636 | 3304 | APOB | [13] |
| TTACTCTCAAACTTTCCTC | AGAGTA | GAGAGT | 3768 | 3885 | XIAP | [9] |
| TATTGTAATGGGCTCTGTC | TACAAT | TTACAA | 4118 | 5055 | E6/E7 | [14] |
| TGCCTIGGCAAACTITCTT | CAAGGC | CCAAGG | 4247 | 5408 | EGFR1 | [15] |
| ACCAATTTATGCCTACAGC | AATTGG | AAATTG | 4273 | 6322 | HBV | [4] |
| TTTGCTCTGTAGCAGCAGCTT | GAGCAA | AGAGCA | 4298 | 5604 | HTT | [1] |
| CCAATCTCAAAGTCATCAA | AGATTG | GAGATT | 4391 | 4652 | AuRkb | [15] |
| TAGTTATTCAGGAAGTCTA | ATAACT | AATAAC | 4421 | 4198 | APOB | [13] |
| AATCAAGTAGATCCTCCTCC | CTTGAT | ACTTGA | 4458 | 5308 | AuRkb | [15] |
| TGCATCTCCTTGTCTACGC | AGATGC | GAGATG | 4488 | 5464 | bcl-xl | [2] |

TABLE 6-continued siRNA Literature Survey

| Antisense Sequence (SEQ ID NOs: 120-199, respectively, in order of appearance) | 2-7 Seed Complement | 3-8 Seed Complement | 2-7 SC # of OTs | 3-8 SC # of OTs | Target | Reference |
|---|---|---|---|---|---|---|
| TCAAGCTCTGCAAACCAGA | AGCTTG | GAGCTT | 4547 | 4427 | CCR5 | [10] |
| ATGATGATGGTGCGCAGAC | TCATCA | ATCATC | 4561 | 3496 | HBV | [4] |
| TCTTCTAGCGTTGAAGTACTG | TAGAAG | CTAGAA | 4583 | 4684 | HTT | [1] |
| TCTTCTAGCGTTGAATTACTG | TAGAAG | CTAGAA | 4583 | 4684 | HTT | [1] |
| GAATTGTTGCTGGTTGCACTC | ACAATT | AACAAT | 4647 | 4904 | EGFR1 | [15] |
| TAGGACTAGTCACTTGTGC | AGTCCT | TAGTCC | 4652 | 2822 | K6a | [11] |
| TATAATGCTCAGCCTCAGA | CATTAT | GCATTA | 4672 | 3567 | K6a | [11] |
| TTTGATTTGTAGCAGCAGCTT | AATCAA | AAATCA | 4735 | 6429 | HTT | [1] |
| TTTTATCTGTAGCAGCAGCTT | GATAAA | AGATCA | 4785 | 4877 | HTT | [1] |
| GAGTCTCTTGTTCCGAAGC | GAGACT | AGAGAC | 4790 | 5151 | VEGF | [16] |
| TATCACTCTATTCTGTCTC | AGTGAT | GAGTGA | 4846 | 4396 | Survivin | [9] |
| TCACCTTCAAACTATGTCC | AAGGTG | GAAGGT | 4852 | 4063 | XIAP | [9] |
| ATTGTCTTCAGGTCTTCAGTT | AGACAA | AAGACA | 4855 | 5748 | KSP | [12] |
| GCACTCCAGGGCTTCATCG | GGAGTG | TGGAGT | 4944 | 5515 | VEGF | [16] |
| AAGCCCCGAAAACCGGCTT | GGGGCT | CGGGGC | 5090 | 2013 | c-myc | [7] |
| TTGTCCAGGAAGTCCTCAAGTCT | TGGACA | CTGGAC | 5201 | 4750 | PKN3 | [17] |
| CCAAGGCTCTAGGTGGTCA | GCCTTG | AGCCTT | 5235 | 5726 | bcl-xl | [2] |
| GCACCACTAGTIGGTIGTC | GTGGTG | AGTGGT | 5363 | 4425 | TNFa | [18] |
| TCATCTCAGCCACTCTGCTTT | GAGATG | TGAGAT | 5464 | 5351 | DYT1 | [19] |
| GTCATCTCAGCCACTCTGCTT | AGATGA | GAGATG | 5535 | 5464 | DYT1 | [19] |
| AATGCAGTATACT1CCTGA | CTGCAT | ACTGCA | 5549 | 6053 | HIV | [10] |
| CACAATGGCACAGACTTCCAA | CATTGT | CCATTG | 5565 | 4226 | HTT | [1] |
| CACAATGGCGCAGACTTCCAA | CATTGT | CCATTG | 5565 | 4226 | HTT | [1] |
| TCTCCTCAGCCACTCTGCTTT | GAGGAG | TGAGGA | 5692 | 5714 | DYT1 | [19] |
| CTCCTCAGCCACTCTGCTTTT | TGAGGA | CTGAGG | 5714 | 6646 | DYT1 | [19] |
| TTCCTCAAATTCTTTCTTC | TGAGGA | TTGAGG | 5714 | 5047 | Survivin | [9] |
| TTGTACATCATAGGACTAG | TGTACA | ATGTAC | 5725 | 4158 | K6a | [11] |
| TTGTCTTTGAGATCCATGC | AAGACA | AAAGAC | 5748 | 5347 | TNFa | [18] |
| TCAGCCCACACACAGTGCTTTG | GGGCTG | TGGGCT | 5938 | 5481 | ID2 | [20] |
| TAACAAGCCAGAGTTGGTC | CTTGTT | GCTTGT | 6008 | 4183 | MAP4K4 | [18] |
| TTCCAGAATTGATACTGACTT | TCTGGA | TTCTGG | 6027 | 6482 | CCR5 | [21] |
| TTTCCCTTGGCCACTTCTG | AGGGAA | AAGGGA | 6352 | 5684 | MAP4K4 | [18] |
| AAGCAGAGTTCAAAAGCCCTT | TCTGCT | CTCTGC | 6576 | 6743 | bcr-abl | [22] |
| TTGGGGATAGGCTGTCGCC | TCCCCA | ATCCCC | 6591 | 3615 | HCV | [23] |
| ATCTTCAATAGACACATCGGC | TGAAGA | TTGAAG | 6618 | 5729 | SOD1 | [24] |
| TTCCCCAGCTCTCCCAGGC | TGGGGA | CTGGGG | 6649 | 6671 | CCR5 | [10] |

TABLE 6-continued siRNA Literature Survey

| Antisense Sequence (SEQ ID NOs: 120-199, respectively, in order of appearance) | 2-7 Seed Complement | 3-8 Seed Complement | 2-7 SC # of OTs | 3-8 SC # of OTs | Target | Reference |
|---|---|---|---|---|---|---|
| TTCCCCAAACCTGAAGCTC | TGGGGA | TTGGGG | 6649 | 6070 | HIV | [10] |
| TTCTTCTCATTTCGACACC | AGAAGA | GAGAAG | 6650 | 6048 | CCR5 | [10] |
| GTCCTGGATGATGATGTTC | CCAGGA | TCCAGG | 6819 | 5883 | VEGF | [16] |
| ATTTCAGGAATTGTTAAAG | CTGAAA | CCTGAA | 6935 | 5757 | APOB | [13] |
| CTTTCAGACTGGACCTCTC | CTGAAA | TCTGAA | 6935 | 6689 | Livin | [9] |
| ACTGAGGAGTCTCTTGATCTT | CCTCAG | TCCTCA | 6986 | 5833 | CD4 | [21] |
| AAGCAAAACAGGTCTAGAATT | TTTGCT | TTTTGC | 7110 | 6603 | PCSK9 | [3] |
| CCCTCCCTCCGTTCTTTIT | GGGAGG | AGGGAG | 7153 | 6058 | c-myc | [7] |
| GTTGTTTGCAGCTCTGTGC | AAACAA | CAAACA | 7213 | 5301 | E6/E7 | [14] |
| ATTCTCTCTGACTCCTCTC | AGAGAA | GAGAGA | 7338 | 5454 | CCR5 | [10] |
| TAATACAAAGACCTTTAAC | TGTATT | TTGTAT | 7651 | 6954 | HBV | [4] |
| TATTTAAGGAGGGTGATCTTT | TTAAAT | CTTAAA | 7880 | 6154 | PLK1 | [12] |
| AAGAAATCATGAACACCGC | ATTTCT | GATTTC | 8000 | 4935 | ID2 | [20] |
| TAAACAAAGGACGTCCCGC | TTGTTT | TTTGTT | 8980 | 8926 | HBV | [4] |
| AATTTTTCAAAGTTCCAAT | AAAAAT | GAAAAA | 9678 | 8159 | APOB | [13] |

REFERENCES CITED IN TABLE 6
1. Pfister, et al. (2009). Five siRNAs targeting three SNPs may provide therapy for three-quarters of Huntington's disease patients. Curr Biol 19(9): 774-8.
2. Mu, et al. (2009). Systemic delivery of siRNA specific to tumor mediated by atelocollagen: combined therapy using siRNA targeting Bcl-xL and cisplatin against prostate cancer. Int J Cancer 125(12): 2978-90.
3. Frank-Kamenetsky, et al. (2008). Therapeutic RNAi targeting PCSK9 acutely lowers plasma cholesterol in rodents and LDL cholesterol in nonhuman primates. Proc Natl Acad Sci U S A 105(33): 11915-20.
4. Carmona, et al. (2009). Controlling HBV replication in vivo by intravenous administration of triggered PEGylated siRNA-nanoparticles. Mol Pharm 6(3): 706-17.
5. Chen, Y., J. J. Wu, and L. Huang (2010). Nanoparticles targeted with NGR motif deliver c-myc siRNA and doxorubicin for anticancer therapy. Mol Ther 18(4): 828-34.
6. Schwulst, et al. (2008). Bim siRNA decreases lymphocyte apoptosis and improves survival in sepsis. Shock 30(2): 127-34.
7. Napoli, et al. (2009). Promoter-specific transcriptional interference and c-myc gene silencing by siRNAs in human cells. Embo J 28(12): 1708-19.
8. Yokota, et al. (2007). Efficient regulation of viral replication by siRNA in a non-human primate surrogate model for hepatitis C. Biochem Biophys Res Commun 361(2): 294-300.
9. Yang, et al. (2010). Therapeutic potential of siRNA-mediated combined knockdown of the IAP genes (Livin, XIAP, and Survivin) on human bladder cancer T24 cells. Acta Biochim Biophys Sin (Shanghai) 42(2): 137-44.
10. Ehsani, et al. (2010). Rational design of micro-RNA-like bifunctional siRNAs targeting HIV and the HIV coreceptor CCR5. Mol Ther 18(4): 796-802.
11. Smith, et al. (2008). Development of therapeutic siRNAs for *pachyonychia congenita*. J Invest Dermatol 128(1): 50-8.
12. Judge, et al. (2009). Confirming the RNAi-mediated mechanism of action of siRNA-based cancer therapeutics in mice. J Clin Invest 119(3): 661-73.
13. Burchard, J., A. L. Jackson, V. Malkov, R. H. Needham, Y. Tan, S. R. Bartz, et al. (2009). MicroRNA-like off-target transcript regulation by siRNAs is species specific. Rna 15(2): 308-15.
14. Jonson, et al. (2008). Gene silencing with siRNA targeting E6/E7 as a therapeutic intervention in a mouse model of cervical cancer. Gynecol Oncol 111(2): 356-64.
15. Addepalli, et al. (2010). RNAi-mediated knockdown of AURKB and EGFR shows enhanced therapeutic efficacy in prostate tumor regression. Gene Ther 17(3): 352-9.
16. Li, S. D., S. Chono, and L. Huang (2008). Efficient oncogene silencing and metastasis inhibition via systemic delivery of siRNA. Mol Ther 16(5): 942-6.
17. Aleku, et al. (2008). Atu027, a liposomal small interfering RNA formulation targeting protein kinase N3, inhibits cancer progression. Cancer Res 68(23): 9788-98.
18. Aouadi, et al. (2009). Orally delivered siRNA targeting macrophage Map4k4 suppresses systemic inflammation. Nature 458(7242): 1180-4.
19. Hewett, et al. (2008). siRNA knock-down of mutant torsinA restores processing through secretory pathway in DYT1 dystonia cells. Hum Mol Genet 17(10): 1436-45.
20. Gray, et al. (2008). Therapeutic targeting of Id2 reduces growth of human colorectal carcinoma in the murine liver. Oncogene 27(57): 7192-200.
21. Kim, et al. (2010). RNAi-mediated CCR5 silencing by LFA-1-targeted nanoparticles prevents HIV infection in BLT mice. Mol Ther 18(2): 370-6.
22. Koldehoff, et al. (2007). Therapeutic application of small interfering RNA directed against bcr-abl transcripts to a patient with imatinib-resistant chronic myeloid leukaemia. Clin Exp Med 7(2): 47-55.
23. Kim, et al. (2009). Targeted delivery of siRNA against hepatitis C virus by apolipoprotein A-I-bound cationic liposomes. J Hepatol 50(3): 479-88.
24. Wang, et al. (2008). Therapeutic gene silencing delivered by a chemically modified small interfering RNA against mutant SOD1 slows amyotrophic lateral sclerosis progression. J Biol Chem 283(23): 15845-52.

Example 2

Therapeutic siRNAs

Using the method described in Example 1 above, additional "safe seed" sequences were determined for the target genes indicated in Table 7 below.

TABLE 7

| ID NO. | Target Gene | Human Target site | SEQ ID NO |
|---|---|---|---|
| HDS1 | HTT | GTCGTGGCTCGCATGGTCGAT | SEQ ID NO: 34 |
| HDS2 | HTT | ATCCCGGTCATCAGCGACTAT | SEQ ID NO: 35 |
| HDS3 | HTT | CTGCTTCTTTGTCAGCGCGTC | SEQ ID NO: 36 |
| HDS4 | HTT | GCGGGGCAGCAGGAGCGGTAG | SEQ ID NO: 37 |
| HDS5 | HTT | TTCCTCTTGTTTACGACGTGA | SEQ ID NO: 38 |
| HDS6 | HTT | TGGGATGTAGAGAGGCGTTAG | SEQ ID NO: 39 |
| HDS7 | HTT | TCCCTTGGAATGCATATCGCT | SEQ ID NO: 40 |
| HDS8 | HTT | AACGTGGACCTGCCTACGGAG | SEQ ID NO: 41 |
| HDS9 | HTT | AGGGACAGTACTTCAACGCTA | SEQ ID NO: 42 |
| HDS10 | HTT | TGGGGACAGTACTTCAACGCT | SEQ ID NO: 43 |
| HDS11 | HTT | AAGGAGTTCATCTACCGCATC | SEQ ID NO: 44 |
| HDS12 | HTT | GAGCTGGCTCACCTGGTTCGG | SEQ ID NO: 45 |
| HDS13 | HTT | CTGCCCCAGTTTCTAGACGAC | SEQ ID NO: 46 |
| HDS14 | HTT | TGCCCCAGTTTCTAGACGACT | SEQ ID NO: 47 |
| HDS15 | HTT | GCCCCAGTTTCTAGACGACTT | SEQ ID NO: 48 |
| HDS16 | HTT | CCCCAGTTTCTAGACGACTTC | SEQ ID NO: 49 |
| HDS17 | HTT | CAGCTACCAAGAAAGACCGTG | SEQ ID NO: 50 |
| HDS18 | HTT | CTGCTGTGCAGTGATGACGCA | SEQ ID NO: 51 |
| HDS19 | HTT | ATGGAGACCCACAGGTTCGAG | SEQ ID NO: 52 |
| HDS20 | HTT | TTCCGTGTGCTGGCTCGCATG | SEQ ID NO: 53 |
| HDS21 | HTT | TCCGTGTGCTGGCTCGCATGG | SEQ ID NO: 54 |
| HDS22 | HTT | CTGGCTCGCATGGTCGACATC | SEQ ID NO: 55 |
| HDS23 | HTT | CACCCTTCAGAAGACGAGATC | SEQ ID NO: 56 |
| HDS24 | HTT | AACCTTTTCTGCCTGGTCGCC | SEQ ID NO: 57 |
| HDS25 | HTT | GAGGATGACTCTGAATCGAGA | SEQ ID NO: 58 |
| HDS26 | HTT | CCGGACAAAGACTGGTACGTT | SEQ ID NO: 59 |
| SCA1.S1 | ATXN1 | AAGCAACGACCTGAAGATCGA | SEQ ID NO: 60 |
| SCA1.S2 | ATXN1 | CTGAGAAGTCAGAAGACGAA | SEQ ID NO: 61 |
| SCA1.S3 | ATXN1 | AACCAAGAGCGGAGCAACGAA | SEQ ID NO: 62 |
| SCA7.S1 | ATXN7 | ACGGGACAGAATTGGACGAAA | SEQ ID NO: 63 |
| SCA7.S2 | ATXN7 | GTGGAAAAGATTCATCCGAAA | SEQ ID NO: 64 |
| SCA7.S3 | ATXN7 | CAGGGTAGAAGAAAACGATTT | SEQ ID NO: 65 |
| SCA7.S4 | ATXN7 | CGGCTCAGGAAAGAAACGCAA | SEQ ID NO: 66 |
| SCA2.S1 | ATXN2 | CCCCACATGGCCCACGTACCT | SEQ ID NO: 67 |
| SCA2.S2 | ATXN2 | ATCCAACTGCCCATGCGCCAA | SEQ ID NO: 68 |
| SCA2.S3 | ATXN2 | CGCCAATGATGCTAATGACGA | SEQ ID NO: 69 |
| SCA2.S4 | ATXN2 | CAGCCCATTCCAGTCTCGACA | SEQ ID NO: 70 |
| SCA2.S5 | ATXN2 | ACCCCACATGGCCCACGTACC | SEQ ID NO: 71 |
| SCA2.S6 | ATXN2 | AGCCCATTCCAGTCTCGACAA | SEQ ID NO: 72 |
| SCA2.S7 | ATXN2 | TCCCAATGATATGTTTCGATA | SEQ ID NO: 73 |
| SCA2.S8 | ATXN2 | TCCCAATGATATGTTTCGATA | SEQ ID NO: 74 |

Example 3

Preclinical Safety of RNAi-Mediated HTT Suppression in the Rhesus Macaque as a Potential Therapy for Huntington's To date, a therapy for Huntington's disease (HD), a genetic, neurodegenerative disorder, remains elusive. HD is characterized by cell loss in the basal ganglia, with particular damage to the putamen, an area of the brain responsible for initiating and refining motor movements. Consequently, patients exhibit a hyperkinetic movement disorder. RNA interference (RNAi) offers therapeutic potential for this disorder by reducing the expression of HTT, the disease-causing gene. We have previously demonstrated that partial suppression of both wild-type and mutant HTT in the striatum prevents behavioral and neuropathological abnormalities in rodent models of HD. However, given the role of HTT in various cellular processes, it remains unknown whether a partial suppression of both alleles will be safe in mammals whose neurophysiology, basal ganglia anatomy, and behavioral repertoire more closely resembles that of a human. Here, we investigate whether a partial reduction of HTT in the normal non-human primate putamen is safe. We demonstrate that a 45% reduction of rhesus HTT expression in the mid- and caudal putamen does not induce motor deficits, neuronal degeneration, astrogliosis, or an immune response. Together, these data suggest that partial suppression of wild-type HTT expression is well tolerated in the primate putamen and further supports RNAi as a therapy for HD.

Huntington's disease (HD) is a fatal, dominantly inherited, neurodegenerative disorder caused by an expanded trinucleotide (CAG) mutation in the HTT gene on chromosome 4. The encoded protein, mutant huntingtin (mHTT), contains an expanded polyglutamine stretch at the N-terminus, conferring a toxic gain of function. Over time, mHTT induces the formation of inclusions, cellular dysfunction, and neurodegeneration throughout the basal ganglia and overlaying cortex. Cell loss in HD is accompanied with upregulation of reactive astrocytes (astrogliosis) and activation of microglia, the resident immune cells of the brain. Although cell loss is observed in multiple brain regions, neuropathology is most pronounced in the medium-sized spiny neurons of the putamen and the caudate, regions of the brain which are critical for the initiation and refinement of motor programs, procedural learning, and various aspects of cognitive function. Accordingly, HD patients are afflicted with involuntary hyperkinetic movements of the torso, arms, legs, and face (known as chorea) with concomitant gait and coordination difficulties, working memory deficits, and a variety of emotional disturbances.

To date, HD remains incurable. While several therapies have shown promise in rodent models of the disease, including glutamate antagonists, bioenergetic supplements, caspase inhibitors, antihistaminergic agents (HORIZON trial) and fetal tissue transplantation, none have made a significant impact on disease prevention or extension of life span when evaluated in clinical trials. As a result, current treatment strategies are primarily aimed at palliative care to treat disease symptoms and improve end-stage quality of life measures. With the elucidation of the causative HD mutation in 1993, therapies can now be tailored toward reducing expression of the deleterious gene itself, which may have a higher clinical impact compared to strategies aimed at targeting downstream consequences of mHTT.

Recently, it has become clear that endogenous, small microRNAs (miRNAs) play a vital role in regulating the expression of genes during development, throughout adulthood and can contribute to disease states. Endogenous miRNA machinery can be co-opted and used to suppress genes of interest. Exogenous expression of engineered miRNAs as triggers for RNA interference (RNAi) confers a robust decrease in gene expression and has been investigated as a therapeutic tool to silence expression of disease alleles. Inarguably, the preferred mechanism to treat HD would be to specifically target the mutant allele while leaving the normal allele intact. As a proof-of-principle, the benefit of allele-specific silencing has been demonstrated by our laboratory members and others in rodent models of HD, wherein inhibitory RNAs were designed to silence the human mHTT transgene and not endogenous mouse Htt. (Huang, et al. (2007). High-capacity adenoviral vector-mediated reduction of huntingtin aggregate load in vitro and in vivo. *Hum Gene Ther* 18: 303-311; Franich et al. (2008). AAV vector-mediated RNAi of mutant huntingtin expression is neuroprotective in a novel genetic rat model of Huntington's disease. *Mol Ther* 16: 947-956; Harper et al. (2005). RNA interference improves motor and neuropathological abnormalities in a Huntington's disease mouse model. *Proc Natl Acad Sci USA* 102: 5820-5825) Additionally, several single nucleotide polymorphisms (SNPs) that differentiate up to 80% of diseased and normal alleles have been identified in the human population. (Pfister, et al. (2009). Five siRNAs targeting three SNPs may provide therapy for three-quarters of Huntington's disease patients. *Curr Biol* 19: 774-778) However, the utility of these SNPs for RNAi-based silencing strategies have not been tested in vivo and importantly, will be unusable for a significant number of HD patients.

Thus, an alternative strategy is to partially reduce expression of both the mutant and normal allele in regions of the brain most affected by the disease, a therapy that would be applicable to all HD patients. Because normal HTT has been found to play a functional role in the adult brain, with proposed roles in mediating transcription and axonal transport, nonallele-specific RNAi treatment for HD must demonstrate therapeutic benefit of reducing the mutant allele, as well as the safety and tolerability of partially suppressing the normal allele. Over the past half-decade, we have used recombinant adeno-associated viral vectors (rAAV) to deliver RNAi silencing constructs to the striatum and showed that a 60% reduction of human mHTT and endogenous wild-type mouse Htt was well tolerated and prevented motor and neuropathological deficits in transgenic mouse models of HD. Additionally, lentiviral delivery of inhibitory RNAs in a rat model of HD conferred a 35% knockdown of Htt gene expression (both mutant and wild-type alleles) and was safe and beneficial (both neuroanatomical and behavioral benefits) out to 9 months after injection. Furthermore, heterozygous Htt knockout mice are phenotypically normal, and humans with only one copy of HTT (50% reduction of normal HTT production) show no abnormal behavioral deficits, suggesting that nonallele-specific reduction of HTT expression may be safe.

While findings from rodent models are encouraging, it is essential to evaluate the safety of partial HTT suppression in an animal that more closely resembles humans with regards to the size, anatomy, and neurophysiology of its basal ganglia as well as its behavioral capabilities prior to RNAi evaluation in human HD patients. Therefore, in this study, we assessed the safety of reduced HTT expression in the rhesus macaque putamen. We demonstrate a partial, sustained HTT reduction in the putamen without the development of abnormal motor phenotypes, altered circadian behavior, fine motor skill deficits, neuronal loss, gliosis, or an immune response, thus bringing RNAi closer to the clinic as a potential therapy for HD.

Results

AAV2/1 Distribution and HTT Suppression in the Putamen

A sequence that silences mouse, rhesus, and human HTT and a control sequence were cloned into an artificial miRNA backbone based on miR-30 and subsequently cloned into AAV, serotype 1, vectors. (Boudreau, R L, Monteys, A M and Davidson, B L (2008). Minimizing variables among hairpin-based RNAi vectors reveals the potency of shRNAs. *RNA* 14: 1834-1844) Expression of the HD-specific miRNA (miHDS1) and the control miRNA (miCONT) was driven by a mouse U6 promoter. Enhanced GFP (eGFP) was driven from a cytomegalovirus (CMV) promoter to allow for assessment of vector distribution following injection into the putamen. Both miHDS1 (targeting a sequence in exon 52 of rhesus HTT mRNA) and miCONT (a control miRNA) were designed using "safe seed" guidelines to optimize safety and minimize potential off-target gene silencing.

Prior to in vivo assessment in the rhesus macaque putamen, we first verified HTT mRNA suppression by in vitro transfection of AAV shuttle plasmids expressing miHDS1, miCONT, or eGFP in human HEK293 cells as well as rhesus primary fibroblasts generated at the Oregon National Primate Research Center (50% and 32% reduction of relative HTT/1.8S mRNA expression, respectively). Additionally, 60% silencing of striatal Htt mRNA expression, without toxicity, was verified 4 weeks following injection of AAV2/1-miHDS1 injections into both wild-type and BACHD transgenic mice.

Following verification of effective HTT mRNA suppression in vitro and in mice, eleven rhesus macaques received bilateral, MRI-guided stereotaxic injections of either AAV2/1-miHDS1eGFP (therapeutic miRNA, n=4), AAV2/1-miCONT-eGFP (control miRNA, n=4) or AAV-eGFP (viral vector control, n=3) into the commissural and postcommissural putamen (posterior half of the entire putamen). Animals were assessed prior to and for six weeks postsurgery on a variety of general behavior and motor skill assays and euthanized for molecular (tissue punches taken from the left hemisphere) and histological analyses (immuno-stained sections through the right hemisphere). Putamen samples transduced with AAV2/1 (2×4 mm) were obtained from the left hemisphere of unfixed, coronal brain slabs at necropsy. Quantitative polymerase chain reaction (QPCR) using primers flanking the miHDS1 targeting site in exon 52 demonstrated a significant reduction of rhesus HTT mRNA transcripts (45%, $P<0.01$) following injection with AAV1-miHDS1 compared to AAV-eGFP control-treated putamen. We have previously demonstrated, in separate experiments, that similar levels of silencing of either mutant human or wild-type Htt transcripts in mouse striatum cause marked reductions in the respective proteins. (McBride et al. (2008). Artificial miRNAs mitigate shRNA-mediated toxicity in the brain: implications for the therapeutic development of RNAi. *Proc Natl Acad Sci USA* 105: 5868-5873; Boudreau et al. (2009). Nonallele-specific silencing of mutant and wild-type huntingtin demonstrates therapeutic efficacy in Huntington's disease mice. *Mol Ther* 17: 1053-1063) eGFP immunohistochemistry was conducted to assess viral vector distribution throughout the basal ganglia. eGFP-positive cells were observed throughout the mid- and posterior putamen, indicating accurate needle placements during surgery. Immunofluorescence staining, using eGFP fluorescence as a reference, demonstrated AAV2/1 transduction in dopamine- and cAMP-regulated neuronal phosphoprotein (DARPP-32)-positive medium spiny projection neurons, choline acetyltransferase (ChAT)-positive large, cholinergic interneurons, and glial fibrillary acid protein (GFAP)-positive astrocytes throughout the putamen. eGFP-positive cells did not co-localize with IBA-1-stained microglia. In addition to eGFP-positive neurons, astrocytes and fibers observed in the putamen, eGFP-positive cell bodies, and fibers were also seen in other regions of the basal ganglia which receive projections from and project to the putamen. These include the internal and external segments of the globus pallidus), the subthalamic nucleus (fibers only), and the substantia nigra pars reticulata. eGFP expression in the cortex was limited to the needle tracts, suggesting that AAV2/1 was not transported anterogradily and retrogradily to the cortex, as was observed in other regions.

Unbiased stereology was employed to quantify the area fraction of putamen containing eGFP-positive cells and fibers using serial sections stained with anti-eGFP antibody. Results demonstrated an area fraction of eGFP-positive cells in the commissural and postcommissural putamen of 30±2.0% for AAV-eGFPinjected animals, 29±3.0% for AAV-miCONT-injected animals, and 30±3.0% for AAV-miHDS1 animals with no significant differences between groups (P>0.05). Additionally, quantification of the estimated volume of putamen containing eGFP-positive cells and fibers was performed. The mean estimated volume of transduced putamen was 1.0e11±1.7e10 $\mu m^3$ for AAVGFP-injected animals, 8.5e10±5.6e9 $\mu m^3$ for AAV-miCONT injected animals, and 9.9e10±1.6e10 $\mu m^3$ for AAV-miHDS1 animals. No significant difference in volume was found between treatment groups (P>0.05). A three-dimensional model of AAV2/1-transduced putamen (right hemisphere only) was created for each animal using Stereo Investigator software. The 3D rendering allows for the visualization of the three injection sites as well as the spread of vector following surgery. The anterior-posterior (A-P) distribution of eGFP-positive cells, a one-dimensional measure of AAV2/1 distribution from rostral to caudal, was determined from one hemisphere of each of the eleven AAV2/1-injected animals. The mean A-P distribution for transduced putamen was 10.0±1.0 mm for AAV-GFP-injected animals, 9.5e10±1.0 mm for AAV-miCONT animals, and 9.5±0.58 mm for AAV-miHDS1 animals with no significant differences in spread between groups (Table 8, P>0.05).

TABLE 8

Measurement of anterior-posterior spread of eGFP-positive regions of the putamen in individual animals injected with AAV2/1-eGFP (n = 3), AAV-miHds1 (n = 4), or AAV2/1-micont (n = 4)

| Animal Id | Group | AP spread (mm) |
|---|---|---|
| Rh24522 | AAV2/1-eGFP | 10.0 |
| Rh24906 | AAV2/1-eGFP | 9.0 |
| Rh25433 | AAV2/1-eGFP | 11.0 |
| Mean ± SD | | 10 ± 1.0 |
| Rh24277 | AAV2/1-miHDS1 | 10.0 |
| Rh24353 | AAV2/1-miHDS1 | 9.0 |
| Rh24530 | AAV2/1-miHDS1 | 9.0 |
| Rh25300 | AAV2/1-miHDS1 | 10.0 |
| Mean ± SD | | 9.5 ± 0.58 |
| Rh24377 | AAV2/1-miCONT | 9.0 |
| Rh25150 | AAV2/1-miCONT | 11.0 |
| Rh25388 | AAV2/1-miCONT | 9.0 |
| Rh25416 | AAV2/1-miCONT | 9.0 |
| Mean ± SD | | 9.5 ± 1.0 |

HTT Suppression does not Induce Motor Skill Deficits

To assess whether partial HTT suppression in the putamen, a region of the brain heavily involved in initiating, executing, and refining motor movement, induces motor perturbations, a variety of behavioral assays were used to evaluate the monkeys prior to and for six weeks following surgery. We chose behavioral assays that allowed for the detection of changes in whole body movements in the homecage over 24-hour spans, more specific coordinated movements of the arms and legs and learned tasks requiring higher levels of dexterity of the forearms and digits.

To collect daytime and nighttime homecage activity, animals were fitted with nylon or aluminum collars that housed an enclosed Actical accelerometer. All monkeys wore activity collars for 3 weeks prior to surgery. The Actical monitor contains an omnidirectional sensor that integrates the speed and distance of acceleration and produces an electrical current that varies in magnitude depending on a change in acceleration. The monitors were programmed to store the total number of activity counts during each 1-minute epoch. For daytime activity, a repeated measures ANOVA failed to detect significant differences between treatment groups, F (2.64) =0.17, P=0.84, suggesting that a partial reduction of HTT in the commissural and postcommissural putamen does not alter general homecage activity levels compared to controls. A significant effect was indicated for time, F (8.64)=2.4, P<0.05, and Holms-Sidak pairwise comparisons showed that daytime activity during the week immediately following surgery (+1) was significantly less than the activity exhibited during week −2 (P<0.001) or week +5 (P<0.001), likely owing to a small decrease in overall daytime activity while animals recovered from surgery. No group differences were observed (P=0.45). Likewise, for night time homecage activity, a repeated measures ANOVA indicated no significant differences between treatment groups F (2.64)=0.189, P=0.83, nor over time F (8.64)=1.43, P=0.20. Similarly, no interaction was indicated (P=0.64). In addition to overall circadian homecage activity, body weight from each animal was recorded at surgery and at necropsy, and no decrease in weight was detected in any animal (P>0.05).

Potential changes in fine motor skills of left and right forelimbs and digits were assessed using the Lifesaver test of manual dexterity originally described by Bachevalier et al. (1991, Agen monkeys exhibit behavioral deficits indicative of widespread cerebral dysfunction. *Neurobiol Aging* 12: 99-111) and further modified by Gash and colleagues (1999, An automated movement assessment panel for upper limb motor functions in rhesus monkeys and humans. *J. Neurosci Methods*, 89: 111-117). Animals were transported from their homecage to a Wisconsin General Testing Apparatus in a separate behavioral room and trained to remove hard, round treats from a straight medal rod (straight post). For the straight post, animals were assessed 2 weeks prior to surgery to collect baseline data and weekly for 6 weeks after surgery (two trials per forelimb each day, twice a week). No statistical difference was detected in the latencies to remove stimuli from posts between the right and left hands. Consequently, the right and left hand data were collapsed, and averages were used for all analyses. A repeated measures, two-way ANOVA indicated a significant main effect of time over the testing trials, F (6.48)=27.5, P<0.0001, indicating that animals from all treatment groups removed the treat from the post with shorter latencies (faster performance) as the study progressed. By contrast, no significant effects were found between the treatment groups, F (2.48)=0.07, P=0.99, nor for an interaction (P=0.55), indicating that AAV-miHDS1-treated animals performed with the same speeds as animals from both control groups. For the Lifesaver task using the question mark shaped post, animals received no training prior to surgery so that we could assess each animal's ability to learn a new and more difficult task (procedural learning) following AAV-miHDS1 injection into the putamen. Beginning 2 weeks following surgery and each week thereafter, latencies to successfully remove each treat off the question mark shaped post were recorded (two trials per forelimb each day, twice a week). A repeated measures two-way ANOVA failed to indicate significant differences between groups, F (2.28)=0.573, P=0.58, or over testing trials, F (4.28)=0.61, P=0.652 nor for an interaction (P=0.93). These data show that animals from all treatment groups were able to complete the question mark post task with equal speed and that HTT suppression did not alter the ability of the AAV-HDS1-treated animals to (1) learn a new behavioral task or (2) exhibit fine motor skills on a difficult task compared to controls.

Additionally, we developed a non-human primate-specific, preclinical motor rating scale (MRS) that was modified from the Unified Huntington's Disease Rating Scale used for evaluating motor performance in HD patients. We designed the MRS to specifically assess putamen-based behavioral phenotypes in monkeys including horizontal and vertical ocular pursuit, treat retrieval with both forelimbs, ability to bear weight on both hindlimbs, posture, balance, and startle response. In addition, the scale includes negative motor phenotypes seen in HD or cases of putamen dysfunction including bradykinesia (slowness of movement), dystonia (involuntary, sustained muscle contraction), and chorea (involuntary, hyperkinetic movement) of each limb and trunk. Possible scores ranged from 0 (normal phenotype) to 3 (severely abnormal phenotype) for a total of 72 possible points. Animals were rated by three, independent observers blind to treatment group and familiar with nonhuman primate behavioral repertoires; inter-rater reliability was 100%. All animals were evaluated in their homecage and were rated once prior to surgery and each week thereafter for the duration of the study. Kruskal-Wallis statistical analysis revealed a significant difference between the three treatment groups (H(2)=9.30, P=0.010). However, this difference is due to one AAVmi-CONT-injected animal that exhibited a very mild but progressive dystonia in one hind leg (animal 25150). A Dunn's pairwise comparison shows no difference between AAV-miHDS1-injected animals compared to AAV-eGFP-injected controls, demonstrating that a partial HTT suppression in the mid- and posterior putamen did not alter normal putamen-based behavior nor induce diseased phenotypes commonly seen with neuronal dysfunction or degeneration in the putamen.

HTT Suppression does not Cause Neuronal Degeneration, Gliosis, or Inflammation

To address whether HTT reduction in cells of the putamen caused neuronal degeneration, we evaluated potential neurotoxicity by immunohistochemical staining for eGFP to identify transduced regions of the putamen, NeuN (neuronal marker), GFAP (astrocytic marker), and Iba1 (microglial marker). Coronal brain section were stained using standard DAB immunohistochemistry, and adjacent sections were compared for signs of neuron loss, increases in astrocyte proliferation (reactive astrocyosis) or increases in reactive microglia in AAV-miHDS1-treated monkeys compared to controls. Compared to AAV-eGFP- and AAV-miCONT-injected controls, AAV-miHDS1-injected animals showed no loss of NeuN-positive neurons in the putamen. Cresyl violet (Nissl) staining of adjacent coronal brain section s further supported a lack of neuronal loss. To assess whether partial HTT suppression was associated with cellular dysfunction, in contrast to frank neuronal loss, we performed QPCR analysis for DARPP-32, a highly expressed protein in GABA-ergic projection neurons of the putamen. DARPP-32 is a key mediator in numerous signal transduction cascades, and its downregulation has been reported in cases of medium spiny neuronal dysfunction in the absence of NeuN downregulation. Consequently, DARPP-32 is a valid and reliable readout of neuronal function in the putamen. QPCR analysis of transduced regions of the putamen found no significant decrease of DARPP-32 mRNA expression in monkeys injected with AAV-miHDS1 compared to controls (P>0.05).

Coronal stained sections from all treatment groups showed a mild increase in GFAP-positive astrocytes in transduced regions, likely due to the injection itself and not a reduction in HTT since equal astrocytosis was observed in all groups. IBA-1-stained sections from animals in each group showed no increases in activated microglia, except for within the injection tracts, likely due to physical perturbation of parenchyma by the needle. To further assess inflammation, expression of the pro-inflammatory cytokines interleukin 1-β (IL1-β) and tumor necrosis factor-α (TNF-α) was measured from transduced regions. Both of these cytokines are upregulated and released from astrocytes and microglia in response to distressed, neighboring neurons in the brain. QPCR analysis showed no significant increases in IL1-β (P>0.05) or TNF-α (P>0.05) in AAV-miHDS1-treated monkeys compared to AAVeGFP control animals. Interestingly, monkeys injected with AAV-miCONT showed a significant decrease in TNF-alpha expression compared to both AAV-eGFP-(P<0.05) and AAV-miHDS1-(P<0.05) animals.

Lack of Peripheral Immune Response Following AAV1-miRNA Delivery to the Putamen

Previous studies have shown that peripheral T cells infiltrate the brain following injury or infection. Thus, in addition to assaying for local inflammatory and immune responses in the putamen, cell-mediated and humoral responses were evaluated to determine whether AAV-mediated suppression of HTT induced peripheral immune responses. Relative CD4 and CD8 mRNA expression levels were determined by QPCR to address whether AAV suppression of HTT induced infiltration of peripheral helper or cytotoxic T cells, respectively. No significant differences were seen between groups in either CD4 or CD8 mRNA expression in transduced putamen samples (P>0.05). Also, no inflammatory infiltrates were noted on Nissl-stained sections from treated animals. To test if anti-AAV antibodies were induced after injection, an in vitro neutralizing antibody (Nab) assay was performed on serum collected from each animal immediately prior to surgery and at necropsy (6 weeks after injection). HuH7 cells were infected with AAV2/1 expressing LacZ in the presence of serial dilutions of rhesus serum. The transduction assay showed that the cohort of rhesus macaques used for this study displayed varying levels of neutralizing antibodies to AAV2/1 in their serum prior to surgery ranging from undetectable titers (<1:5) to the highest titer of 1:160. Four of the 11 animals showed increases in AAV2/1 Nab levels at necropsy but these increases were minor (two- to fourfold). Neither presurgical Nab levels nor the fold change in Nab expression from presurgery to necropsy correlated with levels of eGFP expression in the putamen (Pearson's correlation, r=−0.24, P=0.49 and Spearman correlation (r=0.01, P=0.9, respectively).

Discussion

Here, we present novel data showing that a partial reduction of HTT expression in the rhesus macaque putamen is well tolerated out to 6 weeks after injection. We used a multifaceted approach to assess the ability of RNAi to reduce HTT and address whether such suppression would induce behavioral or neuropathological consequences by combining assays of gross and fine motor skills with postmortem immunohistochemical, stereological, and molecular analyses of neuronal, glial, and immune profiles. Our silencing construct, miHDS1, was designed such that the target mRNA sequence displays homology to rodent, rhesus macaque, and human HTT. Therefore, HTT reduction and tolerability can be seamlessly evaluated in transgenic mice and non-human primates. Importantly, the same sequence evaluated preclinically may be utilized to evaluate safety of HTT suppression in a phase 1 clinical trial.

The selection of our injection sites in the mid- and posterior putamen was based upon the primate putamen's functional rostral-caudal gradient. Lesions of the posterior aspect of the putamen with excitotoxins or lentiviral-mediated delivery of mutated Htt elicit hyperactivity, choreiform movements, stereotypies, and/or dyskinetic movements of the limbs (either spontaneously or following apomorphine administration). Correspondingly, we have previously observed motor dysfunction detected via the Lifesaver assay and MRS following moderate neuronal loss in the mid- and posterior putamen (unpublished results from our laboratory). By contrast, lesions of the anterior putamen fail to produce similar dyskinesias. These disparate effects correspond with the inputs to the mid- and posterior putamen from the primary sensorimotor cortices including the premotor and supplementary motor areas as well as the primary motor area. By contrast, the anterior primate putamen receives cortical inputs from the frontal association areas, the dorsolateral prefrontal cortices, and the pre-supplementary motor area. Consequently, to assess the tolerability of partial HTT suppression in the mid- and posterior putamen, we employed three behavior tests that assess putamen-associated behaviors. First, to assess potential changes in general activity, we continually assessed homecage activity over the duration of the experiment using omnidirectional activity monitors placed in collars on the animals. No differences in daytime or nighttime activity were found between groups.

In an effort to detect more subtle abnormalities of limb use, muscle tone, eye movements, posture or balance, we devised a MRS based upon the clinical Unified Huntington Disease Motor Rating Scale. Our rubric assessed 24 discrete behaviors and revealed that 10 of the 11 animals showed no behavior anomalies. One AAV-miCONT-injected control animal (no. 25150) displayed a mild dystonia in his left leg. The increased muscle tone in the leg was noted on day 12 subsequent to surgery and may be the result of trauma, infection from the surgical procedure or a perturbation in the putamen due to the injection itself.

To challenge the functional integrity of the mid- and posterior putamen and its circuits, all animals were trained to perform the Lifesaver task. The task requires the animals to rapidly perform a sequence of muscle movements in the arm, hand, and fingers to obtain a reinforcer. For the straight post task, animals were trained for 21 days prior to the initiation of the experiment in an effort to increase animals' efficiency, skill, and speed of performance. Evidence suggests that overlearned sequential hand movements require the functional integrity of the posterior sensorimotor putamen in monkeys and in humans. Consistent with homecage activity and motor ratings, there were no differences in the performance of the straight post task between the HDS1 animals and the controls, again supporting the notion that knockdown of normal HTT in the mid- and posterior putamen does not significantly diminish the functional integrity of its circuits.

In contrast to the posterior regions, the anterior and midlevels of the putamen are known to play an essential role in learning new hand movement sequences. Whereas our intraputamen injections did not cover the entire anterior putamen, eGFP transfection was observed in sections ~3 mm rostral to the anterior commissure. Thus, to assess the potential disruption of a procedural learning circuit, we presented a novel question mark-shaped post 2 weeks following surgery. Despite never being trained on the distinctively shaped post, all groups successfully learned to perform the task at equal rates, suggesting that the relevant putamen circuits were functionally intact. Thus, consistent with homecage activity and motor rating data, partial knockdown of endogenous HTT in the mid- and posterior putamen did not diminish the execution of a previously learned motor task nor impair the acquisition of novel manual dexterity task.

We observed robust eGFP expression in both neurons and astrocytes throughout the commissural and postcommissural putamen following injection of each construct. Here, AAV2/1 transduced both DARPP-32-positive medium spiny projection neurons and ChAT-positive large, aspiny interneurons. While medium spiny neurons show the most dramatic cell loss in HD, the large cholinergic neurons are also affected by mHTT. Cholinergic interneurons exhibit decreased levels of ChAT and decreased levels of acetylcholine release in transgenic mouse models of HD as well as HD patients. In contrast to the findings presented here, and by other groups (Dodiya, et al. (2010). Differential transduction following basal ganglia administration of distinct pseudotyped AAV capsid serotypes in nonhuman primates. *Mol Ther* 18: 579-587) using eGFP as a reporter gene, primarily astrocytic transduction was seen following injection of AAV2/1 expressing humanized renilla GFP (hrGFP) into the cynomolgus macaque putamen. (Hadaczek, et al. (2009). Transduction of nonhuman primate brain with adeno-associated virus serotype 1: vector trafficking and immune response. *Hum Gene Ther* 20: 225-237.) Additionally, a robust anti-hrGFP antibody response was also observed, along with $CD4^+$ lymphocyte infiltration and local microglial responses, suggesting that hrGFP may be less well tolerated in the non-human primate putamen compared to eGFP.

Our finding that AAV2/1 transduces astrocytes, as well as neurons, in the putamen may provide additional benefit in animal models of the disease and in HD patients. While most therapeutic strategies for HD have targeted vulnerable neurons, a growing body of evidence has demonstrated that astrocytes also contain mHTT-positive inclusion bodies. Astrocytes expressing mHTT contain fewer glutamate transporters and are less capable of protecting against glutamate-mediated excitotoxicity. Additionally, Bradford and colleagues demonstrated that double transgenic HD mouse models expressing truncated mHTT in both neurons and glia exhibit more severe neurological symptoms than mice expressing mHTT in neurons alone (Bradford, et al. (2010). Mutant huntingtin in glial cells exacerbates neurological symptoms of Huntington disease mice. *J Biol Chem* 285: 10653-10661). Thus, partially suppressing HTT in both neurons and glia may have a more robust clinical impact.

eGFP-positive neurons and fibers, but not glia, were also found in the internal and external globus pallidus as well as the substantia nigra pars reticulata, indicating retrograde and anterograde transport of the vector, respectively. eGFP-positive fibers only were seen in the subthalamic nucleus. These findings may have important clinical implications for HD as these regions of the basal ganglia also undergo mHTT-induced cell loss and gliosis. Injections into a single brain region (putamen) may have the capability of therapeutically targeting multiple vulnerable brain regions. Specifically, transduced neurons in the globus pallidus and substantia nigra should also express HTT-specific miRNAs and may therefore be amenable to RNAi therapy. Ongoing analyses in our laboratory are currently investigating the levels of miRNA expression and concomitant levels of HTT mRNA suppression in these brain regions.

Our immunohistochemical and molecular results demonstrate a significant 45% decrease in HTT, a level of suppression which has shown therapeutic benefit in mouse models of HD without inducing toxicity (targeting both mutant and wild-type alleles). This level of suppression did not induce NeuN-positive cell loss or downregulate DARPP-32 expression. We detected a very mild upregulation of GFAP-positive astrocytes in transduced regions of the putamen. Because astrogliosis was detected in animals from all three groups, it was not due to a reduction in Htt expression in neighboring neurons. Rather, the mild astrogliosis was likely due to the injection itself. Because brains were evaluated at 6 weeks after injection, this low level of gliosis would be predicted to decrease over time. Importantly, we saw no upregulation in reactive microglia or pro-inflammatory cytokine expression which would be predicted to increase if HTT reduction induced neural toxicity.

Recombinant AAV gene transfer to the intact CNS has been shown to elicit a minimal T cell-mediated response without a salient plasma cell-mediated immune response in preclinical animal studies. Additionally, encouraging findings from recent early-stage gene therapy clinical trials for Canavan's Disease (CD), Parkinson's Disease (PD), and Leber's congenital amaurosis (LCA) wherein AAV, serotype 2, was directly injected into the brain parenchyma (CD, PD) or the retina (LCA), demonstrated only mild increases in Nab levels after injection with no signs of inflammation or adverse neurological events. The results here further support these findings and demonstrate that although monkeys had a range of preexisting, circulating Nab levels prior to surgery (from undetectable up to 1:160), there was no major increase in Nab levels (two- to fourfold maximum) 6 weeks after injection. Moreover, despite the minor increase in Nab levels in 4/11 animals, there was no correlation of Nab levels with the area fraction of GFP+ cells in the putamen. Interestingly, the presence of preexisting Nab titers at the upper range of what we report has been shown to substantially abrogate gene expression following systemic, intravascular injection of varying serotypes of AAV to target either brain or peripheral tissues. Our data are encouraging and suggest that even though NHPs and humans have natural circulating antibodies to AAV2/1, as well as other serotypes, a preexisting antibody load, at least up to the values reported here, will not limit gene transfer and should not be an exclusion criteria for clinical trials involving direct brain injections.

In summary, our results in the rhesus macaque brain further support and extend previous experiments in rodents demonstrating the safety and efficacy of a nonallele-specific HTT reduction. These findings, along with the well-established safety profile of rAAV in early phase clinical trials for a variety of neurological disorders, underscore the potential of viral-mediated RNAi as a therapy for HD.

Materials and Methods

Animals.

Eleven normal adult rhesus macaques of Indian origin (male, 7-10 kg) were utilized in this study. All monkeys were maintained one per cage on a 12-hour on/12-hour off lighting schedule with ad libitum access to food and water. All experimental procedures were performed according to Oregon National Primate Research Center and Oregon Health and Science University Institutional Animal Care and Use Committee and Institutional Biosafety Committee approved protocols.

RNAi Constructs and Viral Vector Production.

All siRNAs were generated using an algorithm developed to reduce the off-targeting potential of the antisense sequences. (See Example 1 above) siRNA sequences targeting either a sequence in exon 52 of mouse, rhesus, and human huntingtin or a control siRNA were embedded into an artificial miRNA scaffold comparable to human miR-30 to generate miHDS1 (pri: 5'-AGUGAGCGAUGCUGGCUCG-CAUGGUCGAUACUGUAAAGCCACAGAUGGGUGUCG ACCAUGCGAGCCAGCACCGCCUACU-3', predicted antisense sequence in bold, nucleotides 5-83 of SEQ ID NO: 33) or miCONT (pri: 5'-AGUGAGCGCAGCGAAC GACU-UACGCGUUUACUGUAAAGCCACA-GAUGGGUAAACGCGUAAGUCGUUCGCU ACGC-CUACU (SEQ ID NO: 200), predicted antisense sequence in bold). Artificial miRNA stem loops were cloned into a mouse U6 expression vector, and the expression cassettes were subsequently cloned into pFBGR-derived plasmids which coexpress CMV-driven GFP. Shuttle plasmids (pAAVmiHDS1-GFP and pAAVmiCONT-GFP) contain the respective transcriptional units which are flanked at each end by AAV serotype 2 145-bp inverted terminal repeat sequences. rAAV production was performed using the Baculovirus AAV System. (Smith, R H, Levy, J R and Kotin, R M (2009). A simplified baculovirus-AAV expression vector system coupled with one-step affinity purification yields high-titer rAAV stocks from insect cells. *Mol Ther* 17: 1888-1896.) Sf9 insect cells were infected with a baculovirus expressing AAV rep2, AAV cap 1, and adenovirus helper proteins and a second baculovirus expressing the miRNA and eGFP flanked by the AAV2 ITR's. The cell lysate was run through an iodixanol gradient (15%-60% wt/vol), and the iodixanol fraction containing the rAAV particles was further purified using a Mustang-Q ion exchange filter membrane. rAAV particle titer was determined by QPCR and FACS analysis. Vectors were generated by the Gene Transfer Vector Core at the University of Iowa and sent to the Oregon National Primate Research Center for injections. Twelve hours before surgery, all viral vector preps were dialyzed against Formulation Buffer 18 (Hyclone) to remove salts (3 total hours of dialysis) and diluted to a final titer of 1e12 vg/ml.

Magnetic resonance imaging and stereotaxic surgery.

Immediately prior to surgery, animals were anesthetized with Ketamine HCL (10 mg/kg), transported to the MRI, intubated and maintained on 1% isoflurane vaporized in oxygen for the duration of the scan. Animals were placed into an MRI-compatible, stereotaxic surgical frame; a T1-weighted magnetic resonance image (MRI) was conducted to obtain surgical coordinates (Siemens 3.0 T Trio MR unit). After scanning, animals were taken directly into the operating room and prepped for sterile surgery. Each animal received three microinjections per hemisphere (six injections total): the first 1 mm rostral to the anterior commissure (12 μl) and the two remaining injections (12 μl and 10 μl, respectively) spaced 3 and 6 mm caudal to the first injection. Animals were injected with 1e12 vg/ml of either AAV2/1-miHDS1-eGFP (n=4), AAV2/1-miCONT-eGFP (n=4) or AAV2/1-eGFP (n=4) at a rate of 1 μl/minute, and the needle was left in place for an additional 5 minutes to allow the injectate to diffuse from the needle tip. After microinjections were completed, the skull opening was filled with gelfoam and the incision closed.

Behavioral Analysis

General homecage activity: All animals were fitted with either nylon or aluminum collars (Primate Products) with Actical accelerometers (Respironics) mounted onto the frame. Each Actical monitor contained an omnidirectional sensor that integrated the speed and distance of whole body acceleration and produced an electrical current that varies in magnitude depending on a change in acceleration. The monitor was programmed to store the total number of activity counts for each 1-minute epoch. Animals wore activity collars 24 hours a day, 7 days a week for 3 weeks prior to surgery and each week thereafter for the duration of the study.

MRS: Three independent observes, blinded to group identity, assessed homecage behavior weekly. Twenty-four separate putamen-associated behaviors were rated including horizontal and vertical ocular pursuit, treat retrieval with both forelimbs, ability to bear weight on both hindlimbs, posture, balance, startle response and bradykinesias, dystonias and choreas of each limb and trunk. A score of 0 indicated a normal phenotype while a score of 3 indicated severely abnormal phenotypic movements. All animals were evaluated on the MRS prior to surgery to obtain baseline scores and once per week for the duration of the study.

Lifesaver test: Animals were trained to thread edible, hard treats from a straight metal rod (straight post) and then tested on their ability to remove treats from the straight post and a question mark-shaped post. All manual dexterity tasks were presented in a Wisconsin general testing apparatus (WGTA) and the latency to successfully retrieve the treat was measured separately for the left and right forelimbs. Animals were trained for 21 days on the straight post. Then, 2 weeks of baseline data were collected on the straight post only. Two weeks following surgery, animals were tested twice per week on both the straight post and the question mark-shaped post. On testing days, each animal was placed into the WGTA and their movements recorded on digital video. Each hand was tested two times with a time limit of 5 seconds for the straight post and 10 seconds for the question mark post to complete the task. The latency to remove each treat was assessed via Sony PMB software with millisecond measuring capability at a later time.

Necropsy and Tissue Processing.

Six weeks after surgery, animals were sedated with Ketamine and then deeply anesthetized with sodium pentobarbital followed by exsanguination. Brains were perfused through the ascending carotid artery with 21 of 0.9% saline, removed from the skull, placed into an ice-cold, steel brain matrix and blocked into 4-mm-thick slabs in the coronal plane. Tissue punches used for molecular analyses were obtained from each animal's left hemisphere of the transduced putamen (slabs were placed under the fluorescent scope to verify eGFP-fluorescing regions) and immediately frozen in liquid nitrogen to preserve DNA, RNA, and protein. Slabs were subsequently postfixed in 4% paraformaldehyde for histological analyses.

Quantitative Real-Time PCR.

RNA was isolated from tissue punches taken from eGFP-positive putamen using the Qiagen RNeasy kit, as per the manufacturer's instructions, and reverse transcribed with random primers and Multiscribe reverse transcriptase (Applied Biosystems, Carlsbad, Calif.). Relative gene expression was assessed via QPCR by using TaqMan primer/probe sets for DARPP-32 (Hs00259967_m1), CD4 (Rh02621720_m1), CD8 (Rh02839719_m1), IL1-β (Rh02621711_m1), or TNF-α (Rh02789784). All values were quantified by using the $\Delta\Delta$CT method (normalizing to 18S) and calibrated to AAV-GFP-injected putamen. Primers for rhesus HTT mRNA quantification were designed to flank the miHDS1 binding site in Exon 52 using Primer Express (Applied Biosystems): Forward: 5'-CGGGAGCT GTGCTCACGT-3' (SEQ ID NO: 201), Reverse: 5'-CATTTCTACC CGGCGACAAG-3' (SEQ ID NO:202)), and expression was assessed using SYBR Green detection. At the conclusion, dissociation curve (melting curve) analysis was performed to confirm specific amplification.

Immunohistochemical Analyses.

40-μm-thick, free-floating coronal brain sections were processed for immunohistochemical visualization of eGFP expression (eGFP, 1:000, Invitrogen), neurons (NeuN, 1:1000, Millipore), reactive astrocytes (GFAP, 1:2000, DAKO), or microglia (Iba1, 1:1,000; WAKO) by using the biotin-labeled antibody procedure. Following endogenous peroxidase inhibition and washes, tissues were blocked for 1 hour in 5% donkey serum, and primary antibody incubations were carried out for 24 hours at room temperature. Sections were incubated in donkey anti-rabbit or anti-mouse biotinylated IgG secondary antibodies (1:200; Vector Laboratories, Burlingame, Calif.) for 1 h at room temperature. In all staining procedures, deletion of the primary antibody served as a control. Sections were mounted onto gelatin-coated slides and coverslipped with Cytoseal 60 (Thermo Scientific, Waltham, Mass.). Images were captured by using an Olympus BX51 light microscope and DP72 digital color camera, along with an Olympus DP Controller software.

Immunofluorescence Analyses.

40-μm-thick, free-floating coronal brain sections were processed for immunofluorescent visualization of medium spiny projection neurons (DARPP-32, 1:25, Cell Signaling, Danvers, Mass.), large cholinergic neurons (ChAT, 1:500, Millipore, Billerica, Mass.), reactive astrocytes (GFAP, 1:1000, DAKO, Carpinteria, Calif.), or microglia (Iba1, 1:500; WAKO, Richmond, Va.). Following washes, tissues were blocked for 1 hour in 5% donkey serum, and primary antibody incubations were carried out for 24 hours at room temperature. Sections were incubated in donkey anti-rabbit or anti-goat Alexa-546 conjugated secondary antibodies (1:500; Invitrogen, Carlsbad, Calif.) for 1 hour at room temperature. Sections were mounted onto gelatin-coated slides and coverslipped with Slowfade Gold anti-fade mounting media containing DAPI (Invitrogen). Images were captured at 20 magnification using a Leica SP5 confocal microscope.

Stereological Determination of Vector Distribution.

The Area Fraction Fractionator (Microbrightfield) was used to quantify the fraction of eGFPpositive cells in the putamen (right hemisphere only). Every 12th coronal section (½ series, 40-μm-thick sections) through the putamen containing GFP$^+$ cells was selected for analysis. The putamen was outlined under 2 magnification, an d a rectangular lattice of points was overlaid. One marker was used to select points that fell within the region of interest (putamen), and a second marker was used to select points that fell within the subregion of interest (contained GFP-positive cells). The counting frame area was 1000 1000 μm, XY placement was 1600 1600 μm, and grid spacing was 120 μm. The area fraction estimation of GFP$^+$ cells in the putamen was determined by dividing the area of GFP+ cells by the area of the putamen and estimates provided were averaged from all sections quantified. A 3D reconstruction of the eGFP-transduced putamen was created using StereoInvestigator software by aligning contours from each section from the rostral to caudal putamen and placing skins over each. The anterior to posterior spread of eGFP transduction was determined by locating the most rostral and caudal sections through the putamen containing GFP and using a combined MRI and histology atlas of the rhesus monkey brain (Saleem and Logothetis) to identify the distance between the two (1 mm resolution).

Neutralizing Antibody Assay.

Whole blood was collected in red top Vacutainer Serum Tubes (BD) from animals prior to surgery and at necropsy, serum was collected following centrifugation at 2500 rpm for 20 minutes and stored at −80° C. until analysis. Serum was sent to the Immunology Core at the University of Pennsylvania for analyzing AAV2/1 antibody levels via an in vitro transduction assay. A 96 well plate was seeded with Huh7 cells and infected with AAV2/1-LacZ and serial dilutions of pre- and postsurgery rhesus serum. Values reported are the serum dilution at which relative luminescence units (RLUs) were reduced by 50% compared to virus control wells (no serum sample). The lower limit of detection was a ⅕ dilution, and anti-AAV2/1 rabbit serum was used at a positive control.

Statistical Analysis.

All statistical analyses were performed by using SigmaStat statistical software (SYSTAT). QPCR analyses for HTT, DARPP-32, CD4, CD8, IL1-β, and TNF-α expression, as well as Area Fraction Fractionator analyses, were performed by using a one-way ANOVA. Upon a significant effect, Bonferroni post hoc analyses were performed to assess for significant differences between individual groups. For homecage activity and Lifesaver test analyses, a two-way, repeated measures ANOVA using group and time as variables was run to determine differences between groups or over time. Post hoc analyses were performed when statistically significant differences were detected. For MRS analyses, a Kruskal-Wallis test was run followed by a Dunn's pairwise comparison to detect differences between groups. Correlational data between the area fraction of GFP in the putamen and presurgical Nab levels were determined using a Pearson's correlation for parametric data. Correlational data between the area fraction of GFP in the putamen and the fold change of Nab titers pre- and postsurgery were determined using a Spearman correlation for nonparametric data. In all cases, P<0.05 was considered significant.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A nucleic acid encoding an artificial primary miRNA transcript (pri-miRNA) consisting of, in order of position, a 5'-flanking region, a non-guide region, a loop region, a guide region, and a 3'-flanking region, wherein the guide region comprises a sequence 100% identical to cgaccaugcgagccagca (miHDS.1 guide. SEQ ID NO:7) and the non-guide region is at least 80% complementary to the guide region.

2. The nucleic acid of claim 1, wherein the guide region consists of 18-30 nucleotides.

3. The nucleic acid of claim 1, wherein the 5'-flanking region comprises a 5'-joining sequence contiguously linked to the non-guide region.

4. The nucleic acid of claim 3, wherein the 5' joining sequence consists of 5-8 nucleotides.

5. The nucleic acid of claim 2, wherein the 5'-flanking region further comprises (i) a 5'-bulge sequence positioned upstream from the 5' joining sequence;

(ii) a 5'-spacer sequence positioned upstream from the 5'-bulge sequence; and/or (iii) a 5'-upstream sequence positioned upstream from the 5'-spacer sequence.

6. The nucleic acid of claim 5, wherein the 5'-bulge sequence consists of 1-10 nucleotides, the 5'-spacer sequence consists of 10-12 nucleotides, and/or the 5'-upstream sequence consists of 30-2000 nucleotides.

7. The nucleic acid of claim 1, wherein the 3'-flanking region comprises a 3'-joining sequence contiguously linked to the guide region.

8. The nucleic acid of claim 7, wherein the 3' joining sequence consists of 5-8 nucleotides.

9. The nucleic acid of claim 8, wherein the 3'-joining sequence is at least about 85% complementary to the 5'-joining sequence.

10. The nucleic acid of claim 7, wherein the 3'-flanking region further comprises
   (i) a 3'-bulge sequence positioned downstream from the 3' joining sequence;
   (ii) a 3'-spacer sequence positioned downstream from the 3'-bulge sequence; and/or
   (iii) a 3'-downstream sequence positioned downstream from the 3'-spacer sequence.

11. The nucleic acid of claim 10, wherein the 3'-bulge sequence consists of 1-10 nucleotides, the 3'-spacer sequence consists of 10-12 nucleotides, and/or the 3'-downstream sequence is about 30-2000 nucleotides in length.

12. The nucleic acid of claim 1, wherein the loop region is from 15-25 nucleotides in length.

13. An expression cassette comprising a promoter contiguously linked to the nucleic acid of claim 1.

14. A vector comprising the expression cassette of claim 13.

15. The vector of claim 14, wherein the vector is an adeno-associated virus (AAV) vector.

16. The vector of claim 15, wherein the AAV is AAV1, AAV2, AAV4, AAV5, or AAV2/1.

17. An isolated microRNA molecule comprising the nucleic acid of claim 1.

18. A method of inducing RNA interference comprising administering to a subject an effective amount of the nucleic acid of claim 1.

19. A method of treating a subject with Huntington's Disease, comprising administering to the subject the nucleic acid of claim 1 so as to treat the Huntington's Disease.

20. A nucleic acid encoding an artificial primary miRNA transcript (pri-miRNA) consisting of, in order of position, a 5'-flanking region, a non-guide region, a loop region, a guide region, and a 3'-flanking region, wherein the guide region comprises a sequence at least 90% identical to agucgcugaugaccggga (miHDS.2 guide, SEQ ID NO:8) or acgucguaaacaagagga (miHDS.5 guide, SEQ ID NO:9) and the non-guide region is at least 80% complementary to the guide region.

* * * * *

SEQUENCE LISTING

```
<160> NUMBER OF SEQ ID NOS: 221

<210> SEQ ID NO 1
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cucgagugag cgaugcuggc ucgcaugguc gauacuguaa agccacagau gggugucgac      60
caugcgagcc agcaccgccu acuaga                                          86

<210> SEQ ID NO 2
<211> LENGTH: 86
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 2
cucgagugag cgcucccggu caucagcgac uauuccguaa agccacagau ggggauaguc    60
gcugaugacc gggaucgccu acuaga                                        86

<210> SEQ ID NO 3
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cucgagugag cgcuccucuu guuuacgacg ugaucuguaa agccacagau gggauuacgu    60
cguaaacaag aggaacgccu acuagu                                        86

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gucgaccaug cgagccagca c                                             21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
auagucgcug augaccggga u                                             21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uuacgucgua aacaagagga a                                             21

<210> SEQ ID NO 7
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cgaccaugcg agccagca                                                 18
```

-continued

```
<210> SEQ ID NO 8
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
agucgcugau gaccggga                                                      18

<210> SEQ ID NO 9
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
acgucguaaa caagagga                                                      18

<210> SEQ ID NO 10
<211> LENGTH: 163
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10
gcguuuagug aaccgucaga ugguaccguu uaaacucgag ugagcgaugc uggcucgcau        60
ggucgauacu guaaagccac agaugggugu cgaccaugcg agccagcacc gccuacuaga       120
gcggccgcca cagcggggag auccagacau gauaagauac auu                         163

<210> SEQ ID NO 11
<211> LENGTH: 163
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11
gcguuuagug aaccgucaga ugguaccguu uaaacucgag ugagcgcucc cggucaucag        60
cgacuauucc guaaagccac agauggggau agucgcugau gaccgggauc gccuacuaga       120
gcggccgcca cagcggggag auccagacau gauaagauac auu                         163

<210> SEQ ID NO 12
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12 gugagcga                                                                  8

<210> SEQ ID NO 13
<211> LENGTH: 8
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 13 gugagcgc                                                                 8

<210> SEQ ID NO 14
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14 uaaacucga                                                                9

<210> SEQ ID NO 15
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 ctcgag                                                                   6

<210> SEQ ID NO 16
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ugguaccguu                                                              10

<210> SEQ ID NO 17
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17 cgcyuac                                                                  7

<210> SEQ ID NO 18
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18 cgccuac                                                                  7

<210> SEQ ID NO 19
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 19 ctcaga                                                                      6

<210> SEQ ID NO 20
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 ctcagt                                                                      6

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agcggccgcc a                                                               11

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(17)
<223> OTHER INFORMATION: a, c, u, g, unknown or other

<400> SEQUENCE: 22
cunnnnnnnn nnnnnnngg                                                       19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(17)
<223> OTHER INFORMATION: a, c, u, g, unknown or other

<400> SEQUENCE: 23
ccnnnnnnnn nnnnnnngg                                                       19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
cugugaagcc acagaugggg                                                      19
```

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ccgugaagcc acagauggg                                                   19

<210> SEQ ID NO 26
<211> LENGTH: 2
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26 uu                                                                      2

<210> SEQ ID NO 27
<211> LENGTH: 3
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27 uuu                                                                     3

<210> SEQ ID NO 28
<211> LENGTH: 4
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28 uuuu                                                                    4

<210> SEQ ID NO 29
<211> LENGTH: 3
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29 cuu                                                                     3

<210> SEQ ID NO 30
<211> LENGTH: 4
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30 cuuu                                                                    4

<210> SEQ ID NO 31

```
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31 cuuuu                                                                    5

<210> SEQ ID NO 32
<211> LENGTH: 3
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32 uag                                                                      3

<210> SEQ ID NO 33
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
cucgagugag cgaugcuggc ucgcauggus gauacuguaa agccacagau gggugucgac        60
caugcgagcc agcaccgccu acuaga                                             86

<210> SEQ ID NO 34
<211> LENGTH: 21
<212> TYPE: DNA
<213> ORGANISM: Homo sapiens

<400> SEQUENCE: 34
gtcgtggctc gcatggtcga t                                                  21

<210> SEQ ID NO 35
<211> LENGTH: 21
<212> TYPE: DNA
<213> ORGANISM: Homo sapiens

<400> SEQUENCE: 35
atcccggtca tcagcgacta t                                                  21

<210> SEQ ID NO 36
<211> LENGTH: 21
<212> TYPE: DNA
<213> ORGANISM: Homo sapiens

<400> SEQUENCE: 36
ctgcttcttt gtcagcgcgt c                                                  21

<210> SEQ ID NO 37
<211> LENGTH: 21
<212> TYPE: DNA
<213> ORGANISM: Homo sapiens

<400> SEQUENCE: 37
gcggggcagc aggagcggta g                                                  21
```

```
<210> SEQ ID NO 38
<211> LENGTH: 21
<212> TYPE: DNA
<213> ORGANISM: Homo sapiens

<400> SEQUENCE: 38
ttcctcttgt ttacgacgtg a                                              21

<210> SEQ ID NO 39
<211> LENGTH: 21
<212> TYPE: DNA
<213> ORGANISM: Homo sapiens

<400> SEQUENCE: 39
tgggatgtag agaggcgtta g                                              21

<210> SEQ ID NO 40
<211> LENGTH: 21
<212> TYPE: DNA
<213> ORGANISM: Homo sapiens

<400> SEQUENCE: 40
tcccttggaa tgcatatcgc t                                              21

<210> SEQ ID NO 41
<211> LENGTH: 21
<212> TYPE: DNA
<213> ORGANISM: Homo sapiens

<400> SEQUENCE: 41
aacgtggacc tgcctacgga g                                              21

<210> SEQ ID NO 42
<211> LENGTH: 21
<212> TYPE: DNA
<213> ORGANISM: Homo sapiens

<400> SEQUENCE: 42
agggacagta cttcaacgct a                                              21

<210> SEQ ID NO 43
<211> LENGTH: 21
<212> TYPE: DNA
<213> ORGANISM: Homo sapiens

<400> SEQUENCE: 43
tggggacagt acttcaacgc t                                              21

<210> SEQ ID NO 44
<211> LENGTH: 21
<212> TYPE: DNA
<213> ORGANISM: Homo sapiens

<400> SEQUENCE: 44
aaggagttca tctaccgcat c                                              21

<210> SEQ ID NO 45
<211> LENGTH: 21
<212> TYPE: DNA
<213> ORGANISM: Homo sapiens

<400> SEQUENCE: 45
gagctggctc acctggttcg g                                              21
```

```
<210> SEQ ID NO 46
<211> LENGTH: 21
<212> TYPE: DNA
<213> ORGANISM: Homo sapiens

<400> SEQUENCE: 46
ctgccccagt tctagacga c                                              21

<210> SEQ ID NO 47
<211> LENGTH: 21
<212> TYPE: DNA
<213> ORGANISM: Homo sapiens

<400> SEQUENCE: 47
tgccccagtt tctagacgac t                                             21

<210> SEQ ID NO 48
<211> LENGTH: 21
<212> TYPE: DNA
<213> ORGANISM: Homo sapiens

<400> SEQUENCE: 48
gccccagttt ctagacgact t                                             21

<210> SEQ ID NO 49
<211> LENGTH: 21
<212> TYPE: DNA
<213> ORGANISM: Homo sapiens

<400> SEQUENCE: 49
ccccagtttc tagacgactt c                                             21

<210> SEQ ID NO 50
<211> LENGTH: 21
<212> TYPE: DNA
<213> ORGANISM: Homo sapiens

<400> SEQUENCE: 50
cagctaccaa gaaagaccgt g                                             21

<210> SEQ ID NO 51
<211> LENGTH: 21
<212> TYPE: DNA
<213> ORGANISM: Homo sapiens

<400> SEQUENCE: 51
ctgctgtgca gtgatgacgc a                                             21

<210> SEQ ID NO 52
<211> LENGTH: 21
<212> TYPE: DNA
<213> ORGANISM: Homo sapiens

<400> SEQUENCE: 52
atggagaccc acaggttcga g                                             21

<210> SEQ ID NO 53
<211> LENGTH: 21
<212> TYPE: DNA
<213> ORGANISM: Homo sapiens

<400> SEQUENCE: 53
```

-continued ttccgtgtgc tggctcgcat g                                              21

<210> SEQ ID NO 54
<211> LENGTH: 21
<212> TYPE: DNA
<213> ORGANISM: Homo sapiens

<400> SEQUENCE: 54
tccgtgtgct ggctcgcatg g                                              21

<210> SEQ ID NO 55
<211> LENGTH: 21
<212> TYPE: DNA
<213> ORGANISM: Homo sapiens

<400> SEQUENCE: 55
ctggctcgca tggtcgacat c                                              21

<210> SEQ ID NO 56
<211> LENGTH: 21
<212> TYPE: DNA
<213> ORGANISM: Homo sapiens

<400> SEQUENCE: 56
caccCttcag aagacgagat c                                              21

<210> SEQ ID NO 57
<211> LENGTH: 21
<212> TYPE: DNA
<213> ORGANISM: Homo sapiens

<400> SEQUENCE: 57 aacctttct gcctggtcgc c                                               21

<210> SEQ ID NO 58
<211> LENGTH: 21
<212> TYPE: DNA
<213> ORGANISM: Homo sapiens

<400> SEQUENCE: 58
gaggatgact ctgaatcgag a                                              21

<210> SEQ ID NO 59
<211> LENGTH: 21
<212> TYPE: DNA
<213> ORGANISM: Homo sapiens

<400> SEQUENCE: 59
ccggacaaag actggtacgt t                                              21

<210> SEQ ID NO 60
<211> LENGTH: 21
<212> TYPE: DNA
<213> ORGANISM: Homo sapiens

<400> SEQUENCE: 60
aagcaacgac ctgaagatcg a                                              21

<210> SEQ ID NO 61
<211> LENGTH: 21
<212> TYPE: DNA
<213> ORGANISM: Homo sapiens

<400> SEQUENCE: 61

-continued ctggagaagt cagaagacga a                              21

<210> SEQ ID NO 62
<211> LENGTH: 21
<212> TYPE: DNA
<213> ORGANISM: Homo sapiens

<400> SEQUENCE: 62
aaccaagagc ggagcaacga a                              21

<210> SEQ ID NO 63
<211> LENGTH: 21
<212> TYPE: DNA
<213> ORGANISM: Homo sapiens

<400> SEQUENCE: 63
acgggacaga attggacgaa a                              21

<210> SEQ ID NO 64
<211> LENGTH: 21
<212> TYPE: DNA
<213> ORGANISM: Homo sapiens

<400> SEQUENCE: 64
gtggaaaaga ttcatccgaa a                              21

<210> SEQ ID NO 65
<211> LENGTH: 21
<212> TYPE: DNA
<213> ORGANISM: Homo sapiens

<400> SEQUENCE: 65
cagggtagaa gaaaacgatt t                              21

<210> SEQ ID NO 66
<211> LENGTH: 21
<212> TYPE: DNA
<213> ORGANISM: Homo sapiens

<400> SEQUENCE: 66
cggctcagga aagaaacgca a                              21

<210> SEQ ID NO 67
<211> LENGTH: 21
<212> TYPE: DNA
<213> ORGANISM: Homo sapiens

<400> SEQUENCE: 67
ccccacatgg cccacgtacc t                              21

<210> SEQ ID NO 68
<211> LENGTH: 21
<212> TYPE: DNA
<213> ORGANISM: Homo sapiens

<400> SEQUENCE: 68
atccaactgc ccatgcgcca a                              21

<210> SEQ ID NO 69
<211> LENGTH: 21
<212> TYPE: DNA
<213> ORGANISM: Homo sapiens -continued

```
<400> SEQUENCE: 69
cgccaatgat gctaatgacg a                                              21

<210> SEQ ID NO 70
<211> LENGTH: 21
<212> TYPE: DNA
<213> ORGANISM: Homo sapiens

<400> SEQUENCE: 70
cagcccattc cagtctcgac a                                              21

<210> SEQ ID NO 71
<211> LENGTH: 21
<212> TYPE: DNA
<213> ORGANISM: Homo sapiens

<400> SEQUENCE: 71
accccacatg gcccacgtac c                                              21

<210> SEQ ID NO 72
<211> LENGTH: 21
<212> TYPE: DNA
<213> ORGANISM: Homo sapiens

<400> SEQUENCE: 72
agcccattcc agtctcgaca a                                              21

<210> SEQ ID NO 73
<211> LENGTH: 21
<212> TYPE: DNA
<213> ORGANISM: Homo sapiens

<400> SEQUENCE: 73
tcccaatgat atgtttcgat a                                              21

<210> SEQ ID NO 74
<211> LENGTH: 21
<212> TYPE: DNA
<213> ORGANISM: Homo sapiens

<400> SEQUENCE: 74
tcccaatgat atgtttcgat a                                              21

<210> SEQ ID NO 75
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
agugagcgau gcuggcucgc auggucgaua cuguaaagcc acagaugggu gucgaccaug     60
cgagccagca ccgccuacu                                                 79

<210> SEQ ID NO 76
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
```

```
aaaactcgag tgagcgatgc tggctcgcat ggtcgatact gtaaagccac agatggg      57
```

<210> SEQ ID NO 77
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77

```
aaaaactagt aggcggtgct ggctcgcatg gtcgacaccc atctgtggct ttacag       56
```

<210> SEQ ID NO 78
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78

```
agugagcgcu cccggucauc agcgacuauu ccguaaagcc acagauggggg auagucgcug    60 augaccggga ucgccuacu                                                  79
```

<210> SEQ ID NO 79
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79

```
aaaactcgag tgagcgctcc cggtcatcag cgactattcc gtaaagccac agatggg      57
```

<210> SEQ ID NO 80
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80

```
aaaaactagt aggcgatccc ggtcatcagc gactatcccc atctgtggct ttacag       56
```

<210> SEQ ID NO 81
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 81

```
agugagcggu gcuucuuugu cagcgcguuu ccguaaagcc acagauggggg gacgcgctga    60 caaagaagca gcgccuacu                                                  79
```

<210> SEQ ID NO 82
<211> LENGTH: 57
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 82
aaaactcgag tgagcggtgc ttctttgtca gcgcgtttcc gtaaagccac agatggg       57

<210> SEQ ID NO 83
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
aaaaactagt aggcgctgct tctttgtcag cgcgtccccc atctgtggct ttacag         56

<210> SEQ ID NO 84
<211> LENGTH: 79
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 84
agugagcgac ggggcagcag gagcgguaga cuguaaagcc acagaugggu uuaccgcucc     60
ugcugccccg ccgccuacu                                                 79

<210> SEQ ID NO 85
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
aaaactcgag tgagcgacgg ggcagcagga gcggtagact gtaaagccac agatggg       57

<210> SEQ ID NO 86
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
aaaaactagt aggcggcggg gcagcaggag cggtaaaccc atctgtggct ttacag         56

<210> SEQ ID NO 87
<211> LENGTH: 79
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 87
agugagcgcu ccucuuguuu acgacgugau cuguaaagcc acagauggga uuacgucgua     60
aacaagagga acgccuacu                                                 79

```
<210> SEQ ID NO 88
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
aaaactcgag tgagcgctcc tcttgtttac gacgtgatct gtaaagccac agatggg      57

<210> SEQ ID NO 89
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
aaaaactagt aggcgttcct cttgtttacg acgtaatccc atctgtggct ttacag       56

<210> SEQ ID NO 90
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
agugagcgcg ggauguagag aggcguuagu cuguaaagcc acagauggga uuaacgccuc   60
ucuacauccc acgccuacu                                                79

<210> SEQ ID NO 91
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
aaaactcgag tgagcgcggg atgtagagag gcgttagtct gtaaagccac agatggg      57

<210> SEQ ID NO 92
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
aaaaactagt aggcgtggga tgtagagagg cgttaatccc atctgtggct ttacag       56

<210> SEQ ID NO 93
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
agugagcgcc ccuuggaaug cauaucguug cuguaaagcc acagaugggu agcgauaugc   60
``` auuccaagggg acgccuacu                                                  79

<210> SEQ ID NO 94
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
aaaactcgag tgagcgcccc ttggaatgca tatcgttgct gtaaagccac agatggg       57

<210> SEQ ID NO 95
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aaaaactagt aggcgtccct tggaatgcat atcgctaccc atctgtggct ttacag        56

<210> SEQ ID NO 96
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
agugagcgca cguggaccug ccuacggagg ccguaaagcc acagaugggu uuccguaggc    60
agguccacgu ucgccuacu                                                 79

<210> SEQ ID NO 97
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
aaaactcgag tgagcgcacg tggacctgcc tacggaggcc gtaaagccac agatggg       57

<210> SEQ ID NO 98
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
aaaaactagt aggcgaacgt ggacctgcct acggaaaccc atctgtggct ttacag        56

<210> SEQ ID NO 99
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
agugagcgca ccgugugaau cauugucuaa cuguaaagcc acagaugggu uagacaauga    60
uucacacggu acgccuacu                                                 79

<210> SEQ ID NO 100
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
aaaactcgag tgagcgcacc gtgtgaatca ttgtctaact gtgaagccac agatggg       57

<210> SEQ ID NO 101
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
aaaaactagt aggcgtaccg tgtgaatcat tgtctaaccc atctgtggct ttacag        56

<210> SEQ ID NO 102
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
agugagcgaa gcagcuuguc cagguuuaug cuguaaagcc acagaugggu auaaaccugg    60
acaagcugcu ccgccuacu                                                 79

<210> SEQ ID NO 103
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aaaactcgag tgagcgaagc agcttgtcca ggtttatgct gtgaagccac agatggg       57

<210> SEQ ID NO 104
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
aaaaactagt aggcggagca gcttgtccag gtttataccc atctgtggct ttacag        56

<210> SEQ ID NO 105
<211> LENGTH: 79
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 105
agugagcgaa gcagcugugu uagguuuaug cuguaaagcc acagaugggu auaaaccuaa    60
cacagcugcu ccgccuacu                                                 79

<210> SEQ ID NO 106
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
aaaactcgag tgagcgaagc agctgtgtta ggtttatgct gtgaagccac agatggg      57

<210> SEQ ID NO 107
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
aaaaactagt aggcggagca gctgtgttag gtttataccc atctgtggct ttacag       56

<210> SEQ ID NO 108
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
agugagcgaa gcuguagcua ugugccuuag cuguaaagcc acagaugggu uaaggcacau    60
agcuacagcu ccgccuacu                                                 79

<210> SEQ ID NO 109
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aaaactcgag tgagcgaagc tgtagctatg tgccttagct gtgaagccac agatggg      57

<210> SEQ ID NO 110
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aaaaactagt aggcggagct gtagctatgt gccttaaccc atctgtggct ttacag       56

<210> SEQ ID NO 111
<211> LENGTH: 79
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 111
agugagcgca gcaggaguua uucugccuua cuguaaagcc acagaugggu aaggcagaau    60
aacuccugcu acgccuacu                                                 79

<210> SEQ ID NO 112
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 112
aaaactcgag tgagcgcagc aggagttatt ctgccttact gtaaagccac agatggg    57

<210> SEQ ID NO 113
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 113
aaaaactagt aggcgtagca ggagttattc tgccttaccc atctgtggct ttacag    56

<210> SEQ ID NO 114
<211> LENGTH: 79
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 114
agugagcgca gcgaacgacu uacgcguuua cuguaaagcc acagaugggu aaacgcguaa    60
gucguucgcu acgccuacu                                                 79

<210> SEQ ID NO 115
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 115
aaaactcgag tgagcgcagc gaacgactta cgcgtttact gtaaagccac agatggg    57

<210> SEQ ID NO 116
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 116
aaaaactagt aggcgtagcg aacgacttac gcgtttaccc atctgtggct ttacag    56

```
<210> SEQ ID NO 117
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
agugagcgca ccaucgaacc gucagaguua cuguaaagcc acagaugggu aacucugacg    60
guucgauggu acgccuacu                                                 79

<210> SEQ ID NO 118
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
aaaactcgag tgagcgcacc atcgaaccgt cagagttact gtgaagccac agatggg       57

<210> SEQ ID NO 119
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
aaaaactagt aggcgtacca tcgaaccgtc agagttaccc atctgtggct ttacag        56

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ttcgatctgt agcagcagct t                                              21

<210> SEQ ID NO 121
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gatccgactc accaatacc                                                 19

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ttccgaataa actccaggct t                                              21
```

```
<210> SEQ ID NO 123
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
acgtaaacaa aggacgtcc                                                    19

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
aacgttagct tcaccaacat t                                                 21

<210> SEQ ID NO 125
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
taacgtaaca gtcgtaaga                                                    19

<210> SEQ ID NO 126
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
acagcgagtt agataaagc                                                    19

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cacacgggca cagacttcca a                                                 21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
aggtgtatct cctagacact t                                                 21
```

```
<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tgtgctacgt tctacgag                                                 18

<210> SEQ ID NO 130
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tgtggacaaa gtctcttcc                                                19

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tgatgtcata gattggact                                                19

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tctgatctgt agcagcagct t                                             21

<210> SEQ ID NO 133
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ggtaagtggc catccaagc                                                19

<210> SEQ ID NO 134
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
cgagttagat aaagccccg                                                19

<210> SEQ ID NO 135
```

-continued

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ttaacctaat ctcctcccc                                                19

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
tgatgatggt gcgcagacc                                                19

<210> SEQ ID NO 137
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tatagagaga gagagaaga                                                19

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ttgatccgga ggtaggtctt t                                             21

<210> SEQ ID NO 139
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ttggtattca gtgtgatga                                                19

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ttactctcaa actttcctc                                                19

<210> SEQ ID NO 141
<211> LENGTH: 19
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
tattgtaatg ggctctgtc                                                19

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tgccttggca aactttctt                                                19

<210> SEQ ID NO 143
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
accaatttat gcctacagc                                                19

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
tttgctctgt agcagcagct t                                             21

<210> SEQ ID NO 145
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ccaatctcaa agtcatcaa                                                19

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
tagttattca ggaagtcta                                                19

<210> SEQ ID NO 147
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 147
aatcaagtag atcctcctcc                                                    20

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
tgcatctcct tgtctacgc                                                     19

<210> SEQ ID NO 149
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
tcaagctctg caaaccaga                                                     19

<210> SEQ ID NO 150
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
atgatgatgg tgcgcagac                                                     19

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tcttctagcg ttgaagtact g                                                  21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
tcttctagcg ttgaattact g                                                  21

<210> SEQ ID NO 153
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 153
gaattgttgc tggttgcact c                                              21

<210> SEQ ID NO 154
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
taggactagt cacttgtgc                                                 19

<210> SEQ ID NO 155
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tataatgctc agcctcaga                                                 19

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tttgatttgt agcagcagct t                                              21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ttttatctgt agcagcagct t                                              21

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gagtctcttg ttccgaagc                                                 19

<210> SEQ ID NO 159
<211> LENGTH: 19
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 159
tatcactcta ttctgtctc                                                    19

<210> SEQ ID NO 160
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
tcaccttcaa actatgtcc                                                    19

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
attgtcttca ggtcttcagt t                                                 21

<210> SEQ ID NO 162
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gcactccagg gcttcatcg                                                    19

<210> SEQ ID NO 163
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
aagccccgaa aaccggctt                                                    19

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ttgtccagga agtcctcaag tct                                               23

<210> SEQ ID NO 165
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 165
ccaaggctct aggtggtca                                                    19

<210> SEQ ID NO 166
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
gcaccactag ttggttgtc                                                    19

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tcatctcagc cactctgctt t                                                 21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
gtcatctcag ccactctgct t                                                 21

<210> SEQ ID NO 169
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
aatgcagtat acttcctga                                                    19

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
cacaatggca cagacttcca a                                                 21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
cacaatggcg cagacttcca a                                              21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
tctcctcagc cactctgctt t                                              21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ctcctcagcc actctgcttt t                                              21

<210> SEQ ID NO 174
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ttcctcaaat tctttcttc                                                 19

<210> SEQ ID NO 175
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ttgtacatca taggactag                                                 19

<210> SEQ ID NO 176
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ttgtctttga gatccatgc                                                 19

<210> SEQ ID NO 177
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
tcagcccaca cacagtgctt tg                                          22

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
taacaagcca gagttggtc                                              19

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ttccagaatt gatactgact t                                           21

<210> SEQ ID NO 180
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
tttcccttgg ccacttctg                                              19

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
aagcagagtt caaaagccct t                                           21

<210> SEQ ID NO 182
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ttggggatag gctgtcgcc                                              19

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
atcttcaata gacacatcgg c                                              21

<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ttccccagct ctcccaggc                                                 19

<210> SEQ ID NO 185
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ttccccaaac ctgaagctc                                                 19

<210> SEQ ID NO 186
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ttcttctcat ttcgacacc                                                 19

<210> SEQ ID NO 187
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gtcctggatg atgatgttc                                                 19

<210> SEQ ID NO 188
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
atttcaggaa ttgttaaag                                                 19

<210> SEQ ID NO 189
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189

```
ctttcagact ggacctctc                                              19
```

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190

```
actgaggagt ctcttgatct t                                           21
```

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191

```
aagcaaaaca ggtctagaat t                                           21
```

<210> SEQ ID NO 192
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192

```
ccctccctcc gttcttttt                                              19
```

<210> SEQ ID NO 193
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193

```
gttgtttgca gctctgtgc                                              19
```

<210> SEQ ID NO 194
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194

```
attctctctg actcctctc                                              19
```

<210> SEQ ID NO 195
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195

```
taatacaaag acctttaac                                              19
```

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
tatttaagga gggtgatctt t                                              21

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
aagaaatcat gaacaccgc                                                 19

<210> SEQ ID NO 198
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
taaacaaagg acgtcccgc                                                 19

<210> SEQ ID NO 199
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
aatttttcaa agttccaat                                                 19

<210> SEQ ID NO 200
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
agugagcgca gcgaacgacu uacgcguuua cuguaaagcc acagaugggu aaacgcguaa    60
gucguucgcu acgccuacu                                                 79

<210> SEQ ID NO 201
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201

```
cgggagctgt gctcacgt                                                18

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
catttctacc cggcgacaag                                              20

<210> SEQ ID NO 203
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, u, g, unknown or other
<220> FEATURE:
<221> NAME/KEY: modified_base
<222> LOCATION: (83)..(85)
<223> OTHER INFORMATION: a, c, u, g, unknown or other

<400> SEQUENCE: 203
nnnagcgagc gcagcgaacg acuuacgcgu uuacuguaaa gccacagaug ggcaaacgcg    60
uaagucguuc gcuucgccua cunnn                                        85

<210> SEQ ID NO 204
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
gcgaacgacu uacgcguuua c                                            21

<210> SEQ ID NO 205
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
aaacgcguaa gucguucgcu u                                            21

<210> SEQ ID NO 206
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, u, g, unknown or other
<220> FEATURE:
<221> NAME/KEY: modified_base
<222> LOCATION: (27)..(29)
```

```
<223> OTHER INFORMATION: a, c, u, g, unknown or other

<400> SEQUENCE: 206
nnnaagcgaa cgacuuacgc guuuacnnn                                              29

<210> SEQ ID NO 207
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, u, g, unknown or other
<220> FEATURE:
<221> NAME/KEY: modified_base
<222> LOCATION: (27)..(29)
<223> OTHER INFORMATION: a, c, u, g, unknown or other

<400> SEQUENCE: 207
nnncagccua cacgagacgc guuuacnnn                                              29

<210> SEQ ID NO 208
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
tgtgctggct cgcatggtcg acatcc                                                 26

<210> SEQ ID NO 209
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(22)
<223> OTHER INFORMATION: a, c, u, g, unknown or other

<400> SEQUENCE: 209
gcuggcucgc auggucgaua nn                                                     22

<210> SEQ ID NO 210
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
ugucgaccau gcgagccagc ac                                                     22

<210> SEQ ID NO 211
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 211
uaaggcagaa uaacuccugc ua                                              22

<210> SEQ ID NO 212
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
uuaaggcaca uagcuacagc uc                                              22

<210> SEQ ID NO 213
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
gauagucgcu gaugaccggg au                                              22

<210> SEQ ID NO 214
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
uuagacaaug auucacacgg ua                                              22

<210> SEQ ID NO 215
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
uauaaaccug gacaagcugc uc                                              22

<210> SEQ ID NO 216
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
uauaaaccua acacagcugc uc                                              22

<210> SEQ ID NO 217
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
```

```
uaaacgcgua agucguucgc ua                                              22

<210> SEQ ID NO 218
<211> LENGTH: 61
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
gcuggcucgc auggucgaua cuguaaagcc acagaugggu gucgaccaug cgagccagca    60
c                                                                    61

<210> SEQ ID NO 219
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
gcuggcucgc auggucgaua cu                                              22

<210> SEQ ID NO 220
<211> LENGTH: 61
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
cccggucauc agcgacuauu ccguaaagcc acagauggggg auagucgcug augaccggga    60
u                                                                    61

<210> SEQ ID NO 221
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
cccggucauc agcgacuauu cc                                              22
```